United States Patent
Allen et al.

(10) Patent No.: US 9,303,234 B2
(45) Date of Patent: Apr. 5, 2016

(54) HARD SURFACE CLEANERS BASED ON COMPOSITIONS DERIVED FROM NATURAL OIL METATHESIS

(75) Inventors: Dave R. Allen, Chicago, IL (US); Randal J. Bernhardt, Antioch, IL (US); Aaron Brown, Chicago, IL (US); Ronald A. Masters, Glenview, IL (US); Patrick Shane Wolfe, Palatine, IL (US); Lena Titievsky, Chicago, IL (US)

(73) Assignee: Stepan Company, Northfield, IL (US)

( * ) Notice: Subject to any disclaimer, the term of this patent is extended or adjusted under 35 U.S.C. 154(b) by 177 days.

(21) Appl. No.: 13/879,792

(22) PCT Filed: Oct. 25, 2011

(86) PCT No.: PCT/US2011/057612
§ 371 (c)(1),
(2), (4) Date: May 13, 2013

(87) PCT Pub. No.: WO2012/061103
PCT Pub. Date: May 10, 2012

(65) Prior Publication Data
US 2013/0225469 A1     Aug. 29, 2013

Related U.S. Application Data

(60) Provisional application No. 61/406,547, filed on Oct. 25, 2010, provisional application No. 61/406,556, filed on Oct. 25, 2010, provisional application No. 61/406,570, filed on Oct. 25, 2010.

(51) Int. Cl.
| | |
|---|---|
| *C11C 3/08* | (2006.01) |
| *C07C 67/26* | (2006.01) |
| *C07C 41/03* | (2006.01) |
| *C07C 43/11* | (2006.01) |
| *C07C 6/04* | (2006.01) |
| *C07C 69/533* | (2006.01) |
| *C07C 69/593* | (2006.01) |
| *C11D 1/28* | (2006.01) |
| *C11D 1/74* | (2006.01) |
| *B01F 17/00* | (2006.01) |
| *C11D 1/83* | (2006.01) |

(Continued)

(52) U.S. Cl.
CPC . *C11C 3/08* (2013.01); *A01N 25/02* (2013.01); *A01N 25/04* (2013.01); *A01N 25/30* (2013.01); *A01N 33/12* (2013.01); *A01N 37/18* (2013.01); *A01N 37/44* (2013.01); *A01N 41/04* (2013.01); *A61K 8/416* (2013.01); *A61K 8/42* (2013.01); *A61K 8/44* (2013.01); *A61K 8/466* (2013.01); *A61K 8/92* (2013.01); *A61Q 5/12* (2013.01); *A61Q 19/10* (2013.01); *A62D 1/0071* (2013.01); *B01F 17/0028* (2013.01); *B01F 17/0057* (2013.01); *C07C 6/04* (2013.01); *C07C 41/03* (2013.01); *C07C 43/11* (2013.01); *C07C 67/26* (2013.01); *C07C 69/533* (2013.01); *C07C 69/593* (2013.01); *C07C 209/12* (2013.01); *C07C 211/21* (2013.01); *C07C 219/08* (2013.01); *C07C 231/12* (2013.01); *C07C 237/16* (2013.01); *C07C 303/18* (2013.01); *C08G 65/2615* (2013.01); *C08K 5/01* (2013.01); *C08K 5/20* (2013.01); *C11C 3/00* (2013.01); *C11D 1/002* (2013.01); *C11D 1/04* (2013.01); *C11D 1/28* (2013.01); *C11D 1/62* (2013.01); *C11D 1/74* (2013.01); *C11D 1/83* (2013.01); *C11D 1/92* (2013.01); *C11D 1/94* (2013.01); *C11D 3/48* (2013.01); *C09K 8/00* (2013.01); *C09K 15/28* (2013.01); *C11D 1/652* (2013.01); *C11D 1/90* (2013.01)

(58) Field of Classification Search
CPC ............ C11D 1/90; C11D 1/652; C11D 1/94
See application file for complete search history.

(56) References Cited

U.S. PATENT DOCUMENTS

| | | | |
|---|---|---|---|
| 2,653,970 | A | 9/1953 | Fessler et al. |
| 3,169,142 | A | 2/1965 | Knaggs et al. |

(Continued)

FOREIGN PATENT DOCUMENTS

| | | |
|---|---|---|
| WO | 2008046106 A2 | 4/2008 |
| WO | WO-2008048522 | 4/2008 |

(Continued)

OTHER PUBLICATIONS

Mol J.C, "Catalytic metathesis of unsaturated fatty acid esters and oils" Topic in Catalysis, vol. 27, No. 1-4; Feb. 1, 2004, pp. 97-104.

(Continued)

*Primary Examiner* — Gregory Webb
(74) *Attorney, Agent, or Firm* — Dilworth IP LLC

(57) ABSTRACT

Aqueous hard surface cleaner compositions derived from metathesized natural oil feedstocks are disclosed. In one aspect, the compositions comprise at least one anionic surfactant derived from a metathesis-derived C10-C17 monounsaturated acid, 5 octadecene-1,18-dioic acid, or their ester derivatives. In another aspect, aqueous hard surface cleaners comprising at least one nonionic or amphoteric surfactant derived from a metathesis-derived C10-C17 monounsaturated acid, octadecene-1,18-dioic acid, or their ester derivatives are disclosed. The aqueous cleaners noted above rival or outperform commercial baselines in a Gardner straight-line washability test. Industrial degreasers comprising a C10 or C12 amide solvent and derived from a metathesis-derived C10-C17 monounsaturated acid are superior to commercial standards.

13 Claims, No Drawings

(51) Int. Cl.

| | | |
|---|---|---|
| C11D 1/94 | (2006.01) | |
| C07C 211/21 | (2006.01) | |
| C07C 237/16 | (2006.01) | |
| A01N 25/04 | (2006.01) | |
| A01N 33/12 | (2006.01) | |
| A01N 37/18 | (2006.01) | |
| A01N 37/44 | (2006.01) | |
| A01N 41/04 | (2006.01) | |
| A61K 8/41 | (2006.01) | |
| A61K 8/42 | (2006.01) | |
| A61K 8/44 | (2006.01) | |
| A61K 8/46 | (2006.01) | |
| A61Q 5/12 | (2006.01) | |
| A61Q 19/10 | (2006.01) | |
| A62D 1/02 | (2006.01) | |
| C11D 1/62 | (2006.01) | |
| C11D 1/92 | (2006.01) | |
| C11D 1/04 | (2006.01) | |
| A01N 25/02 | (2006.01) | |
| A61K 8/92 | (2006.01) | |
| C08K 5/01 | (2006.01) | |
| C08K 5/20 | (2006.01) | |
| C11C 3/00 | (2006.01) | |
| C11D 3/48 | (2006.01) | |
| C07C 219/08 | (2006.01) | |
| A01N 25/30 | (2006.01) | |
| C07C 209/12 | (2006.01) | |
| C07C 231/12 | (2006.01) | |
| C07C 303/18 | (2006.01) | |
| C11D 1/00 | (2006.01) | |
| C08G 65/26 | (2006.01) | |
| C09K 8/00 | (2006.01) | |
| C09K 15/28 | (2006.01) | |
| C11D 1/90 | (2006.01) | |
| C11D 1/65 | (2006.01) | |

(56) References Cited

U.S. PATENT DOCUMENTS

| | | | |
|---|---|---|---|
| 3,544,613 A | 12/1970 | Knaggs et al. | |
| 3,929,678 A | 12/1975 | Laughlin et al. | |
| 4,087,457 A | 5/1978 | Convers et al. | |
| 4,148,821 A | 4/1979 | Nussbaum et al. | |
| 4,267,123 A | 5/1981 | Chen et al. | |
| 4,275,013 A | 6/1981 | Tokosh et al. | |
| 4,545,941 A * | 10/1985 | Rosenburg | 554/163 |
| 5,482,908 A | 1/1996 | Le-khac | |
| 5,770,549 A | 6/1998 | Gross | |
| 5,814,590 A | 9/1998 | Sherry et al. | |
| 5,929,022 A | 7/1999 | Velazquez | |
| 5,990,064 A | 11/1999 | Barger et al. | |
| 6,071,873 A | 6/2000 | Mertens | |
| 6,281,178 B1 | 8/2001 | Ryklin et al. | |
| 6,284,723 B1 | 9/2001 | Zhou et al. | |
| 6,303,564 B1 * | 10/2001 | Littau et al. | 510/505 |
| 6,319,887 B1 | 11/2001 | Mertens | |
| 6,399,553 B1 | 6/2002 | Cable et al. | |
| 6,489,285 B2 | 12/2002 | Faber | |
| 6,511,953 B1 | 1/2003 | Fontana et al. | |
| 6,605,584 B2 | 8/2003 | Fong et al. | |
| 6,949,498 B2 | 9/2005 | Murphy et al. | |
| 6,953,773 B2 | 10/2005 | Pereira et al. | |
| 7,576,227 B2 | 8/2009 | Bicerano et al. | |
| 7,960,599 B2 | 6/2011 | Millis et al. | |
| 8,067,610 B2 | 11/2011 | Schrodi | |
| 2002/0072288 A1 * | 6/2002 | Hei et al. | 442/59 |
| 2005/0274399 A1 * | 12/2005 | Heise et al. | 134/42 |
| 2007/0167332 A1 | 7/2007 | Subramanian et al. | |
| 2008/0033026 A1 | 2/2008 | Zullo et al. | |
| 2008/0139443 A1 | 6/2008 | Buzinski et al. | |
| 2009/0202598 A1 * | 8/2009 | Kravtchenko et al. | 424/401 |
| 2009/0264672 A1 * | 10/2009 | Abraham et al. | 560/190 |
| 2010/0093596 A1 | 4/2010 | Tadrowski | |
| 2010/0145086 A1 | 6/2010 | Schrodi et al. | |
| 2010/0184855 A1 * | 7/2010 | Bernhardt et al. | 514/529 |
| 2010/0282467 A1 | 11/2010 | Hutchison et al. | |
| 2011/0113679 A1 | 5/2011 | Cohen et al. | |
| 2011/0192421 A1 | 8/2011 | Llosas et al. | |
| 2011/0313180 A1 | 12/2011 | Uptain et al. | |
| 2012/0071676 A1 | 3/2012 | Schrodi et al. | |
| 2012/0197031 A1 | 8/2012 | Firth et al. | |
| 2013/0035502 A1 | 2/2013 | Cohen et al. | |
| 2013/0035532 A1 | 2/2013 | Schrodi | |

FOREIGN PATENT DOCUMENTS

| | | |
|---|---|---|
| WO | 2008063322 A2 | 5/2008 |
| WO | 2008063322 A3 | 5/2008 |
| WO | WO-2009127367 | 10/2009 |
| WO | WO-2011075642 | 6/2011 |

OTHER PUBLICATIONS

Extended European Search Report, European Patent Office, mailed in EP Application 11838507.9 on Apr. 14, 2014.
Tetrahedron 68 2012 , 1117.
Appl. Catal.A. 346 2009 , 158.
J.C. Mol., Topics in Catalysis 27 2004 , 97.
J. C. Mol., Green Chem., 4 2002 , 5.

* cited by examiner

HARD SURFACE CLEANERS BASED ON COMPOSITIONS DERIVED FROM NATURAL OIL METATHESIS

FIELD OF THE INVENTION

The invention relates to hard surface cleaners, and particularly to compositions useful therein as surfactants or solvents that derive from natural oil metathesis.

BACKGROUND OF THE INVENTION

Hard surface cleaners continuously evolve and adapt to customer demands, changing times, and increasingly strict health and environmental regulations. Successful hard surface cleaners can remove greasy dirt from smooth or highly polished surfaces and disinfect them without leaving behind noticeable films or streaks. Modern aqueous cleaners, designed primarily for home or institutional use, typically include one or more surfactants in addition to water. Commonly, the cleaners include a small proportion of low-toxicity organic solvent(s), antimicrobial agents, buffers, sequestering agents, builders, bleaching agents, hydrotropes, and other components. As formulators seek to create more environmentally friendly products, they often reduce the amount of solvent(s), bring pH closer to neutral (5-9), and choose builders/buffers such as organic acid salts (citrate) that generally have lower performance than phosphates or EDTA. Thus, a key to achieving "squeaky clean" performance resides in identifying surfactants that are compatible with the other cleaner components (including other surfactants) and work synergistically with them to deliver good results. Industrial hard surface cleaners, which are used along with appropriate engineering controls, are frequently solvent-based and can handle greater degreasing challenges.

Among thousands of references related to hard surface cleaners, the mere handful here illustrates the diverse area: U.S. Pat. No. 5,770,549 (non-solvent cleaner using 3-67% of a sugar surfactant and 1-3% of a $C_6$-$C_{12}$ alcohol ethoxylate); U.S. Pat. No. 5,814,590 (non-streak cleaner comprising a dianionic sulfosuccinamate and a polyethoxylated alcohol surfactant); U.S. Pat. No. 6,281,178 (detergent surfactant, detergent builder, and hydrotrope for solvent-free cleaner); U.S. Pat. No. 6,284,723 (antimicrobial formulation comprising an amine oxide and a quaternary ammonium surfactant); U.S. Pat. No. 6,399,553 (anionic surfactant mixture comprising an alkyl diphenyloxide disulfonate and an alkane sulfonate); U.S. Pat. No. 6,511,953 (bleaching agent, buffer to maintain pH at least 11.5, and a surfactant mixture comprising an ethoxylated nonionic surfactant and an anionic surfactant); and U.S. Pat. No. 6,605,584 (an ethoxylated quat and a short-chain alcohol ethoxylate surfactant combined with a quaternary ammonium compound for antimicrobial efficacy) and U.S. Pat. Appl. Publ. No. 2010/0184855 (sulfoestolides as surfactants).

Occasionally, hard-surface cleaners have been formulated to contain fatty esters or amides made by hydrolysis or transesterification of triglycerides, which are typically animal or vegetable fats. Consequently, the fatty portion of the acid or ester will typically have 6-22 carbons with a mixture of saturated and internally unsaturated chains. Depending on source, the fatty acid or ester often has a preponderance of $C_{16}$ to $C_{22}$ component. For instance, methanolysis of soybean oil provides the saturated methyl esters of palmitic ($C_{16}$) and stearic ($C_{18}$) acids and the unsaturated methyl esters of oleic ($C_{18}$ mono-unsaturated), linoleic ($C_{18}$ di-unsaturated), and α-linolenic ($C_{18}$ tri-unsaturated) acids. These materials are generally less than completely satisfactory, however, because compounds having such large carbon chains can behave functionally as soil under some cleaning conditions.

Recent improvements in metathesis catalysts (see J. C. Mol, *Green Chem.* 4 (2002) 5) provide an opportunity to generate reduced chain length, monounsaturated feedstocks, which are valuable for making detergents and surfactants, from $C_{16}$ to $C_{22}$-rich natural oils such as soybean oil or palm oil. Soybean oil and palm oil can be more economical than, for example, coconut oil, which is a traditional starting material for making detergents. As Professor Mol explains, metathesis relies on conversion of olefins into new products by rupture and reformation of carbon-carbon double bonds mediated by transition metal carbene complexes. Self-metathesis of an unsaturated fatty ester can provide an equilibrium mixture of starting material, an internally unsaturated hydrocarbon, and an unsaturated diester. For instance, methyl oleate(methyl cis-9-octadecenoate) is partially converted to 9-octadecene and dimethyl 9-octadecene-1,18-dioate, with both products consisting predominantly of the trans-isomer. Metathesis effectively isomerizes the cis-double bond of methyl oleate to give an equilibrium mixture of cis- and trans-isomers in both the "unconverted" starting material and the metathesis products, with the trans-isomers predominating.

Cross-metathesis of unsaturated fatty esters with olefins generates new olefins and new unsaturated esters that can have reduced chain length and that may be difficult to make otherwise. For instance, cross-metathesis of methyl oleate and 3-hexene provides 3-dodecene and methyl 9-dodecenoate (see also U.S. Pat. No. 4,545,941). Terminal olefins are particularly desirable synthetic targets, and Elevance Renewable Sciences, Inc. recently described an improved way to prepare them by cross-metathesis of an internal olefin and an α-olefin in the presence of a ruthenium alkylidene catalyst (see U.S. Pat. Appl. Publ. No. 2010/0145086). A variety of cross-metathesis reactions involving an α-olefin and an unsaturated fatty ester (as the internal olefin source) are described. Thus, for example, reaction of soybean oil with propylene followed by hydrolysis gives, among other things, 1-decene, 2-undecenes, 9-decenoic acid, and 9-undecenoic acid. Despite the availability (from cross-metathesis of natural oils and olefins) of unsaturated fatty esters having reduced chain length and/or predominantly trans-configuration of the unsaturation, surfactants have generally not been made from these feedstocks.

We recently described new compositions made from feedstocks based on self-metathesis of natural oils or cross-metathesis of natural oils and olefins. In particular, we identified esteramines and ester quats, fatty amides, fatty amines and amidoamines, quaternized amines, betaines, sulfobetaines, alkoxylates, sulfonates, sulfo-estolides, and other compositions made by derivatizing the unique feedstocks (see coopending, PCT/US11/57596, PCT/US11/57597, PCT/US11/57595, PCT/US11/57602, PCT/US11/57605, PCT/US11/57609, respectively), all filed Oct. 25, 2011. The feedstocks, which include metathesis-derived $C_{10}$-$C_{17}$ monounsaturated acids, octadecene-1,18-dioic acid, and their ester derivatives, preferably have at least 1 mole % of trans-$\Delta^9$ unsaturation. Because performance of a particular surfactant or blend of surfactants in a hard surface cleaner is not easily inferred from surfactant structure, we performed extensive experimental investigations to identify subclasses of surfactants having desirable attributes for use in hard surface cleaners.

New surfactant classes are always of interest to formulators of hard surface cleaners. Surfactants based on renewable resources will continue to be in demand as alternatives to petroleum-based surfactants. Traditional natural sources of fatty acids and esters used for making surfactants generally have predominantly (or exclusively) cis-isomers and lack relatively short-chain (e.g., $C_{10}$ or $C_{12}$) unsaturated fatty portions. Metathesis chemistry provides an opportunity to generate precursors having shorter chains and mostly trans-isomers, which could impart improved performance when the precursors are converted to downstream compositions (e.g., in surfactants). Formulators will benefit from identification of particular subclasses of surfactants that derive from renewable sources and have desirable attributes for hard surface cleaners.

SUMMARY OF THE INVENTION

In one aspect, the invention relates to hard surface cleaners comprising at least one anionic surfactant derived from a metathesis-derived $C_{10}$-$C_{17}$ monounsaturated acid, octadecene-1,18-dioic acid, or their ester derivatives. The anionic surfactant is selected from $C_{10}$, $C_{12}$, $C_{16}$, or $C_{18}$ sulfonates, $C_{10}$ amide sulfonates, sulfonated $C_{10}$ fatty ester alkoxylates, sulfonated $C_{12}$ mid-EO fatty ester alkoxylates, $C_{12}$ amidoamine sulfonates, $C_{12}$ or $C_{18}$ amidoamine betaine sulfonates, $C_{10}$, $C_{12}$, $C_{16}$, or $C_{18}$ amidoamine oxide sulfonates, sulfonated $C_{18}$ low-EO fatty ester alkoxylates, $C_{18}$ diamidoamine sulfonates, $C_{18}$ amidoamine dibetaine sulfonates, $C_{18}$ amidoamine diquat sulfonates, sulfo-estolides of $C_{10}$ unsaturated fatty acids and $C_{10}$ or $C_{18}$ saturated fatty acids, sulfo-estolides of $C_{10}$ or $C_{12}$ unsaturated fatty esters and $C_{10}$ or $C_{12}$ saturated fatty acids, sulfo-estolides of $C_{12}$ unsaturated fatty acids, sulfo-estolides of $C_{12}$ unsaturated fatty acids and $C_{12}$ or $C_{18}$ saturated fatty acids, and sulfo-estolides of $C_{18}$ dibasic esters and $C_{10}$ fatty acids. Preferably, these cleaners include one or more other components, including water, an organic solvent, a nonionic surfactant, and the like.

In another aspect, the invention relates to hard surface cleaners comprising at least one nonionic or amphoteric surfactant derived from a metathesis-derived $C_{10}$-$C_{17}$ monounsaturated acid, octadecene-1,18-dioic acid, or their ester derivatives. The nonionic or amphoteric surfactant is selected from $C_{10}$ or $C_{12}$ amides, $C_{10}$, $C_{12}$, or $C_{18}$ imidazoline quat sulfonates, $C_{10}$ or $C_{12}$ mid- or high-EO fatty ester alkoxylates, $C_{10}$ amine oxides, $C_{10}$ betaines, $C_{10}$ and $C_{12}$ sulfobetaines, $C_{12}$ amidoamine sulfobetaines, $C_{10}$ or $C_{12}$ amidoamine quat sulfonates, $C_{16}$ amidoamines, $C_{16}$ amidoamine betaines, $C_{18}$ mid- or high-EO ethoxylates, $C_{18}$ amidoamine monobetaines, $C_{18}$ amidoamine dibetaines, $C_{18}$ amidoamine monobetaine oxides, $C_{18}$ amidoamine monobetaine quats, $C_{18}$ amidoamine monobetaine esters, $C_{18}$ amidoamine oxide carboxylates, $C_{18}$ esteramines, $C_{18}$ diamides, amidoamine sulfobetaines made from cross-metathesized palm or soybean oil or from self-metathesized soybean oil, amidoamine betaines made from cross-metathesized or self-metathesized soybean oil, and amidoamine oxides made from cross-metathesized soybean oil. Preferably, these cleaners include one or more other components, including water, an organic solvent, an anionic surfactant, and the like.

We surprisingly found that the aqueous cleaners noted above rival or outperform commercial mainstays in a standard Gardner straight-line washability test.

The invention includes industrial degreasers comprising at least one solvent derived from a metathesis-derived $C_{10}$-$C_{17}$ monounsaturated acid and selected from $C_{10}$ or $C_{12}$ amides. We surprisingly found that the $C_{10}$ or $C_{12}$ amides are superior to commercial standards, neat or diluted, in a test designed to measure the suitability of a solvent for use in an industrial degreaser.

DETAILED DESCRIPTION OF THE INVENTION

Hard surface cleaners of the invention include a surfactant derived from natural oil metathesis. In some formulations, this surfactant is anionic; in others, it is nonionic or amphoteric.

Hard Surface Cleaners: Anionic Surfactant from Natural Oil Metathesis

These hard surface cleaners comprise at least one anionic surfactant derived from metathesis of a natural oil. Preferably, the cleaners also include one or more other components, e.g., water, an organic solvent, and a nonionic or amphoteric surfactant.

When present, the amount of water used is typically in the range of 50 to 99 wt. %, preferably from 70 to 98 wt. %, and more preferably from 80 to 96 wt. %. Conveniently, the hard surface cleaner is supplied or sold as a concentrate and contains the minimum amount of water needed to solubilize the components. The formulator or even the ultimate customer may dilute the concentrate with water for normal use.

Suitable organic solvents are described below. They are typically used in an amount within the range of 0.5 to 20 wt. %, preferably from 1 to 10 wt. %, and more preferably from 3 to 8 wt. %.

A conventional nonionic or amphoteric surfactant can be included. Suitable amphoteric and nonionic surfactants for use in these formulations are summarized further below. When used, the amount of nonionic or amphoteric surfactant is typically within the range of 0.1 to 10 wt. %, preferably from 0.2 to 5 wt. %, and more preferably from 0.3 to 2 wt. %. If desired, a nonionic or amphoteric surfactant derived from natural oil metathesis can be used in addition to or instead of the conventional nonionic or amphoteric surfactant.

An anionic surfactant derived from metathesis of a natural oil is included. However, not all such compositions are suitable for use. Through extensive experimentation, we identified particular classes of compositions that perform as well or better than commercial anionic surfactants in hard surface cleaners.

Thus, suitable anionic surfactants derive from a metathesis-derived $C_{10}$-$C_{17}$ monounsaturated acid, octadecene-1,18-dioic acid, or their ester derivatives and are selected from $C_{10}$, $C_{12}$, $C_{16}$, or $C_{18}$ sulfonates, $C_{10}$ amide sulfonates, sulfonated $C_{10}$ fatty ester alkoxylates, sulfonated $C_{12}$ mid-EO fatty ester alkoxylates, $C_{12}$ amidoamine sulfonates, $C_{12}$ or $C_{18}$ amidoamine betaine sulfonates, $C_{10}$, $C_{12}$, $C_{16}$, or $C_{18}$ amidoamine oxide sulfonates, sulfonated $C_{18}$ low-EO fatty ester alkoxylates, $C_{18}$ diamidoamine sulfonates, $C_{18}$ amidoamine dibetaine sulfonates, $C_{18}$ amidoamine diquat sulfonates, sulfo-estolides of $C_{10}$ unsaturated fatty acids and $C_{10}$ or $C_{18}$ saturated fatty acids, sulfo-estolides of $C_{10}$ or $C_{12}$ unsaturated fatty esters and $C_{10}$ or $C_{12}$ saturated fatty acids, sulfo-estolides of $C_{12}$ unsaturated fatty acids, sulfo-estolides of $C_{12}$ unsaturated fatty acids and $C_{12}$ or $C_{18}$ saturated fatty acids, and sulfo-estolides of $C_{18}$ dibasic esters and $C_{10}$ fatty acids.

As used herein, "low-EO" alkoxylates have an average of 0.5 to 5 EO units, "mid-EO" alkoxylates have an average of 5 to 15 EO units, and "high-EO" alkoxylates have an average of 15 to 50 EO units.

General Note Regarding Chemical Structures:

As the skilled person will recognize, products made in accordance with the invention are typically mixtures of cis- and trans-isomers. Except as otherwise indicated, all of the structural representations provided herein show only a trans-isomer. The skilled person will understand that this convention is used for convenience only, and that a mixture of cis- and trans-isomers is understood unless the context dictates otherwise. (The "C18-" series of products in the examples below, for instance, are nominally 100% trans-isomers whereas the "Mix-" series are nominally 80:20 trans-/cis-isomer mixtures.) Structures shown often refer to a principal product that may be accompanied by a lesser proportion of other components or positional isomers. For instance, reaction products from modified triglycerides are complex mixtures. As another example, sulfonation or sulfitation processes often give mixtures of sultones, alkanesulfonates, and alkenesulfonates, in addition to isomerized products. Thus, the structures provided represent likely or predominant products. Charges may or may not be shown but are understood, as in the case of amine oxide structures. Counterions, as in quaternized compositions, are not usually included, but they are understood by the skilled person from the context.

The anionic surfactant is preferably selected from $C_{12}$ amidoamine betaine sulfonates and sulfo-estolides of $C_{10}$ unsaturated fatty acids and $C_{18}$ saturated fatty acids.

In one preferred aspect, the anionic surfactant is a $C_{12}$ amidoamine betaine sulfonate. These compounds are conveniently made be reacting a metathesis-derived $C_{12}$ monounsaturated methyl ester with DMAPA, followed by conversion to a betaine with sodium monochloroacetate under basic conditions, followed by sulfitation. A particularly preferred $C_{12}$ amidoamine betaine sulfonate has the structure:

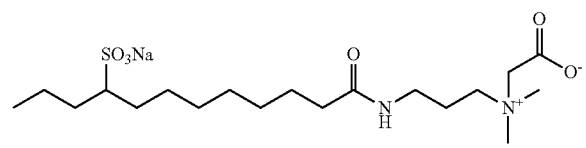

In another preferred aspect, the anionic surfactant is a sulfo-estolide of a $C_{10}$ unsaturated fatty acid and a $C_{18}$ saturated fatty acid. These are conveniently made by sulfonating a mixture comprising a $C_{10}$ unsaturated fatty acid and a $C_{18}$ saturated fatty acid, followed by neutralization. A particularly preferred sulfo-estolide has the structure:

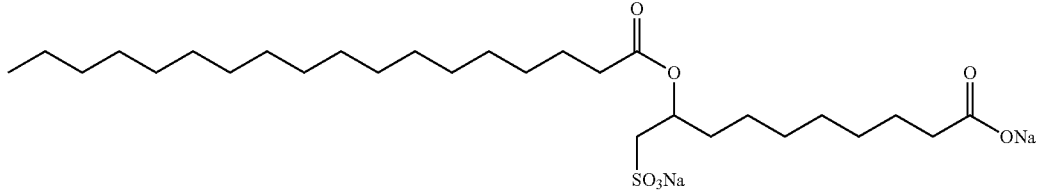

The amount of anionic surfactant used is typically within the range of 0.1 to 10 wt. %, preferably from 0.2 to 5 wt. %, and more preferably from 0.3 to 2 wt. %.

As the examples below demonstrate, the cleaners identified above rival or outperform commercial baselines in a Gardner straight-line washability test. In this test, the anionic surfactant derives from metathesis of a natural oil. It is used as a replacement for a commercial anionic surfactant, Stepanol® WA-Extra PCK (sodium lauryl sulfate) in a formulation that also includes water, organic solvent, and nonionic surfactant. We found that only certain subclasses of tested compositions performed as well or better than the control in the washability test (see Table 8), while other compositions, often structurally similar, performed poorly in the test (see Table 9).

The $C_{10}$-$C_{17}$ monounsaturated acid, octadecene-1,18-dioic acid, or their ester derivatives used as a reactant is derived from metathesis of a natural oil. Traditionally, these materials, particularly the short-chain acids and derivatives (e.g., 9-decylenic acid or 9-dodecylenic acid) have been difficult to obtain except in lab-scale quantities at considerable expense. However, because of the recent improvements in metathesis catalysts, these acids and their ester derivatives are now available in bulk at reasonable cost. Thus, the $C_{10}$-$C_{17}$ monounsaturated acids and esters are conveniently generated by cross-metathesis of natural oils with olefins, preferably α-olefins, and particularly ethylene, propylene, 1-butene, 1-hexene, 1-octene, and the like. Self-metathesis of the natural oil or a $C_{10}$ acid or ester precursor (e.g., methyl 9-decenoate) provides the $C_{18}$ diacid or diester in optimal yield when it is the desired product.

Preferably, at least a portion of the $C_{10}$-$C_{17}$ monounsaturated acid has "$\Delta^9$" unsaturation, i.e., the carbon-carbon double bond in the $C_{10}$-$C_{17}$ acid is at the 9-position with respect to the acid carbonyl. In other words, there are preferably seven carbons between the acid carbonyl group and the olefin group at C9 and C10. For the $C_{11}$ to $C_{17}$ acids, an alkyl chain of 1 to 7 carbons, respectively is attached to C10. Preferably, the unsaturation is at least 1 mole % trans-$\Delta^9$, more preferably at least 25 mole % trans-$\Delta^9$, more preferably at least 50 mole % trans-$\Delta^9$, and even more preferably at least 80% trans-$\Delta^9$. The unsaturation may be greater than 90 mole %, greater than 95 mole %, or even 100% trans-$\Delta^9$. In contrast, naturally sourced fatty acids that have $\Delta^9$ unsaturation, e.g., oleic acid, usually have ~100% cis-isomers.

Although a high proportion of trans-geometry (particularly trans-$\Delta^9$ geometry) may be desirable in the metathesis-derived fatty amines and derivatives of the invention, the skilled person will recognize that the configuration and the exact location of the carbon-carbon double bond will depend on reaction conditions, catalyst selection, and other factors. Metathesis reactions are commonly accompanied by isomerization, which may or may not be desirable. See, for example, G. Djigoué and M. Meier, *Appl. Catal. A: General* 346 (2009) 158, especially FIG. 3. Thus, the skilled person might modify the reaction conditions to control the degree of isomerization or alter the proportion of cis- and trans-isomers generated. For instance, heating a metathesis product in the presence of an inactivated metathesis catalyst might allow the skilled person to induce double bond migration to give a lower proportion of product having trans-$\Delta^9$ geometry.

An elevated proportion of trans-isomer content (relative to the usual all-cis configuration of the natural monounsaturated acid or ester) imparts different physical properties to surfactant compositions made from them, including, for example, modified physical form, melting range, compactability, and other important properties. These differences should allow formulators that use surfactants greater latitude or expanded choice as they use them in cleaners, fabric treatment, personal care, agricultural uses, and other end uses, particularly hard surface cleaners.

Suitable metathesis-derived $C_{10}$-$C_{17}$ monounsaturated acids include, for example, 9-decylenic acid (9-decenoic acid), 9-undecenoic acid, 9-dodecylenic acid (9-dodecenoic acid), 9-tridecenoic acid, 9-tetradecenoic acid, 9-pentadecenoic acid, 9-hexadecenoic acid, 9-heptadecenoic acid, and the like, and their ester derivatives.

Usually, cross-metathesis or self-metathesis of the natural oil is followed by separation of an olefin stream from a modified oil stream, typically by distilling out the more volatile olefins. The modified oil stream is then reacted with a lower alcohol, typically methanol, to give glycerin and a mixture of alkyl esters. This mixture normally includes saturated $C_6$-$C_{22}$ alkyl esters, predominantly $C_{16}$-$C_{18}$ alkyl esters, which are essentially spectators in the metathesis reaction. The rest of the product mixture depends on whether cross- or self-metathesis is used. When the natural oil is self-metathesized and then transesterified, the alkyl ester mixture will include a $C_{18}$ unsaturated diester. When the natural oil is cross-metathesized with an α-olefin and the product mixture is transesterified, the resulting alkyl ester mixture includes a $C_{10}$ unsaturated alkyl ester and one or more $C_{11}$ to $C_{17}$ unsaturated alkyl ester coproducts in addition to the glycerin by-product. The terminally unsaturated $C_{10}$ product is accompanied by different coproducts depending upon which α-olefin(s) is used as the cross-metathesis reactant. Thus, 1-butene gives a $C_{12}$ unsaturated alkyl ester, 1-hexene gives a $C_{14}$ unsaturated alkyl ester, and so on. As is demonstrated in the examples below, the $C_{10}$ unsaturated alkyl ester is readily separated from the $C_{11}$ to $C_{17}$ unsaturated alkyl ester and each is easily purified by fractional distillation. These alkyl esters are excellent starting materials for making the inventive hard surface cleaners.

Natural oils suitable for use as a feedstock to generate the $C_{10}$-$C_{17}$ monounsaturated acid, octadecene-1,18-dioic acid, or their ester derivatives from self-metathesis or cross-metathesis with olefins are well known. Suitable natural oils include vegetable oils, algal oils, animal fats, tall oils, derivatives of the oils, and combinations thereof. Thus, suitable natural oils include, for example, soybean oil, palm oil, rapeseed oil, coconut oil, palm kernel oil, sunflower oil, safflower oil, sesame oil, corn oil, olive oil, peanut oil, cottonseed oil, canola oil, castor oil, tallow, lard, poultry fat, fish oil, and the like. Soybean oil, palm oil, rapeseed oil, and mixtures thereof are preferred natural oils.

Genetically modified oils, e.g., high-oleate soybean oil or genetically modified algal oil, can also be used. Preferred natural oils have substantial unsaturation, as this provides a reaction site for the metathesis process for generating olefins. Particularly preferred are natural oils that have a high content of unsaturated fatty groups derived from oleic acid. Thus, particularly preferred natural oils include soybean oil, palm oil, algal oil, and rapeseed oil.

A modified natural oil, such as a partially hydrogenated vegetable oil, can be used instead of or in combination with the natural oil. When a natural oil is partially hydrogenated, the site of unsaturation can migrate to a variety of positions on the hydrocarbon backbone of the fatty ester moiety. Because of this tendency, when the modified natural oil is self-metathesized or is cross-metathesized with the olefin, the reaction products will have a different and generally broader distribution compared with the product mixture generated from an unmodified natural oil. However, the products generated from the modified natural oil are similarly converted to anionic surfactant compositions for the hard surface cleaners.

An alternative to using a natural oil as a feedstock to generate the $C_{10}$-$C_{17}$ monounsaturated acid, octadecene-1,18-dioic acid, or their ester derivatives from self-metathesis or cross-metathesis with olefins is a monounsaturated fatty acid obtained by the hydrolysis of a vegetable oil or animal fat, or an ester or salt of such an acid obtained by esterification of a fatty acid or carboxylate salt, or by transesterification of a natural oil with an alcohol. Also useful as starting compositions are polyunsaturated fatty esters, acids, and carboxylate salts. The salts can include an alkali metal (e.g., Li, Na, or K); an alkaline earth metal (e.g., Mg or Ca); a Group 13-15 metal (e.g., B, Al, Sn, Pb, or Sb), or a transition, lanthanide, or actinide metal. Additional suitable starting compositions are described at pp. 7-17 of PCT application WO 2008/048522, the contents of which are incorporated by reference herein.

The other reactant in the cross-metathesis reaction is an olefin. Suitable olefins are internal or α-olefins having one or more carbon-carbon double bonds. Mixtures of olefins can be used. Preferably, the olefin is a monounsaturated $C_2$-$C_{10}$ α-olefin, more preferably a monounsaturated $C_2$-$C_8$ α-olefin. Preferred olefins also include $C_4$-$C_9$ internal olefins. Thus, suitable olefins for use include, for example, ethylene, propylene, 1-butene, cis- and trans-2-butene, 1-pentene, isohexylene, 1-hexene, 3-hexene, 1-heptene, 1-octene, 1-nonene, 1-decene, and the like, and mixtures thereof.

Cross-metathesis is accomplished by reacting the natural oil and the olefin in the presence of a homogeneous or heterogeneous metathesis catalyst. The olefin is omitted when the natural oil is self-metathesized, but the same catalyst types are generally used. Suitable homogeneous metathesis catalysts include combinations of a transition metal halide or oxo-halide (e.g., $WOCl_4$ or $WCl_6$) with an alkylating cocatalyst (e.g., $Me_4Sn$). Preferred homogeneous catalysts are well-defined alkylidene (or carbene) complexes of transition metals, particularly Ru, Mo, or W. These include first and second-generation Grubbs catalysts, Grubbs-Hoveyda catalysts, and the like. Suitable alkylidene catalysts have the general structure:

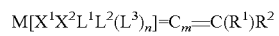

where M is a Group 8 transition metal, $L^1$, $L^2$, and $L^3$ are neutral electron donor ligands, n is 0 (such that $L^3$ may not be present) or 1, m is 0, 1, or 2, $X^1$ and $X^2$ are anionic ligands, and $R^1$ and $R^2$ are independently selected from H, hydrocarbyl, substituted hydrocarbyl, heteroatom-containing hydrocarbyl, substituted heteroatom-containing hydrocarbyl, and functional groups. Any two or more of $X^1$, $X^2$, $L^1$, $L^2$, $L^3$, $R^1$ and $R^2$ can form a cyclic group and any one of those groups can be attached to a support.

First-generation Grubbs catalysts fall into this category where m=n=0 and particular selections are made for n, $X^1$, $X^2$, $L^1$, $L^2$, $L^3$, $R^1$ and $R^2$ as described in U.S. Pat. Appl. Publ. No. 2010/0145086 ("the '086 publication"), the teachings of which related to all metathesis catalysts are incorporated herein by reference.

Second-generation Grubbs catalysts also have the general formula described above, but $L^1$ is a carbene ligand where the carbene carbon is flanked by N, O, S, or P atoms, preferably by two N atoms. Usually, the carbene ligand is party of a cyclic group. Examples of suitable second-generation Grubbs catalysts also appear in the '086 publication.

In another class of suitable alkylidene catalysts, $L^1$ is a strongly coordinating neutral electron donor as in first- and second-generation Grubbs catalysts, and $L^2$ and $L^3$ are weakly coordinating neutral electron donor ligands in the form of optionally substituted heterocyclic groups. Thus, $L^2$ and $L^3$ are pyridine, pyrimidine, pyrrole, quinoline, thiophene, or the like.

In yet another class of suitable alkylidene catalysts, a pair of substituents is used to form a bi- or tridentate ligand, such as a biphosphine, dialkoxide, or alkyldiketonate. Grubbs-Hoveyda catalysts are a subset of this type of catalyst in which $L^2$ and $R^2$ are linked. Typically, a neutral oxygen or nitrogen coordinates to the metal while also being bonded to a carbon that is α-, β-, or γ- with respect to the carbene carbon to provide the bidentate ligand. Examples of suitable Grubbs-Hoveyda catalysts appear in the '086 publication.

The structures below provide just a few illustrations of suitable catalysts that may be used:

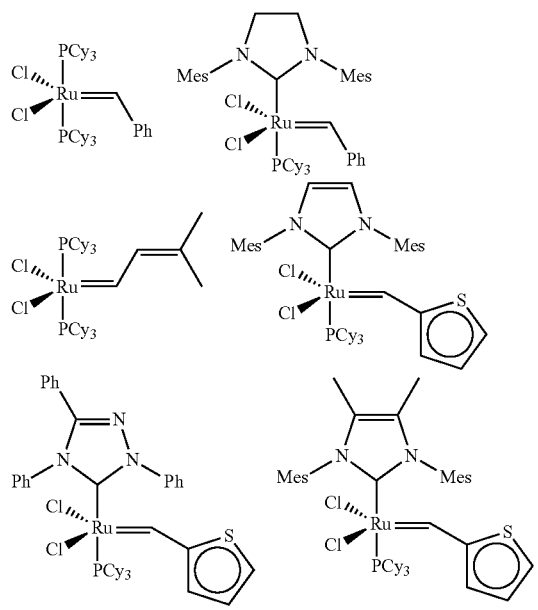

Heterogeneous catalysts suitable for use in the self- or cross-metathesis reaction include certain rhenium and molybdenum compounds as described, e.g., by J. C. Mol in Green Chem. 4 (2002) 5 at pp. 11-12. Particular examples of catalyst systems that include $Re_2O_7$ on alumina promoted by an alkylating cocatalyst such as a tetraalkyl tin lead, germanium, or silicon compound. Others include $MoCl_3$ or $MoCl_5$ on silica activated by tetraalkyltins.

For additional examples of suitable catalysts for self- or cross-metathesis, see U.S. Pat. No. 4,545,941, the teachings of which are incorporated herein by reference, and references cited therein.

The metathesis-derived $C_{10}$-$C_{17}$ monounsaturated acid, octadecene-1,18-dioic acid, or their ester derivatives are converted to particular subclasses of sulfonates, amide sulfonates, sulfonated fatty ester alkoxylates, amidoamine sulfonates, amidoamine betaine sulfonates, amidoamine oxide sulfonates, sulfo-estolides, and other compositions that are useful as anionic surfactants in hard surface cleaners. General synthetic procedures for making these compositions are provided below (General procedures A-L) and are summarized for each particular composition prepared in Tables 2A and 2B. For instance, amidoamine sulfonate C12-42 is conveniently made using Methods E and J by reacting methyl 9-dodecenoate with DMAPA to make the DMAPA amide, followed by sulfitation of the internal double bond to give the amidoamine sulfonate.

The hard surface cleaner can include additional conventional components. Commonly, the cleaners include one or more additives such as builders, buffers, abrasives, electrolytes, bleaching agents, fragrances, dyes, foaming control agents, antimicrobial agents, thickeners, pigments, gloss enhancers, enzymes, detergents, surfactants, cosolvents, dispersants, polymers, silicones, hydrotropes, and the like.

Hard Surface Cleaners: Nonionic or Amphoteric Surfactant from Natural Oil Metathesis These hard surface cleaners comprise at least one nonionic or amphoteric surfactant derived from metathesis of a natural oil. Preferably, the cleaners include one or more other components, including water, an organic solvent, an anionic surfactant, and the like.

When used, the amount of water used is typically in the range of 50 to 99 wt. %, preferably from 70 to 98 wt. %, and more preferably from 80 to 96 wt. %.

Suitable organic solvents are described below. They are typically used in an amount within the range of 0.5 to 20 wt. %, preferably from 1 to 10 wt. %, and more preferably from 3 to 8 wt. %.

A conventional anionic surfactant can be included. Suitable anionic surfactants for use in these formulations are summarized further below. The amount anionic surfactant used is typically within the range of 0.1 to 10 wt. %, preferably from 0.2 to 5 wt. %, and more preferably from 0.3 to 2 wt. %. If desired, an anionic surfactant derived from natural oil metathesis can be used in addition to or instead of the conventional anionic surfactant.

A nonionic or amphoteric surfactant derived from metathesis of a natural oil is included. However, not all such compositions are suitable for use. Through extensive experimentation, we identified particular classes of compositions that perform as well or better than commercial anionic surfactants in hard surface cleaners.

Thus, suitable nonionic or amphoteric surfactants derive from a metathesis-derived $C_{10}$-$C_{17}$ monounsaturated acid, octadecene-1,18-dioic acid, or their ester derivatives and are selected from $C_{10}$ or $C_{12}$ amides, $C_{10}$, $C_{12}$, or $C_{18}$ imidazoline quat sulfonates, $C_{10}$ or $C_{12}$ mid- or high-EO fatty ester alkoxylates, $C_{10}$ amine oxides, $C_{10}$ betaines, $C_{10}$ and $C_{12}$ sulfobetaines, $C_{12}$ amidoamine sulfobetaines, $C_{10}$ or $C_{12}$ amidoamine quat sulfonates, $C_{16}$ amidoamines, $C_{16}$ amidoamine betaines, $C_{18}$ mid- or high-EO ethoxylates, $C_{18}$ amidoamine monobetaines, $C_{18}$ amidoamine dibetaines, $C_{18}$ amidoamine monobetaine oxides, $C_{18}$ amidoamine monobetaine quats, $C_{18}$ amidoamine monobetaine esters, $C_{18}$ amidoamine oxide carboxylates, $C_{18}$ esteramines, $C_{18}$ diamides, amidoamine sulfobetaines made from cross-metathesized palm or soybean oil or from self-metathesized soybean oil, amidoamine betaines made from cross-metathesized or self-metathesized soybean oil, and amidoamine oxides made from cross-metathesized soybean oil.

Particularly preferred nonionic or amphoteric surfactants include quaternized $C_{12}$ imidazoline sulfonates, $C_{10}$ high-EO fatty ester alkoxylates, $C_{12}$ amidoamine sulfobetaines, $C_{10}$ quaternized amidoamine sulfonates, and amidoamine sulfobetaines made from cross-metathesized soybean oil.

In one preferred aspect, the nonionic or amphoteric surfactant is a quaternized $C_{12}$ imidazoline sulfonate. These compounds are conveniently made by reacting a metathesis-derived $C_{12}$ monounsaturated methyl ester with DETA to give the an amide intermediate, followed by acid-catalyzed ring closure to the imidazoline, followed by sulfitation of the olefin. A particularly preferred example has the structure:

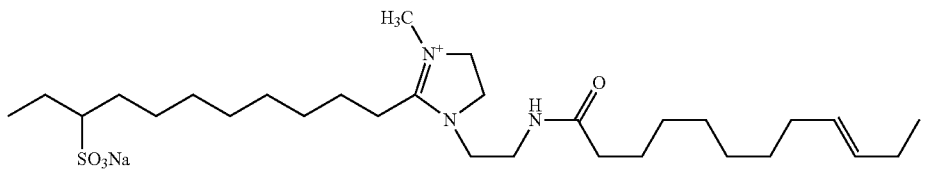

In another preferred aspect, the nonionic or amphoteric surfactant is a $C_{10}$ high-EO fatty ester alkoxylate. Reaction of a metathesis-derived fatty methyl ester with EO in the presence of an insertion catalyst readily provides the alkoxylate. One preferred example has the structure:

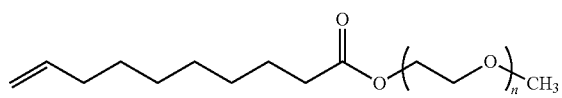

where n, the average number of oxyethylene units, has a value within the range of 15 to 50.

In another preferred aspect, the nonionic or amphoteric surfactant is a $C_{12}$ amidoamine sulfobetaine. These compounds can be prepared by reacting a metathesis-derived fatty methyl ester with DMAPA, followed by conversion of the tertiary amine group to a sulfobetaine. The fatty DMAPA amine is reacted, for example, with the reaction product of epichlorohydrin and sodium metabisulfite. A preferred example:

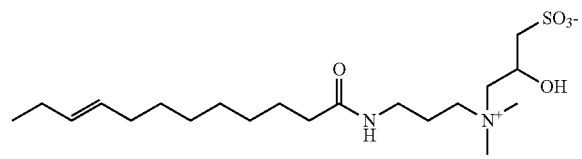

In yet another preferred aspect, the nonionic or amphoteric surfactant is a $C_{10}$ quaternized amidoamine sulfonate. Suitable compositions of this type can be made by reacting a metathesis-derived $C_{10}$ methyl ester with DMAPA, followed by quaternization of the tertiary amine with dimethyl sulfate, followed by sulfitation of the olefin. One preferred example has the structure:

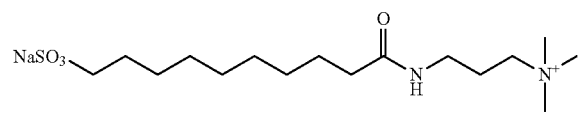

The amount of nonionic or amphoteric surfactant used is typically within the range of 0.1 to 10 wt. %, preferably from 0.2 to 5 wt. %, and more preferably from 0.3 to 2 wt. %.

As the examples below demonstrate, the aqueous cleaners identified above rival or outperform commercial baselines in a Gardner straight-line washability test. In this test, the nonionic or amphoteric surfactant derives from metathesis of a natural oil. It is used in a formulation that also includes water, organic solvent, and an anionic surfactant. The control sample omits the test composition. We found that only certain subclasses of tested compositions performed as well or better than the control in the washability test (see Table 6), while other compositions, often structurally similar, performed poorly in this test (see Table 7).

The $C_{10}$-$C_{17}$ monounsaturated acid, octadecene-1,18-dioic acid, or their ester derivatives used to make the anionic surfactant come from natural oil metathesis as is detailed fully above. The feedstocks are converted to particular subclasses of amides, quaternized imidazoline sulfonates, fatty ester alkoxylates, amine oxides, betaines, amidoamine sulfobetaines, quaternized amidoamine sulfonates, amidoamine monobetaines, amidoamine monobetaine oxides, amidoamine sulfobetaines made from cross-metathesized palm or soybean oil or from self-metathesized soybean oil, amidoamine betaines made from cross-metathesized or self-metathesized soybean oil, amidoamine oxides made from cross-metathesized soybean oil, and other compositions that are useful as nonionic or amphoteric surfactants in hard surface cleaners. General synthetic procedures for making these compositions are provided below (General procedures A-L) and are summarized for each particular composition prepared in Table 2. For instance, amine oxide C10-39 is conveniently made using Methods E, G, and D by reacting methyl 9-dodecenoate with dimethylamine (DMA) to make the amide, followed by reduction of the amide to an amine with lithium aluminum hydride, followed by oxidation of the amine with hydrogen peroxide to give the amine oxide. The hard surface cleaner can include the additional conventional components (builders, buffers, etc.) noted earlier.

Any of the aqueous hard surface cleaners discussed above can contain the following components:

Organic Solvents

An organic solvent, preferably a water-soluble one, can be included in the hard surface cleaners. Preferred solvents include alcohols, glycols, glycol ethers, glycol ether esters, amides, esters, and the like. Examples include $C_1$-$C_6$ alcohols, $C_1$-$C_6$ diols, $C_3$-$C_{24}$ glycol ethers, and mixtures thereof. Suitable alcohols include, for example, methanol, ethanol, 1-propanol, isopropanol, 1-butanol, 1-pentanol, 1-hexanol, amyl alcohol, and mixtures thereof. Suitable glycol ethers include, e.g., ethylene glycol n-butyl ether, ethylene glycol n-propyl ether, propylene glycol methyl ether, propylene glycol n-propyl ether, propylene glycol tert-butyl ether, propylene glycol n-butyl ether, diethylene glycol n-butyl ether, dipropylene glycol methyl ether, and the like, and mixtures thereof. Suitable glycol ether esters include, for example, propylene glycol methyl ether acetate, propylene glycol n-butyl ether acetate, and the like.

Other organic solvents suitable for use in hard surface cleaners are well known in the art and have been described for example, in U.S. Pat. Nos. 5,814,590, 6,284,723, 6,399,553, and 6,605,584, and in U.S. Pat. Appl. Publ. No. 2010/0184855, the teachings of which are incorporated herein by reference.

Anionic Surfactants

Anionic surfactants generally have a molecular weight below 10,000 and comprise one or more functional groups that exhibit a net anionic charge when in aqueous solution. Suitable anionic surfactants include fatty alkyl sulfates, fatty alkyl ether sulfates, paraffin sulfonates, olefin sulfonates, alkyl aryl sulfonates, alkyl ester sulfonates, fatty ester sulfonates, sulfosuccinate esters, organic phosphates, alkyl alkoxylated sulfates, and the like.

Additional examples of suitable anionic surfactants are described in U.S. Pat. Nos. 3,929,678, 5,929,022, 6,399,553, 6,489,285, 6,511,953, 6,949,498, and U.S. Pat. Appl. Publ. No. 2010/0184855, the teachings of which are incorporated herein by reference.

Nonionic or Amphoteric Surfactants

Nonionic surfactants typically function as wetting agents, hydrotropes, and/or couplers. Suitable nonionic surfactants include, for example, fatty alcohols, alcohol fatty esters, fatty alcohol ethoxylates, alkylphenol ethoxylates, alkoxylate block copolymers, alkoxylated fatty amides, fatty amides, fatty amine oxides, castor oil alkoxylates, polyol esters, fatty methyl esters, glycerol esters, glycol fatty esters, tallow amine ethoxylates, polyethylene glycol esters, and the like. Fatty alcohol ethoxylates are preferred.

Suitable amphoteric surfactants include, for example, amine oxides, betaines, sulfobetaines, and the like. Specific examples include cocoamidopropylamine oxide, cetamine oxide, lauramine oxide, myristylamine oxide, stearamine oxide, alkyl betaines, cocobetaines, and amidopropyl betaines, (e.g., lauryl betaines, cocoamidopropyl betaines, lauramidopropyl betaines), and combinations thereof.

Other suitable nonionic and amphoteric surfactants are disclosed in U.S. Pat. Nos. 5,814,590, 6,281,178, 6,284,723, 6,605,584, and 6,511,953, the teachings of which related to those surfactants are incorporated herein by reference.

In another aspect, the invention relates to solvent-based degreasers intended principally for industrial use. These degreasers comprise a $C_{10}$ or $C_{12}$ amide solvent derived from a metathesis-derived $C_{10}$-$C_{17}$ monounsaturated acid or its ester derivative. We found that the amide solvents are superior to commercial standards when used neat or diluted in removing greasy soils. In a comparison test, standard soil (Gardner ASTM D4488-95 A5) is applied to a white tile with a brush. A drop of test solvent is applied to the tile, and after each 10 seconds (neat samples), or 30 seconds (diluted), a second drop is applied adjacent to the first, and so on. After a few minutes the dropping is stopped and the tile rinsed, photographed, and judged for cleaning versus control neat, and in formulation diluted. Neat test samples of $C_{10}$ or $C_{12}$ amide solvent derived from a $C_{10}$-$C_{12}$ monounsaturated acid or its ester derivative, when compared with Steposol™ M8-10, a mixture of N,N-dimethylcapramide and N,N-dimethylcaprylamide (product of Stepan), outperform the control (see Table 10). Diluted samples comprising the amides, a fatty amine oxide, and deionized water also outperform an aqueous control sample. Meanwhile a host of other test materials fail to match the performance of the control.

In a preferred aspect, the $C_{10}$ or $C_{12}$ amide solvent derives from a metathesis-derived $C_{10}$-$C_{17}$ monounsaturated acid or its ester derivative. Suitable amides are conveniently made by heating a metathesis-derived $C_{10}$ or $C_{12}$ fatty methyl ester with dimethylamine. Particularly preferred examples have the structure:

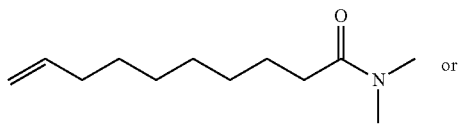 or

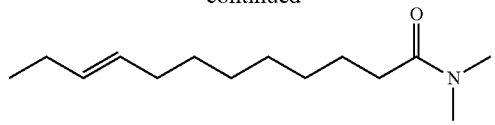

The solvent-based degreaser can be used neat (i.e., at full strength), or it can be diluted with water. Diluted compositions comprise at least 2 wt. % of the degreaser.

In a preferred aspect, the diluted degreaser comprises from 2 to 20 wt. % of the $C_{10}$ or $C_{12}$ amide solvent, from 3 to 25 wt. % of a fatty amine oxide, and from 55 to 95 wt. % of water.

The degreaser can include one or more conventional additives (builders, buffers, bleaching agents, surfactants, cosolvents, etc.) as described above for the aqueous hard surface cleaners.

The following examples merely illustrate the invention. Those skilled in the art will recognize many variations that are within the spirit of the invention and scope of the claims.

Feedstock Syntheses

Preparation of Methyl 9-Decenoate ("C10-0") and Methyl 9-Dodecenoate ("C12-0")

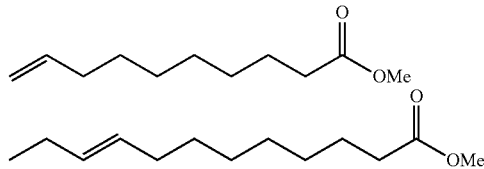

The procedures of U.S. Pat. Appl. Publ. No. 2011/0113679, the teachings of which are incorporated herein by reference, are used to generate feedstocks C10-0 and C12-0 as follows:

Example 1A

Cross-Metathesis of Soybean Oil and 1-Butene

A clean, dry, stainless-steel jacketed 5-gallon Parr reactor equipped with a dip tube, overhead stirrer, internal cooling/heating coils, temperature probe, sampling valve, and relief valve is purged with argon to 15 psig. Soybean oil (SBO, 2.5 kg, 2.9 mol, Costco, $M_n$=864.4 g/mol, 85 weight % unsaturation, sparged with argon in a 5-gal container for 1 h) is added to the Parr reactor. The reactor is sealed, and the SBO is purged with argon for 2 h while cooling to 10° C. After 2 h, the reactor is vented to 10 psig. The dip tube valve is connected to a 1-butene cylinder (Airgas, CP grade, 33 psig headspace pressure, >99 wt. %) and re-pressurized to 15 psig with 1-butene. The reactor is again vented to 10 psig to remove residual argon. The SBO is stirred at 350 rpm and 9-15° C. under 18-28 psig 1-butene until 3 mol 1-butene per SBO olefin bond are transferred into the reactor (~2.2 kg 1-butene over 4-5 h).

A toluene solution of [1,3-bis-(2,4,6-trimethylphenyl)-2-imidazolidinylidene]-dichlororuthenium(3-methyl-2-butenylidene)(tricyclohexylphosphine) (C827, Materia) is prepared in a Fischer-Porter pressure vessel by dissolving 130 mg catalyst in 30 g of toluene (10 mol ppm per mol olefin bond of SBO). The catalyst mixture is added to the reactor via the reactor dip tube by pressurizing the headspace inside the Fischer-Porter vessel with argon to 50-60 psig. The Fischer-Porter vessel and dip tube are rinsed with additional toluene (30 g). The reaction mixture is stirred for 2.0 h at 60° C. and is then allowed to cool to ambient temperature while the gases in the headspace are vented.

After the pressure is released, the reaction mixture is transferred to a round-bottom flask containing bleaching clay (Pure-Flo® B80 CG clay, product of Oil-Dri Corporation of America, 2% w/w SBO, 58 g) and a magnetic stir bar. The reaction mixture is stirred at 85° C. under argon. After 2 h, during which time any remaining 1-butene is allowed to vent, the reaction mixture cools to 40° C. and is filtered through a glass frit. An aliquot of the product mixture is transesterified with 1% w/w NaOMe in methanol at 60° C. By gas chromatography (GC), it contains: methyl 9-decenoate (22 wt. %), methyl 9-dodecenoate (16 wt. %), dimethyl 9-octadecenedioate (3 wt. %), and methyl 9-octadecenoate (3 wt. %).

The results compare favorably with calculated yields for a hypothetical equilibrium mixture: methyl 9-decenoate (23.4 wt. %), methyl 9-dodecenoate (17.9 wt %), dimethyl 9-octadecenedioate (3.7 wt. %), and methyl 9-octadecenoate (1.8 wt. %).

Example 1B

The procedure of Example 1A is generally followed with 1.73 kg SBO and 3 mol 1-butene/SBO double bond. An aliquot of the product mixture is transesterified with sodium methoxide in methanol as described above. The products (by GC) are: methyl 9-decenoate (24 wt. %), methyl 9-dodecenoate (18 wt. %), dimethyl 9-octadecenedioate (2 wt. %), and methyl 9-octadecenoate (2 wt. %).

Example 1C

The procedure of Example 1A is generally followed with 1.75 kg SBO and 3 mol 1-butene/SBO double bond. An aliquot of the product mixture is transesterified with sodium methoxide in methanol as described above. The products (by GC) are: methyl 9-decenoate (24 wt. %), methyl 9-dodecenoate (17 wt. %), dimethyl 9-octadecenedioate (3 wt. %), and methyl 9-octadecenoate (2 wt. %).

Example 1D

The procedure of Example 1A is generally followed with 2.2 kg SBO and 3 mol 1-butene/SBO double bond. Additionally, the toluene used to transfer the catalyst (60 g) is replaced with SBO. An aliquot of the product mixture is transesterified with sodium methoxide in methanol as described above. The products (by GC) are: methyl 9-decenoate (25 wt. %), methyl 9-dodecenoate (18 wt. %), dimethyl 9-octadecenedioate (3 wt. %), and methyl 9-octadecenoate (1 wt. %).

Example 1E

Separation of Olefins from Modified Triglyceride

A 12-L round-bottom flask equipped with a magnetic stir bar, heating mantle, and temperature controller is charged with the combined reaction products from Examples 1A-1D (8.42 kg). A cooling condenser with a vacuum inlet is attached to the middle neck of the flask and a receiving flask is connected to the condenser. Volatile hydrocarbons (olefins) are removed from the reaction product by vacuum distillation. Pot temperature: 22° C.-130° C.; distillation head temperature: 19° C.-70° C.; pressure: 2000-160 µtorr. After removing the volatile hydrocarbons, 5.34 kg of non-volatile residue remains. An aliquot of the non-volatile product mixture is transesterified with sodium methoxide in methanol as described above. The products (by GC) are: methyl 9-decenoate (32 wt. %), methyl 9-dodecenoate (23 wt. %), dimethyl 9-octadecenedioate (4 wt. %), and methyl 9-octadecenoate (5 wt. %). This mixture is also called "UTG-0." (An analogous product made from palm oil is called "PUTG-0.")

Example 1F

Methanolysis of Modified Triglyceride

A 12-L round-bottom flask fitted with a magnetic stir bar, condenser, heating mantle, temperature probe, and gas adapter is charged with sodium methoxide in methanol (1% w/w, 4.0 L) and the non-volatile product mixture produced in Example 1E (5.34 kg). The resulting light-yellow heterogeneous mixture is stirred at 60° C. After 1 h, the mixture turns homogeneous and has an orange color (pH=11). After 2 h of reaction, the mixture is cooled to ambient temperature and two layers form. The organic phase is washed with aqueous methanol (50% v/v, 2×3 L), separated, and neutralized by washing with glacial acetic acid in methanol (1 mol HOAc/mol NaOMe) to pH=6.5. Yield: 5.03 kg.

Example 1G

Isolation of Methyl Ester Feedstocks

A 12-L round-bottom flask fitted with a magnetic stirrer, packed column, and temperature controller is charged with the methyl ester mixture produced in example 1F (5.03 kg), and the flask is placed in a heating mantle. The glass column is 2"×36" and contains 0.16" Pro-Pak™ stainless-steel saddles (Cannon Instrument Co.). The column is attached to a fractional distillation head to which a 1-L pre-weighed flask is fitted for collecting fractions. Distillation is performed under vacuum (100-120 µtorr). A reflux ratio of 1:3 is used to isolate methyl 9-decenoate ("C10-0") and methyl 9-dodecenoate ("C12-0"). Samples collected during the distillation, distillation conditions, and the composition of the fractions (by GC) are shown in Table 1. A reflux ratio of 1:3 refers to 1 drop collected for every 3 drops sent back to the distillation column. Combining appropriate fractions yields methyl 9-decenoate (1.46 kg, 99.7% pure) and methyl 9-dodecenoate (0.55 kg, >98% pure).

TABLE 1

Isolation of C10-0 and C12-0 by Distillation

| Distillation Fractions # | Head temp. (° C.) | Pot temp. (° C.) | Vacuum (µtorr) | Weight (g) | C10-0 (wt %) | C12-0 (wt %) |
| --- | --- | --- | --- | --- | --- | --- |
| 1 | 40-47 | 104-106 | 110 | 6.8 | 80 | 0 |
| 2 | 45-46 | 106 | 110 | 32.4 | 99 | 0 |
| 3 | 47-48 | 105-110 | 120 | 223.6 | 99 | 0 |
| 4 | 49-50 | 110-112 | 120 | 283 | 99 | 0 |
| 5 | 50 | 106 | 110 | 555 | 99 | 0 |
| 6 | 50 | 108 | 110 | 264 | 99 | 0 |
| 7 | 50 | 112 | 110 | 171 | 99 | 0 |
| 8 | 51 | 114 | 110 | 76 | 97 | 1 |
| 9 | 65-70 | 126-128 | 110 | 87 | 47 | 23 |
| 10 | 74 | 130-131 | 110 | 64 | 0 | 75 |
| 11 | 75 | 133 | 110 | 52.3 | 0 | 74 |
| 12 | 76 | 135-136 | 110 | 38 | 0 | 79 |
| 13 | 76 | 136-138 | 100 | 52.4 | 0 | 90 |
| 14 | 76 | 138-139 | 100 | 25.5 | 0 | 85 |

TABLE 1-continued

Isolation of C10-0 and C12-0 by Distillation

| Distillation Fractions # | Head temp. (° C.) | Pot temp. (° C.) | Vacuum (μtorr) | Weight (g) | C10-0 (wt %) | C12-0 (wt %) |
|---|---|---|---|---|---|---|
| 15 | 76-77 | 140 | 110 | 123 | 0 | 98 |
| 16 | 78 | 140 | 100 | 426 | 0 | 100 |

Preparation of Methyl 9-Hexadecenoate ("C16-0") Feedstock

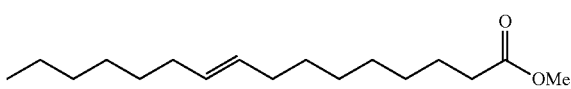 [SMILES: CCCCCC/C=C/CCCCCCCC(=O)OC]

The procedures of Example 1A is generally followed except that 1-octene is cross-metathesized with soybean oil instead of 1-butene. Combined reaction products are then stripped as described in Example 1E to remove the more volatile unsaturated hydrocarbon fraction from the modified oil fraction. The procedure of Example 1F is used to convert the modified oil fraction to a methyl ester mixture that includes methyl 9-hexadecenoate. Fractional distillation at reduced pressure is used to isolate the desired product, methyl 9-hexadecenoate from other methyl esters.

Sulfonation of Unsaturated Fatty Acid Methyl Esters (UFAMEs): General Procedure A A sample of unsaturated fatty ester (e.g., 9-decylenic acid methyl ester), is added to methylene chloride in a small-scale batch sulfonation reactor fitted with a dry ice condenser and maintained at around 20° C. with a pre-established 2 L/m flow of $N_2$. Additional solvent is used as needed to reduce the viscosity of the reaction mixture. Over 30 min., sulfur trioxide is evaporated via a 140° C. flash-pot and bubbled through the reactor at a molar ratio of $SO_3$ to alkene functionality of about 1:1. The addition rate of $SO_3$ is adjusted to keep the reaction temperature at or below 35° C. When the reaction is complete, the mixture is held an additional 5 min., and excess solvent is removed under vacuum. The acid is then digested at 50° C. until no more β-sultones remained. Methanol (5 wt. %) is added to the acid, and the solution is warmed to 65° C. for 1 h. Total acidity is found by titration, and the acid is treated with an equimolar amount of 50% aq. NaOH and diluted with additional water to provide the desired actives level. Sultone hydrolysis is performed by warming the solution to 85° C. while maintaining pH=6 with additional charges of 50% aq. sodium hydroxide.

Esteramine Synthesis: General Procedure B

A tertiary alkanolamine (e.g. triethanolamine, N-methyldiethanolamine, N,N-dimethylethanolamine) or an alkoxylated derivative thereof is combined in the same reaction vessel with an ester derivative of 9-decylenic acid, 9-dodecylenic acid, or 9-octadecene-1,18-dioic acid and potassium carbonate. This mixture is heated with agitation at a temperature within the range of 150° C. to 200° C. The relative amounts of amine and ester (or acid) are balanced to provide the desired stoichiometry taking into account the ester/acid content determined by saponification number. The reaction is performed under nitrogen sparge or under vacuum to remove liberated alcohol. When glyceride esters of decylenic acid or dodecylenic acid are used, the liberated glycerin is not removed. The reaction is deemed complete when the desired residual amount of starting amine remains.

Quaternization: General Procedure C

Tertiary amines are converted to methyl quats, betaines, or sulfobetaines by reaction with a quaternizing agent. The quaternization is performed at temperature within the range of 65° C. to 100° C. The quaternizing agent used is dimethyl sulfate for methyl quats, sodium monochloroacetate for betaines, or epichlorohydrin for sulfobetaines. The amount of quaternizing agent used is from 0.8 to 1.0 molar equivalents based on the amount of tertiary amine. The reaction is deemed complete when the free amine value is in the desired range as determined by perchloric acid titration.

Amine Oxides from Amines: General Procedure D

A tertiary amine is diluted with water to form a 10-40 wt. % mixture, which is warmed to 50° C. to 75° C. under nitrogen. Hydrogen peroxide solution (35% solution, 1 to 2.2 molar eq.) is added dropwise while keeping the temperature below 75° C. The mixture is held at the reaction temperature for 4 to 12 h or until the free peroxide level is below 0.2% as determined by starch iodide paper.

Amide Synthesis (Including Amidoamines): General Procedure E

Unsaturated methyl ester ($C_{10}$, $C_{12}$, or $C_{16}$ monoester or $C_{18}$ diester) is combined with 1-6 molar equivalents of a primary or secondary amine (e.g., DMA, DEA, MEA, DMAPA). A base catalyst (e.g., NaOMe or other alkoxide) is added if desired. The reaction mixture is heated at a temperature within the range of 50° C. to 150° C. until the starting ester is substantially consumed. The amide product is purified by distillation, water washing, or other normal means. Alternatively, the product is used "as is" and converted to other derivatives.

Esterification to Make Ethoxylates (eFAMEs): General Procedure F

A suitable carboxylic acid is combined with a poly(ethylene glycol)monomethyl ether (0.8-2.5 eq.), an acid catalyst (e.g., sulfuric acid, methanesulfonic acid, p-toluenesulfonic acid, or the like), and optionally a solvent (e.g., toluene, xylene, or other hydrocarbons capable of forming a water azeotrope). The mixture is heated at 120° C. to 180° C. under vacuum, nitrogen sparge, or nitrogen blanket and the liberated water is collected. The reaction continues until the desired acid value is achieved.

Amines by Amide Reduction: General Procedure G

Lithium aluminum hydride (or a similar reducing agent) is dissolved in a solvent (e.g., diethyl ether, THF, dioxane, diglyme) under a nitrogen blanket. A suitable fatty amide is dissolved in the same solvent and is added dropwise, keeping the reaction temperature within the range of 25° C. to 50° C. After the addition, the mixture is stirred overnight at room temperature. Water is carefully added to quench the reaction, and aqueous sodium hydroxide is added. The solids are filtered off, and the solvent is removed. The amine product is purified by distillation.

Imidazoline Synthesis: General Procedure H

Methyl 9-decenoate or methyl 9-dodecenoate is combined with diethylenetriamine (DETA), with or without a catalyst, in the desired molar ratio of ester groups to primary amino and/or hydroxyl groups. Usually, two moles of ester are used for each mole of DETA. The mixture is heated with agitation to a temperature within the range of 140° C. and 200° C. under a mild vacuum that prevents or minimizes evaporation of DETA from the reaction mixture. The reaction proceeds until analysis (IR or $^1$H NMR spectroscopy) indicates reasonably complete conversion. The contents are then heated at a temperature within the range of 175° C. to 300° C. with a lower vacuum (5-100 mm Hg) to effect ring closure to the imidazoline. Reaction end point is determined by titration.

Sulfitation of Olefins: General Procedure J

A sulfitating agent (sodium sulfite, sodium bisulfite, sodium metabisulfite, or the like) is dissolved in water and combined with at least a molar equivalent of an olefin. Optionally, a catalyst (peroxides, iron, or other free-radical initiators) is included. The mixture is heated to 50° C.-100° C. for 3-15 h until sulfitation is reasonably complete.

Estolide Preparation: General Procedure K

The procedure used to convert methyl ester C10-0 to its respective fatty acid C10-36 is generally followed as described below.

Sulfonation is carried out in a batch reactor maintained at 20° C. under a nitrogen flow (2 L/min.). The unsaturated fatty acid or an unsaturated fatty acid and saturated fatty acid mixture is added to methylene chloride. Sulfur trioxide is evaporated over 30 min. via a 140° C. flash-pot and is bubbled through the reactor using the nitrogen stream at a molar ratio of $SO_3$ to alkene functionality of about 1:1. The addition rate of $SO_3$ is adjusted to keep the reaction temperature at or below 35° C. At the end of the addition, the reaction mixture is maintained for an additional 5 min. and the mixture is then concentrated under vacuum. The acid product is digested for 1-2 h at 50-85° C. Neutralization is performed using an appropriate base and hydrolysis occurs at 85° C. with the pH maintained with additional base. $^1$H NMR is used to determine complete hydrolysis.

Ester Hydrolysis to Fatty Acid: General Procedure L

The procedure used to make fatty acid C10-36 as outlined in detail below is generally used.

Tables 2A and 2B summarize the general procedures used to prepare the following compositions:

TABLE 2A

General Methods Used to Synthesize Compositions

| Composition | Methods |
|---|---|
| C10-0 | feed |
| C10-1 | A |
| C10-6 | B |
| C10-8 | F |
| C10-9 | F |
| C10-10 | F, J |
| C10-11* | F |
| C10-14 | H, C, J |
| C10-17* | E |
| C10-19* | E, C, J |
| C10-20 | E, D |
| C10-21 | E, D, J |
| C10-22 | E, C |
| C10-23 | E, C, J |
| C10-24* | E, C |
| C10-25* | E |
| C10-26 | E, J |
| C10-27 | E |
| C10-29 | F, J |
| C10-30 | F, J |
| C10-32* | K |
| C10-33* | K |
| C10-34 | K |
| C10-35 | K |
| C10-37 | E, J |
| C10-38 | E, G |
| C10-39 | E, G, D |
| C10-41 | E, G, C |
| C10-43* | E, G, C |
| C12-0 | feed |
| C12-1 | A1 |
| C12-4 | B |

TABLE 2A-continued

General Methods Used to Synthesize Compositions

| Composition | Methods |
|---|---|
| C12-6 | B |
| C12-8 | F |
| C12-9 | F |
| C12-10 | F, J |
| C12-11 | F |
| C12-14* | H, C, J |
| C12-19 | E, C, J |
| C12-20 | E, D |
| C12-21 | E, D, J |
| C12-22 | E, C |
| C12-23* | E, C, J |
| C12-24* | E, C |
| C12-25* | E |
| C12-26 | E, G |
| C12-28 | E, G, D |
| C12-29 | E, J |
| C12-31 | E |
| C12-32 | F, J |
| C12-33 | F, J |
| C12-34 | K |
| C12-35 | K |
| C12-36 | K |
| C12-37 | K |
| C12-39 | L |
| C12-40 | E, G, C |
| C12-42 | E, J |
| C12-43 | K |
| C12-44 | K |
| C12-46 | E, G, C |
| C12-47 | F |
| C12-48 | F |
| C12-49 | F |
| C16-0 | feed |
| C16-1 | A |
| C16-4 | B |
| C16-6 | B |
| C16-8 | F |
| C16-9 | E |
| C16-11 | E, J |
| C16-12 | E, D, J |
| C16-13 | E, C |
| C16-15 | E, G |
| C16-16 | E, G, C |

Methods:
A: UFAME sulfonation;
B: alkanolamine transesterification;
C: quaternization to methyl quat, betaine, or sulfobetaine;
D: oxidation of amine to amine oxide;
E: amide from unsaturated ester and primary or secondary amine;
F: ethoxylated fatty acid methyl ester from unsaturated fatty acid;
G: amine from amide by reduction;
H: imidazoline preparation from unsaturated ester + DETA;
J: sulfitation of olefins;
K: estolide preparation;
L: ester hydrolysis to the fatty acid or salt.
*A detailed procedure for synthesizing this composition is included hereinbelow.

TABLE 2B

General Methods Used to Synthesize Compositions

| Composition | Methods |
|---|---|
| C18-1 | A |
| Mix-2 | B |
| Mix-3 | B |
| Mix-5 | B |
| C18-9 | B |
| Mix-9 | B |
| Mix-11 | B |
| Mix-13 | B |

TABLE 2B-continued

General Methods Used to Synthesize Compositions

| Composition | Methods |
|---|---|
| Mix-15 | B |
| Mix-17 | F |
| Mix-18 | F |
| Mix-20 | F |
| Mix-23 | H, C, J |
| C18-28 | E, C, J |
| C18-29 | E, D |
| Mix-29 | E, D |
| C18-30 | E, D, J |
| C18-31 | E, C |
| Mix-31 | E, C |
| C18-32 | E, C |
| Mix-32 | E, C |
| C18-33 | E, C, J |
| C18-35 | E, C, D |
| Mix-35 | E, C, D |
| C18-36 | E, C |
| Mix-36 | E, C |
| C18-37 | E, C, D |
| Mix-37 | E, C, D |
| C18-38 | E, C |
| Mix-38 | E, C |
| Mix-42 | E |
| Mix-46 | E, D |
| Mix-48 | E, C |
| Mix-59 | E |
| Mix-61 | F, J |
| C18-63 | K |
| C18-64 | K |
| C18-68 | E, J |
| Mix-70 | E |
| Mix-73 | E, D |
| Mix-78 | E |
| PMTG-6 | E, C |
| PMTG-11 | E, C |
| PMTG-12 | E, D |
| PUTG-6 | E, C |
| PUTG-11 | E, C |
| PUTG-12 | E, D |
| MTG-6 | E, C |
| MTG-11 | E, C |
| MTG-12 | E, D |
| UTG-6 | E, C |
| UTG-7 | B, C |
| UTG-9 | B |
| UTG-11 | E, C |
| UTG-12 | E, D |
| UTG-15 | E |
| UTG-16 | E |

Methods:
A: UFAME sulfonation;
B: alkanolamine transesterification;
C: quaternization to methyl quat, betaine, or sulfobetaine;
D: oxidation of amine to amine oxide;
E: amide from unsaturated ester and primary or secondary amine;
F: ethoxylated fatty acid methyl ester from unsaturated fatty acid;
G: amine from amide by reduction;
H: imidazoline preparation from unsaturated ester + DETA;
J: sulfitation of olefins;
K: estolide preparation;
L: ester hydrolysis to the fatty acid or salt.

Each of the following compositions is tested as either an aqueous hard surface cleaner degreaser component or in a non-aqueous degreaser formulation. Unless otherwise indicated below, the compositions are prepared using the general methods summarized in Tables 2A and 2B:

C10-1: C10 Unsaturated Methyl Ester Sulfonate

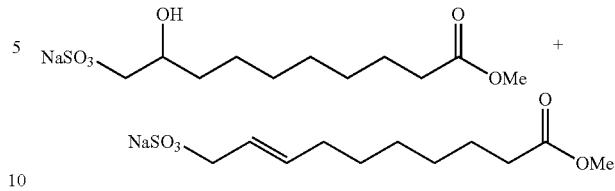

C10-6: C10 DMEA Ester

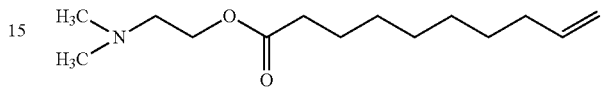

C10-8: C10 Ethoxylated Fatty Acid Methyl Ester ("eFAME")

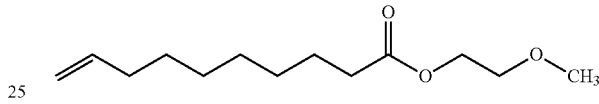

C10-9: C10 6EO eFAME

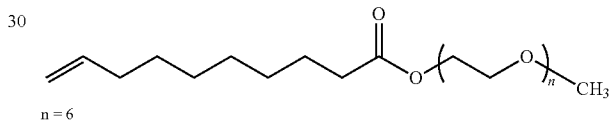

n = 6

C10-10: C10 6EO eFAME Sulfonate

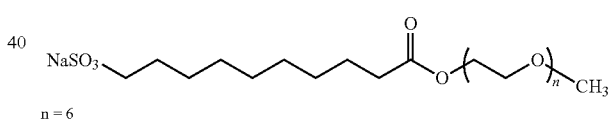

n = 6

C10-11: C10 24EO eFAME

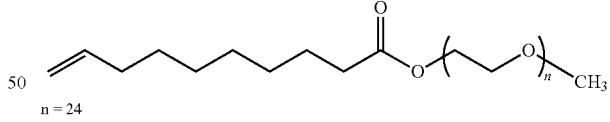

n = 24

Methyl ester C10-0 is converted to its respective fatty acid C10-36. A mixture of potassium hydroxide in glycerin (16-17 wt. %) is charged to a flask equipped with an overhead stirrer, thermocouple, and nitrogen sparge, and the solution is heated to 100° C. The methyl ester is then added. An excess of KOH (2 moles per mole of methyl ester) is used. The temperature is raised to 140° C. and heating continues until gas chromatography analysis indicates complete conversion. Deionized water is added give a weight ratio of product mixture to water of about 1.5. The solution is heated to 90° C. to melt any product that may have solidified. Aqueous sulfuric acid (30%) is added and mixed, and the layers are allowed to separate. The aqueous layer is drained. The fatty acid, C10-36, is washed with deionized water until the aqueous wash is neutral.

C10-36 fatty acid (45.0 g, 0.256 mol) is charged to a round-bottom flask equipped with an overhead stirrer, Dean-Stark trap, reflux condenser, thermocouple, heating mantle, and temperature controller. Polyethylene glycol monomethyl ether (267.0 g, 0.256 mol, an average of about 24 EO units per molecule) and toluene (500 mL) are added. The mixture is heated to 124° C. while p-toluenesulfonic acid (3.0 g) is added. Water of reaction begins to collect when the target temperature is reached. After heating 24 h, conversion (by GPC) is 97%. The sample is stripped to remove toluene. Residual toluene is removed by stirring at 150° C. under vacuum (1-5 mm Hg) with a low nitrogen sparge.

C10-14: C10 DETA Quat Sulfonate

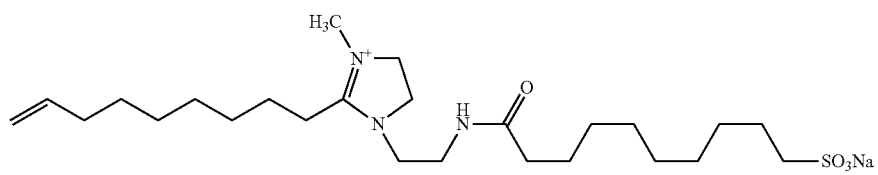

C10-17: C10 DMAPA Amide

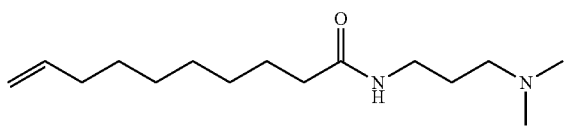 [SMILES: C=CCCCCCCCC(=O)NCCCN(C)C]

A round-bottom flask is charged with methyl ester C10-0 (500 g), DMAPA (331 g), and sodium methoxide/MeOH solution (0.5 wt. % sodium methoxide based on the amount of methyl ester). The contents are heated slowly to 140° C. and held for 6 h. The reaction mixture is vacuum stripped (110° C. to 150° C.). After cooling to room temperature, the product, C10-17, is analyzed. Amine value: 224.1 mg KOH/g; iodine value: 102.6 g $I_2$/100 g sample; titratable amines: 99.94%. $^1$H NMR (CDCl$_3$), δ (ppm): 5.75 (CH$_2$=CH—); 4.9 (CH$_2$=CH—); 3.3 (—C(O)—NH—CH$_2$—); 2.15 (—N(CH$_3$)$_2$).

C10-19: C10 DMAPA Quat Sulfonate

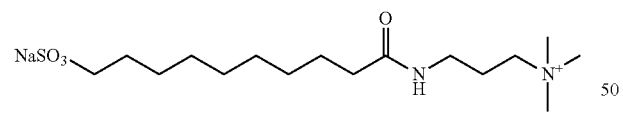

A flask equipped with condenser and nitrogen inlet is charged with amidoamine C10-17 (151.3 g). After warming to 80° C., dimethyl sulfate (68.38 g) is added dropwise. The temperature is raised to 85° C. and the mixture is stirred for 2 h. Isopropyl alcohol (23.45 g) is added, and the mixture stirs for 1 h. The product, C10-18, is analyzed: IPA: 7.72 wt. %; pH: 8.41 (1% in 9:1 IPA/water); iodine value: 56.8; tertiary amine: 0.020 meq/g; moisture: 1.7 wt. %; quaternary actives: 91.2 wt. %.

Methyl quat C10-18 (98.30 g) and water (216.3 g) are charged to a round-bottom flask equipped with stir bar, condenser, and thermocouple. The mixture is heated at 80° C. until homogeneous. Sodium metabisulfite (Na$_2$S$_2$O$_5$; 23.49 g, 1.03 eq. NaHSO$_3$) is added, and the mixture is held at 80° C. overnight. $^1$H NMR (D$_2$O) shows ~50% conversion to the sulfitated product. The mixture is held at 80° C. for 48 h and then reanalyzed; there are no significant changes. Sulfur dioxide is bubbled through the mixture, which is then held at 80° C. overnight, but there are still no significant changes in the NMR spectrum. The reaction stirs at room temperature over the weekend. The pH is adjusted to 6.6 and the mixture is heated at 80° C. overnight. NMR analysis shows that olefin peaks have diminished. The pH has dropped to 3 and is adjusted with caustic to 7. After heating for another 24 h, NMR analysis shows no more changes, with ~4-5% olefin remaining. Additional sodium metabisulfite (0.91 g, 0.04 eq. NaHSO$_3$) is added, and the reaction mixture is heated overnight. The $^1$H NMR spectrum indicates complete conversion to the desired quat sulfonate, C10-19. Analysis shows: moisture: 60.1%; Na$_2$SO$_4$: 1.93%.

C10-20: C10 DMAPA AO

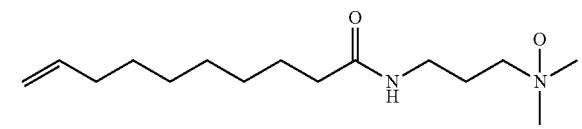

C10-21: C10 DMAPA AO Sulfonate

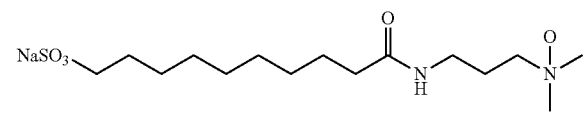

C10-22: C10 DMAPA Betaine

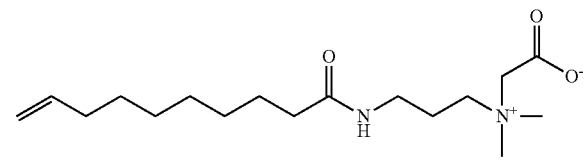 [SMILES: C=CCCCCCCCC(=O)NCCC[N+](C)(C)CC(=O)[O-]]

C10-23: C10 DMAPA Betaine Sulfonate

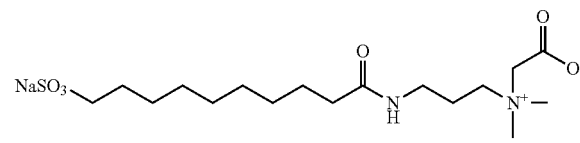

C10-24: C10 DMAPA Sulfobetaine

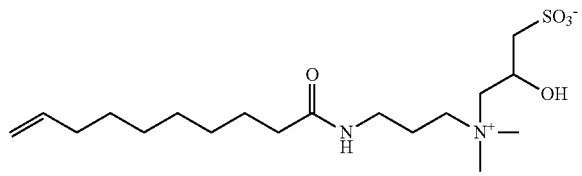

The procedure used to make sulfobetaine C10-43 (see below) is generally followed with amidoamine C10-17 (60 g), sodium metabisulfite (25.6 g), water (114 g), 50% aq. NaOH (two 0.3-g portions), and epichlorohydrin (24.4 g). Reaction continues at 75° C. for 3 h, and the pH (10% aqueous dilution) is kept between 8.2 and 8.9. After 3 h, the mixture cools to room temperature overnight. The mixture is reheated to 75° C. After 1 h, the pH has fallen to 8.1 and is increased with 50% NaOH (0.3 g). Reaction continues for 1 h. The reaction is judged complete when the NaCl level stabilizes at 6.55%. The mixture cools to room temperature, and the pH is adjusted to 6.95 with 50% $H_2SO_4$. The sulfobetaine product, C10-24, is analyzed: NaCl: 6.55 wt. %; solids: 51.8%; sulfobetaine actives (by solids-NaCl): 45.25%. $^1$H NMR analysis of a dried aliquot of the product mixture supports the proposed structure.

C10-25: C10 DMA Amide

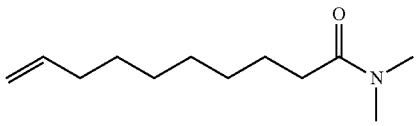

A round-bottom flask is charged with methyl ester feedstock C10-0 (235 g) and the mixture is degassed with nitrogen. Sodium methoxide (5 g of 30% solution in methanol) is added via syringe and the mixture is stirred for 5 min. Dimethylamine (67 g) is slowly added via sub-surface dip tube. After the addition, the mixture is heated to 60° C. and held overnight. The amide, C10-25, is recovered via vacuum distillation (120° C., 20 mm Hg). Yield: 241.2 g (96.3%). Iodine value=128.9 g $I_2$/100 g sample. $^1$H NMR (CDCl$_3$), δ (ppm)=5.8 (CH$_2$=CH—); 4.9 (CH$_2$=CH—); 2.8-3.0 (—C(O)—N(CH$_3$)$_2$); 2.25 (—CH$_2$—C(O)—). Ester content (by $^1$H NMR): 0.54%.

C10-26: C10 DMA Sulfonate

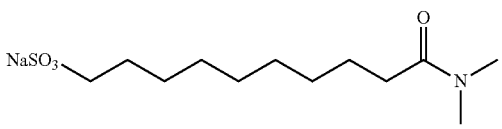

C10-27: C10 DEA Amide

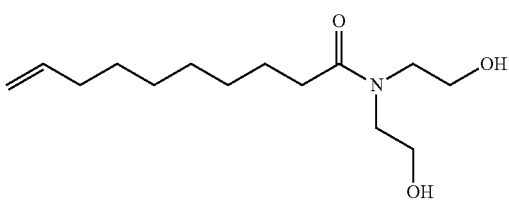 [SMILES: C=CCCCCCCCC(=O)N(CCO)CCO]

C10-29: C10 eFAME Sulfonate

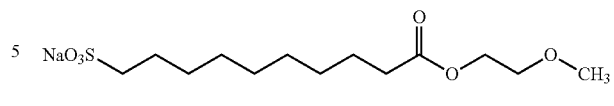

C10-30: C10 24EO eFAME Sulfonate

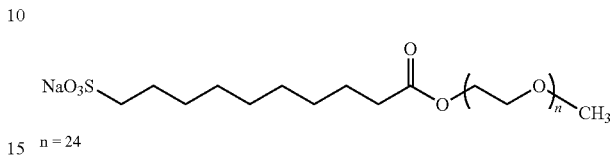

n = 24

C10-36: C10 Fatty Acid

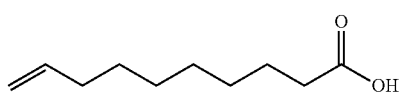

Methyl ester C10-0 (390.2 g) is charged to a round-bottom flask equipped with an overhead stirrer, and the contents are warmed to 70° C. Potassium hydroxide (16% solution in glycerin, 523 g) is added. The mixture is heated to 100° C. and additional KOH pellets (35.10 g) are added. After stirring 17 h, gas chromatography indicates ~94% conversion to the fatty acid. Additional KOH (10 g) is added, and stirring continues at 100° C. for 4 h. Conversion by GC is >97%. The mixture stirs at 100° C. for another 4 h, and is then cooled to 80° C. Water (400 mL) and 30% sulfuric acid solution (500 mL) are added, and the mixture stirs for 1 h. The aqueous phase is then removed. Water (500 mL) is added, and heating/stirring resumes (to 80° C.) for 0.5 h. The aqueous phase is again removed. The water washing process is repeated two more times (2×500 mL). The crude fatty acid product is stripped under vacuum at 80° C. for 2 h to remove water and is used without further purification. Yield: 357 g.

C10-32: C10 UFA SLA

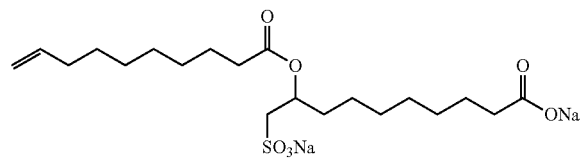

In a sulfonation batch reactor maintained at 20° C. under a nitrogen flow (2 L/min.), C10-36 (109.6 g, 0.64 mol) is added to methylene chloride (100 mL). Sulfur trioxide (51.6 g, 0.64 mol) is evaporated over 30 min. via a 140° C. flash-pot and is bubbled through the reactor using the nitrogen stream. The addition rate of SO$_3$ is adjusted to keep the reaction temperature at or below 35° C. At the end of the addition, the reaction mixture is maintained for an additional 5 min. and the mixture is then concentrated under vacuum. The acid product is then digested for 1 h at 50° C. The acid is neutralized using water (151.0 g) followed by 50% aq. NaOH (41.7 g). Hydrolysis is carried out at 85° C. and pH is maintained with additional 50% aq. NaOH additions. $^1$H NMR analysis supports the proposed composition for sulfo-estolide C10-32. Analytical results: pH: 5.25 (as is); moisture: 51.6 wt. %; sodium sulfate: 0.51 wt. %; unsulfonated matter: 0.79 wt. %.

C10-33: C10 UFA C18 FA (80:20) SLA

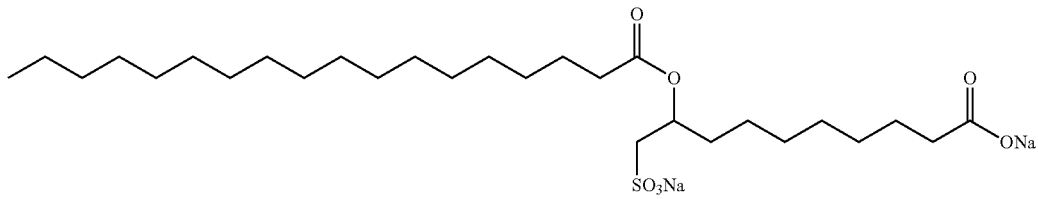

In a batch reactor maintained at 15° C. under a nitrogen flow (2 L/min.), an 80/20 (wt/wt) mixture of methyl 9-decenoate (C10-0) and stearic acid (115.3 g, 0.542 mol of unsaturation) is added to methylene chloride (300 mL). Sulfur trioxide (45.5 g, 0.569 mol) is evaporated over 30 min. via a 140° C. flash-pot and is bubbled through the reactor using the nitrogen stream. The addition rate of $SO_3$ is adjusted to keep the reaction temperature at or below 25° C. At the end of the addition, the reaction mixture is maintained for an additional 5 min. and the mixture is then concentrated under vacuum. The acid product is then digested for 1.5 h at 50° C. The acid product is neutralized using water (161.5 g) and 50% aq. NaOH (42.9 g). Hydrolysis is carried out at 85° C. Throughout the hydrolysis, a two-phase mixture is present. The mixture cools to room temperature and each phase is analyzed by $^1$H NMR. The product is allowed to concentrate in the open air for 2 days. The resulting paste is warmed to 75° C., homogenized by stirring, and cooled to room temperature. Analysis of the sulfo-estolide shows: pH: 7.89 (1% in 9:1 IPA/water); moisture: 23.7 wt. %; inorganic sulfate: 0.94 wt. %; unsulfonated matter: 10.5 wt. %. $^1$H NMR analysis supports the proposed composition.

C10-34: C10 UFA C10 FA (80:20) SLA

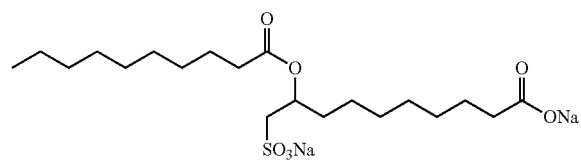

C10-35: C10 UME C10 FA (60:40) SLA

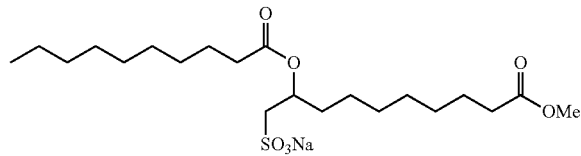

C10-37: C10 DMA Sulfonate (#2)

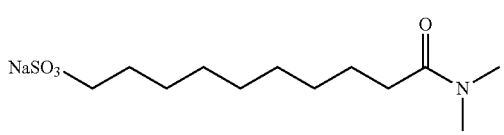

C10-38: C10 Amine

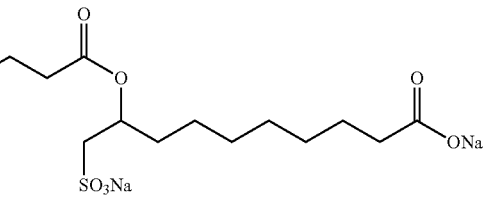

C10-39: C10 Amine Oxide

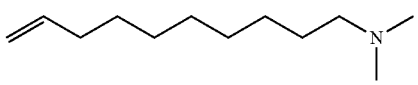

C10-41: C10 Betaine

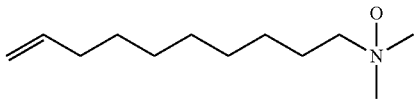

C10-43: C10 Amine Sulfobetaine

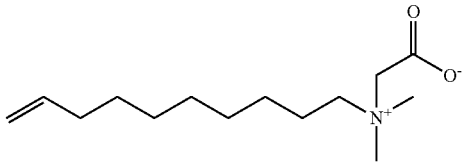 [SMILES: C=CCCCCCCCC[N+](C)(C)CC(=O)[O-]]

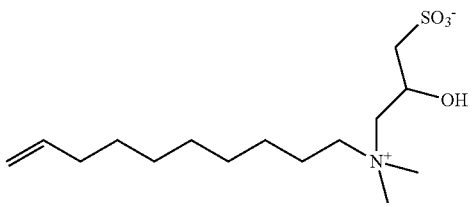

A flask equipped with nitrogen inlet is charged with sodium metabisulfite (50 g) and water (197 g), and the mixture is warmed to 40° C. Aqueous sodium hydroxide (0.6 g of 50% solution) is added. After stirring the mixture 5 min., epichlorohydrin (47.7 g) is added dropwise over 1 h, and the reaction exotherms to 70° C. The mixture is stirred at 70° C. for another 0.5 h. More aq. NaOH solution (0.6 g) is added and the mixture stirs briefly. Amine C10-38 (90 g) is added, and the temperature is increased to 90° C. After 1 h, the temperature is increased to 95° C. and held at 90-95° C. for 11.5 h. The pH is kept between 8.3 and 8.7 with 50% NaOH (aq) charges (2×1 g and 1×0.75 g). The reaction is judged complete when the NaCl level stabilizes at 7.60%. The mixture is cooled to give C10-43 as a clear solution (369.7 g). Analysis shows: pH: 7.53 (10% as is in DI water); NaCl: 7.82 wt. %; moisture: 48.8 wt. %. $^1$H NMR analysis supports the proposed structure (multiplet at ~4.7 for the methine proton, CH—OH).

C12-1: C12 Sulfonate

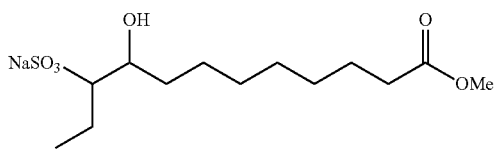

C12-11: C12 27EO eFAME

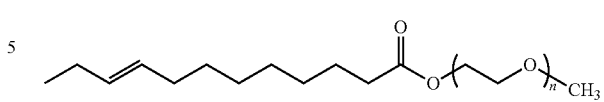

n = 27

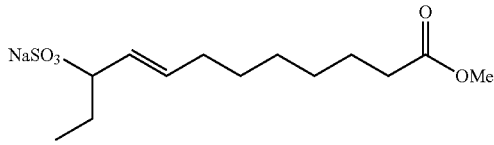

C12-14: C12 DETA Quat Sulfonate

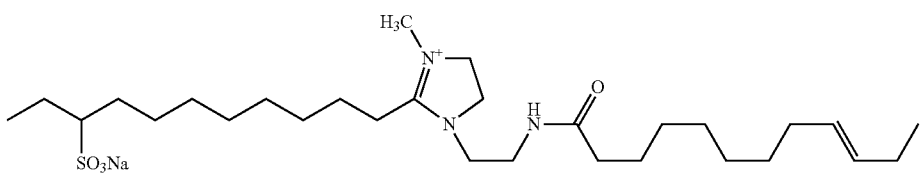

C12-4: C12 MDEA Ester

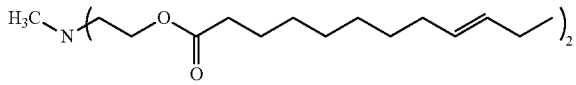

C12-6: C12 DMEA Ester

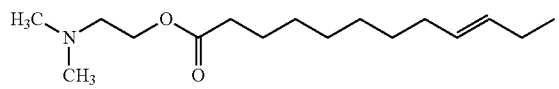 [SMILES: CC/C=C/CCCCCCCC(=O)OCCN(C)C]

C12-8: C10 eFAME

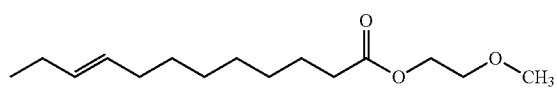 [SMILES: CC/C=C/CCCCCCCC(=O)OCCOC]

C12-9: C12 6EO eFAME

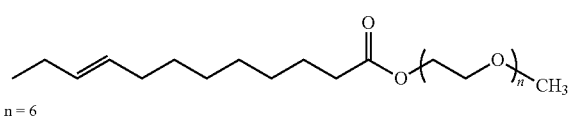

n = 6

C12-10: C12 6EO eFAME Sulfonate

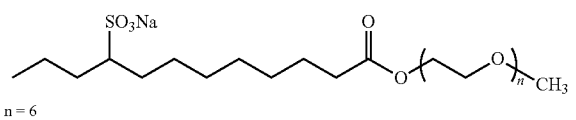

n = 6

Methyl 9-dodecenoate ("C12-0," 273.3 g), DABCO (0.3450 g), and DETA (66.48 g) are charged to a round-bottom flask, and the liquid mixture is sparged with nitrogen (175 mL/min). The mixture is heated from 100° C. to 170° C. over 2 h at atmospheric pressure. After 4.5 h at 170° C., a vacuum (90 mm Hg) is applied, and the mixture is heated for an additional 6 h. The resulting distillate (44.3 g) includes about 2 g of DETA. Additional DETA (2 g) is added to the reactor, and heating continues at 170° C. for 5 h at 400 mm Hg. The temperature is raised to 200° C. at improved vacuum (50 mm Hg). After 4 h, there is no distillate. p-Toluene-sulfonic acid is added (to induce ring closure to the imidazo-line, C12-12), and the mixture is reheated (200° C., 50 mm Hg) for 22 h. Analysis by titration shows that ring closure is 81%.

A flask equipped with condenser, nitrogen inlet, thermo-couple, and port for an addition flask is charged with imida-zoline C12-12 (212.1 g). The contents are heated to 80° C., and DMS (59.3 g) is added via the addition flask with a target perchloric acid titer (PAT) value of 0.065. The temperature is raised to 85° C., and stirring continues for 1 h. A sample is removed and titrated for PAT (found: 0.045). Isopropyl alco-hol (30.4 g) is added, and the mixture is stirred for 1 h. The product is DETA quat C12-13.

The C12 DETA quat (C12-13, 126.1 g), IPA (126.1 g), and t-butylperoxybenzoate (2.5 g) are charged to a round-bottom flask. The mixture is heated to 75° C. A solution of sodium metabisulfite (37.5 g), sodium sulfite (7.2 g), deionized water (190.0 g), and t-butylperoxybenzoate (1.2 g) is charged to an addition funnel, and then added dropwise to the reaction mixture, which is held at 75° C. for 16 h. IPA is removed via rotary evaporation. The $^1$H NMR spectrum suggests 75% conversion. Moisture content is adjusted to ~50% by adding water. (Note: the structure indicated above suggests single-site sulfonation, but the skilled person appreciates that at least some of the product with be the result of sulfonation at both carbon-carbon double bonds.)

C12-17: C12 DMAPA Amide

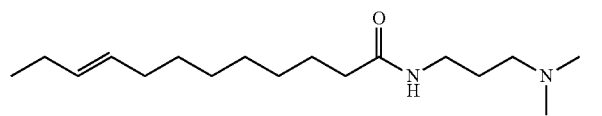 [SMILES: CC/C=C/CCCCCCCC(=O)NCCCN(C)C]

A round-bottom flask is charged with methyl 9-dodecenoate ("C12-0," 670 g). The mixture is stirred mechanically, and DMAPA (387 g) is added. A Dean-Stark trap is fitted to the reactor, and sodium methoxide (30 wt. % solution, 11.2 g) is added. The temperature is raised to 130° C. over 1.5 h, and methanol is collected. After 100 g of distillate is recovered, the temperature is raised to 140° C. and held for 3 h. $^1$H NMR shows complete reaction. The mixture is cooled to room temperature overnight. The mixture is then heated to 110° C. and DMAPA is recovered under vacuum. The temperature is slowly raised to 150° C. over 1.5 h and held at 150° C. for 1 h. The product, amidoamine C12-17, is cooled to room temperature. Amine value: 202.1 mg KOH/g; iodine value: 89.5 g $I_2$/100 g sample; free DMAPA: 0.43%; titratable amines; 100.3%. $^1$H NMR (CDCl$_3$), δ: 5.4 (—CH═CH—); 3.3 (—C(O)—NH—CH$_2$—); 2.2 (—N(CH$_3$)$_2$).

C12-19: C12 DMAPA Quat Sulfonate

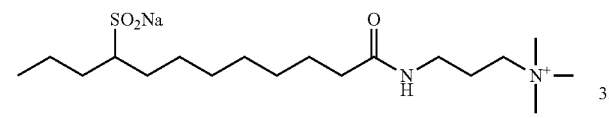

C12-20: C12 DMAPA AO

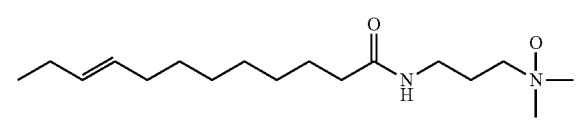

C12-21: C12 DMAPA AO Sulfonate

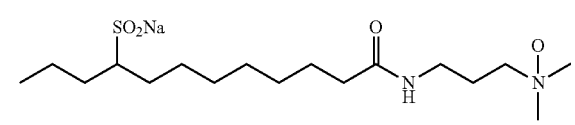

C12-22: C12 DMAPA Betaine

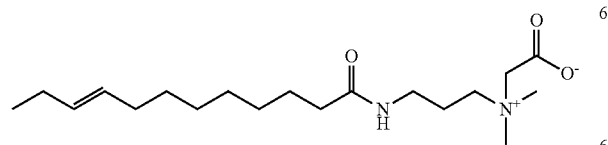

C12-23: C12 DMAPA Betaine Sulfonate

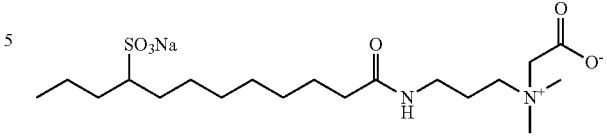

A round-bottom flask is charged with amidoamine C12-17 (210 g) and water (400 g). Sodium monochloroacetate (89 g) is added, and the mixture is heated to 80° C. The pH is maintained between 8 and 10 with 50% aq. NaOH (measuring pH as a 10% solution in water using pH strips). The temperature is raised to 100° C. and held for 4 h. The mixture is cooled to room temperature overnight. Water (100 g) is added to dilute the mixture, which is reheated to 100° C. for 4 h. Chloride titration shows 5.55% NaCl (expected 5.62%). The product, betaine C12-22, is cooled and analyzed: moisture: 62.13%; NaCl: 5.66%; free amine: 2.28%. $^1$H NMR (d$_4$-MeOH), δ: 5.4 (—CH═CH—); 3.8 (—C(O)—CH$_2$—N$^+$(CH$_3$)$_2$—); 3.2 (—C(O)—CH$_2$—N$^+$(CH$_3$)$_2$—).

Betaine C12-22 (284.6 g) is combined with water and sodium sulfite (33 mg). Air is bubbled through the solution at 0.5 mL/min. With stirring at room temperature, portions of sodium metabisulfite (5.99 g) are added every hour for 4 h, and the resulting solution stirs overnight. $^1$H NMR indicates 74% conversion. Additional sodium metabisulfite (2.39 g) is added, and the reaction is stirred overnight. $^1$H NMR shows 77% conversion. The product, sulfonate C12-23, is analyzed: moisture: 77.2%; Na$_2$SO$_4$: 1.6%; free bisulfite: 10 mg/L.

C12-24: C12 DMAPA Sulfobetaine

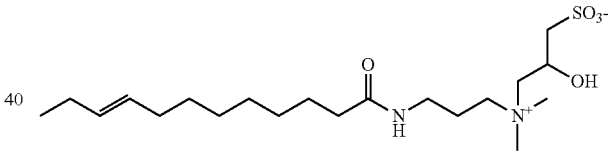

The procedure used to make sulfobetaine C10-24 is generally followed with amidoamine C12-17 (105 g), sodium metabisulfite (39.6 g), water (190 g), 50% aq. NaOH (two 0.6-g portions), and epichlorohydrin (37.8 g). Reaction continues at 80° C. for 3.5 h, and the pH (10% aqueous dilution) is kept between 8.2 and 8.6. After 3.5 h, the mixture cools to room temperature overnight. The mixture is reheated to 80° C. After 2 h, the pH is 8.5 and the NaCl level is 6.36%. The reaction is judged complete. The mixture cools to room temperature, and the pH is adjusted to 7.6 with 50% H$_2$SO$_4$. The sulfobetaine product, C12-24, is analyzed: NaCl: 6.34 wt. %; moisture: 49.7%; solids: 50.4%; sulfobetaine actives (by solids-NaCl): 44.0%. $^1$H NMR analysis of a dried aliquot of the product mixture supports the proposed structure.

C12-25: C12 DMA Amide

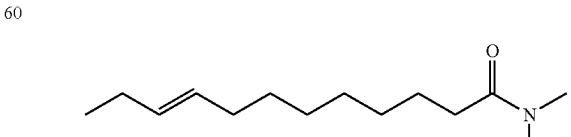

A round-bottom flask is charged with methyl ester feedstock C12-0 (900.0 g, 4.22 mol) and the material is heated to 60° C. The reactor is sealed and vacuum is applied for 0.5 h to dry/degas the feedstock. The reactor is backfilled with nitrogen, and then sodium methoxide (30 g of 30% solution in methanol) is added via syringe. A static vacuum (−30" Hg) is established, and then dimethylamine ("DMA," 190.3 g, 4.22 mol) is slowly added via sub-surface dip tube. When the pressure equalizes, the reactor is opened to nitrogen overhead and the temperature is increased 70° C. for 1.0 h. The reactor is then cooled to room temperature and the DMA addition is discontinued. Heating resumes to 80° C. and DMA is slowly introduced via sub-surface sparge and held for 2.0 h. The temperature is then increased to 90° C. and held for 1.0 h. $^1$H NMR spectroscopy indicates >98% conversion. The mixture is cooled to 75° C. and full vacuum is applied to strip methanol and excess DMA. The catalyst is quenched by adding 50% aqueous sulfuric acid (16.3 g) and the mixture is stirred vigorously for 10 min. Deionized water (200 mL) is added and all of the contents are transferred to a bottom-draining vessel. The aqueous layer is removed. The wash is repeated with 300 mL and then 150 mL of deionized water. Approximately 50 mL of 20% NaCl solution is added and the mixture settles overnight. The lower layer is removed and the product is transferred back to the reactor. The product is heated to 75° C. and vacuum is applied to remove residual water. The amide is recovered by vacuum distillation at 120° C. The amide fraction is placed under full vacuum at 135° C. until the ester content is below 1%. Final ester content: 0.7%. Yield: 875 g (91.9%).

C12-26: C12 Amine

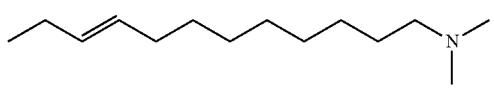

C12-28: C12 Amine Oxide

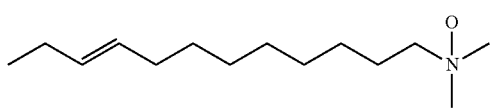

C12-29: C12 DMA Amide Sulfonate

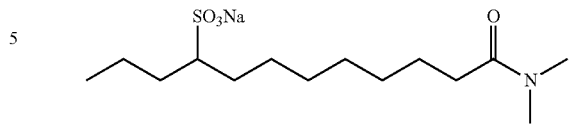

C12-31: C12 DEA Amide

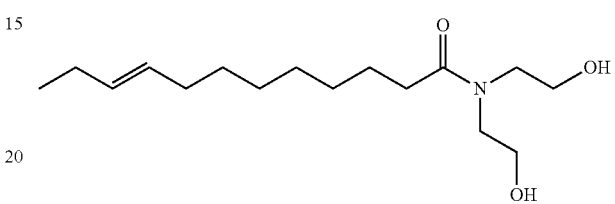

C12-32: C12 27EO eFAME Sulfonate

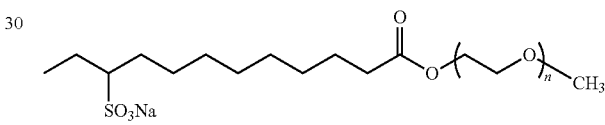

n = 27

C12-33: C12 eFAME Sulfonate

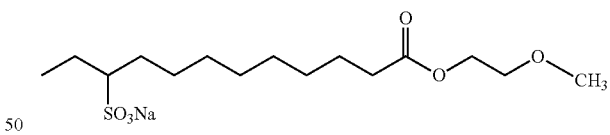

C12-34: C12 UFA SLA

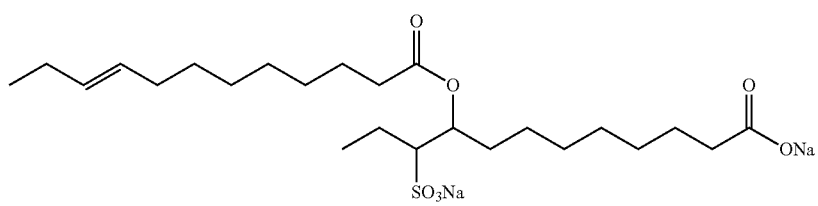

C12-35: C12 UFA C12 FA (80:20) SLA
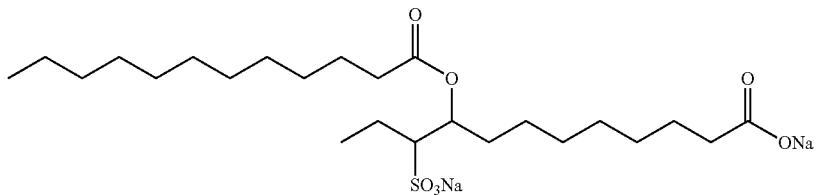
C12-36: C12 UFA C18 FA (80:20) SLA
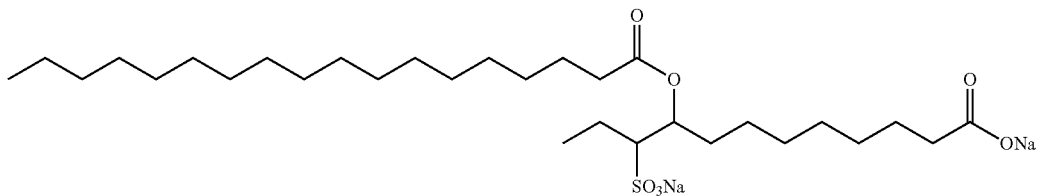
C12-37: C12 UME C12 FA (60:40) SLA
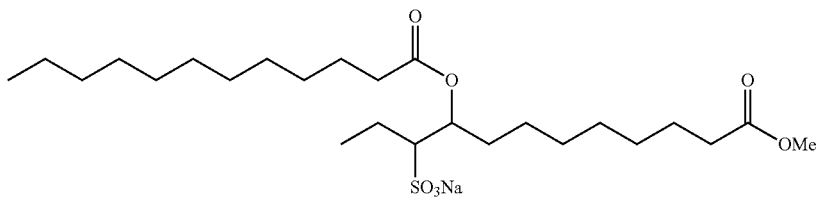
C12-39: C12 Fatty Acid
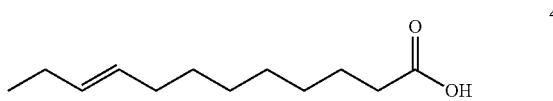
C12-40: C12 Betaine
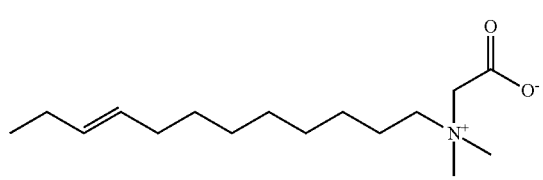 [SMILES: CC/C=C/CCCCCCCC[N+](C)(C)CC(=O)[O-]]
C12-42: C12 DMAPA Sulfonate
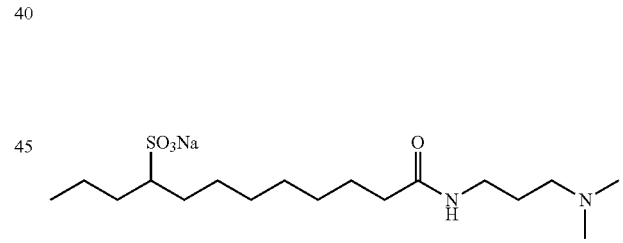
C12-43: C12 UFA C12 FA (80:20) SLA, Ca Salt
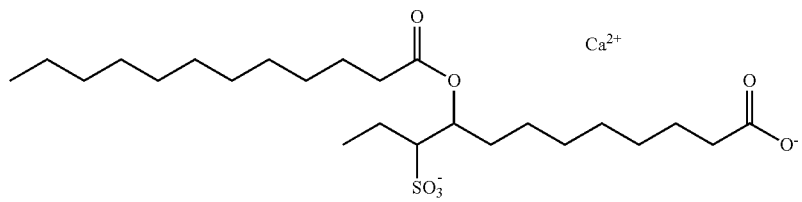

C12-44: C12 UFA C12 FA (80:20) SLA, TEA Salt
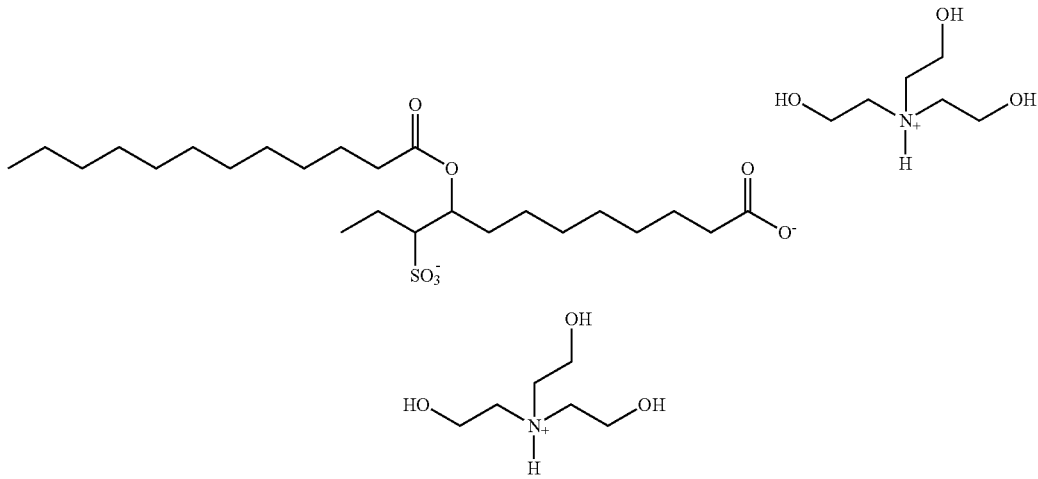
C12-46: C12 Sulfobetaine
C12-49: C12 15EO eFAME
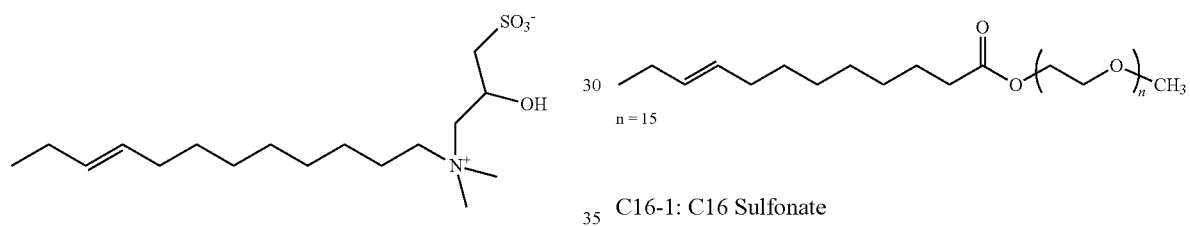
C12-47: C12 9EO eFAME
C16-1: C16 Sulfonate
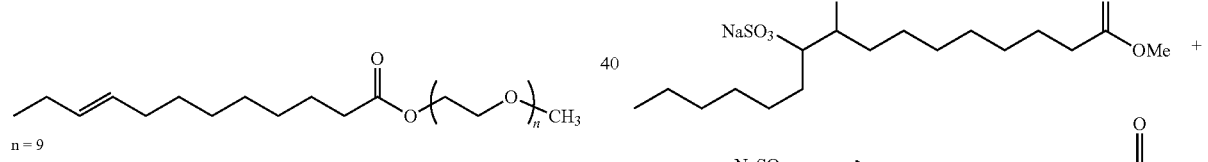
C12-48: C12 11EO eFAME
C16-4: C16 TEA Ester
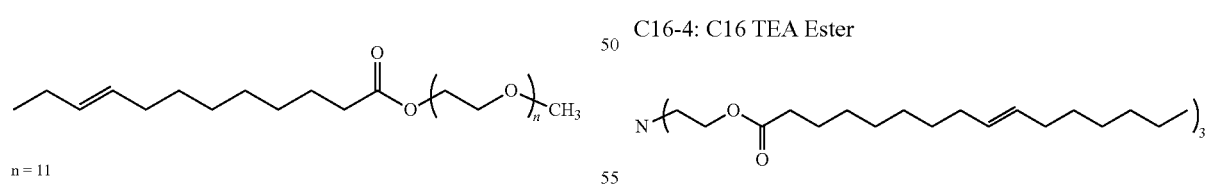
C16-6: C16 MDEA Ester
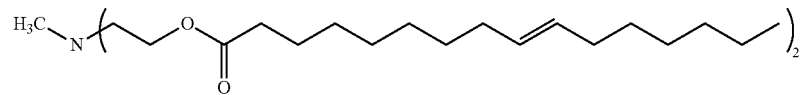

C16-8: C16 11EO eFAME
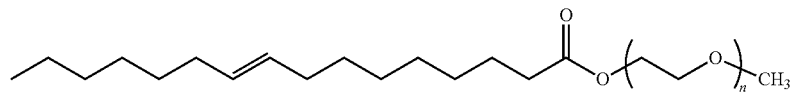
n = 11
C16-9: C16 DMAPA Amide
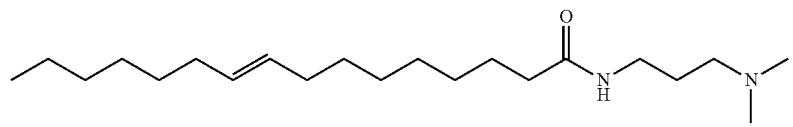 [SMILES: CCCCCC/C=C/CCCCCCCC(=O)NCCCN(C)C]
C16-11: C16 DMAPA Sulfonate
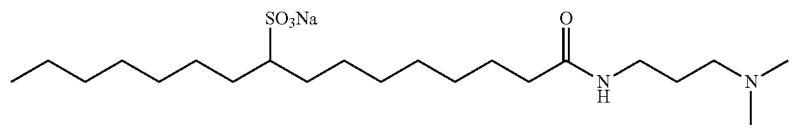
C16-12: C16 DMAPA Sulfonate AO
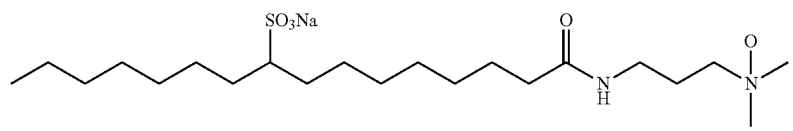
C16-13: C16 DMAPA Betaine
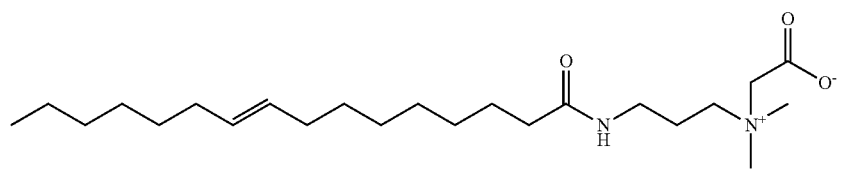 [SMILES: CCCCCC/C=C/CCCCCCCC(=O)NCCC[N+](C)(C)CC(=O)[O-]]
C16-15: C16 Amine
C16-16: C16 Betaine
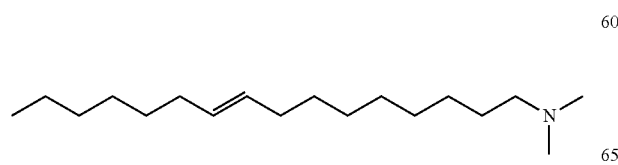
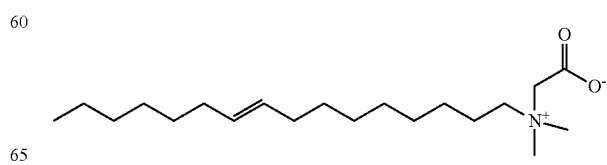

Feedstock Synthesis

Preparation of Dimethyl 9-Octadecene-1,18-dioate
("Mix-0" or "C18-0")

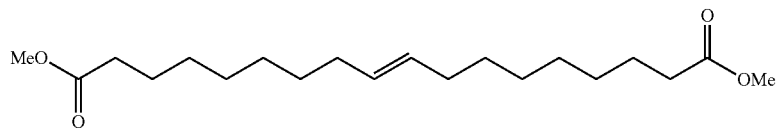 [SMILES: COC(=O)CCCCCCC/C=C/CCCCCCCC(=O)OC]

Eight samples of methyl 9-dodecenoate (10.6 g each, see Table 3) are warmed to 50° C. and degassed with argon for 30 min. A metathesis catalyst ([1,3-bis-(2,4,6-trimethylphenyl)-2-imidazolidinylidene]dichlororuthenium(3-methyl-2-butenylidene)-(tricyclohexylphosphine), product of Materia) is added to the methyl 9-dodecenoate (amount indicated in Table 3) and vacuum is applied to provide a pressure of <1 mm Hg. The reaction mixture is allowed to self-metathesize for the time reported. Analysis by gas chromatography indicates that dimethyl 9-octadecene-1,18-dioate is produced in the yields reported in Table 3. "Mix-0" is an 80:20 trans-/cis-isomer mixture obtained from the reaction mixture. Crystallization provides the all-trans-isomer feed, "C18-0."

TABLE 3

Self-Metathesis of Methyl 9-Dodecanoate

| Sample | Catalyst Loading (ppm mol/mol)* | Reaction Time (h) | C18-0 (GC Area %) |
|---|---|---|---|
| A | 100 | 3 | 83.5 |
| B | 50 | 3 | 82.5 |
| C | 25 | 3 | 83.0 |
| D | 10 | 3 | 66.2 |
| E | 15 | 4 | 90.0 |
| F | 13 | 4 | 89.9 |
| G | 10 | 4 | 81.1 |
| H | 5 | 4 | 50.9 |

*ppm mol catalyst/mol methyl 9-dodecenoate

The tested compounds based on $C_{18}$ feedstock have the following structures:

C18-1: C18 Sulfonate

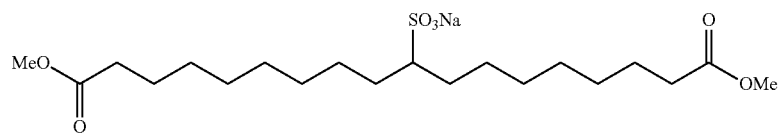

MIX-2: C18 diIPA Ester (80:20 Trans-/Cis-)

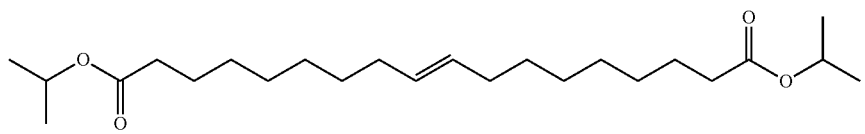 [SMILES: CC(C)OC(=O)CCCCCCC/C=C/CCCCCCCC(=O)OC(C)C]

MIX-3: C18 TEA Ester (2:1) Mix (80:20 Trans-/Cis-)

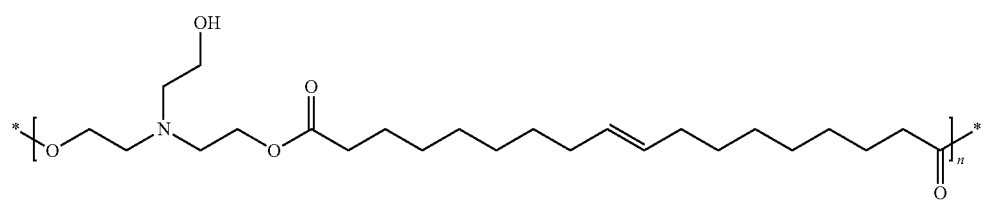

MIX-5: C18 TEA Ester (1:1) Mix (80:20 Trans-/Cis-)
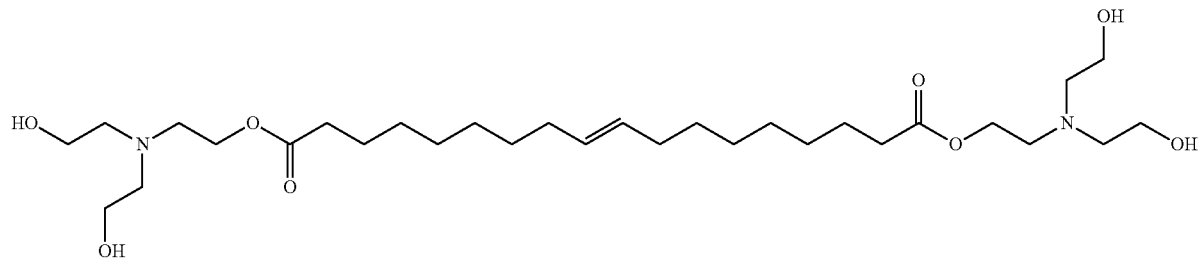 [SMILES: O=C(CCCCCCC/C=C/CCCCCCCC(=O)OCCN(CCO)CCO)OCCN(CCO)CCO]
C18-9: C18 MDEA Ester (2:1) Mix (100% Trans-)
MIX-9: C18 MDEA Ester (2:1) Mix (80:20 Trans-/Cis-)
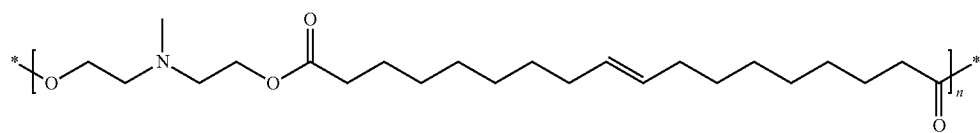
MIX-11: C18 MDEA Ester (1:1) Mix (80:20 Trans-/Cis-)
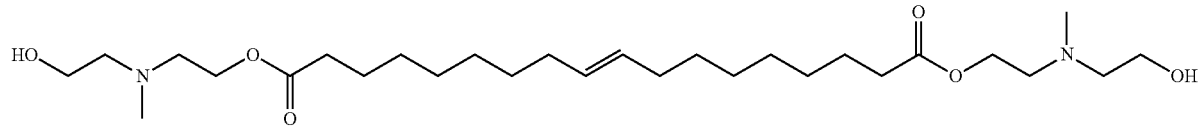 [SMILES: CN(CCO)CCOC(=O)CCCCCCC/C=C/CCCCCCCC(=O)OCCN(C)CCO]
MIX-13: C18 MDEA Ester (3:1) Mix (80:20 Trans-/Cis-)
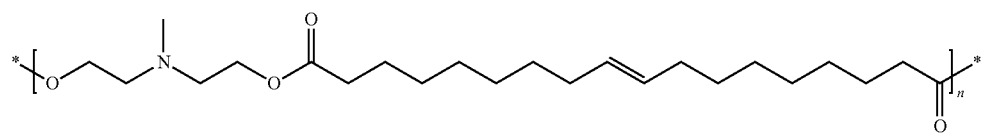
+
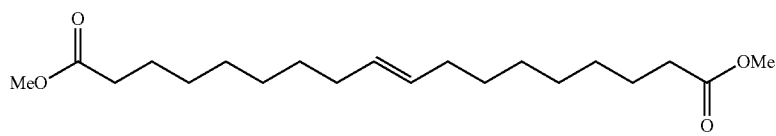
MIX-15: C18 diDMEA Ester (80:20 Trans-/Cis-)
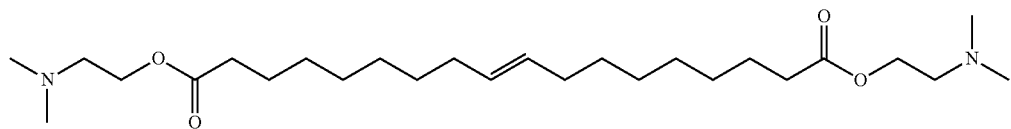

MIX-17: C18 eFAME (80:20 Trans-/Cis-)
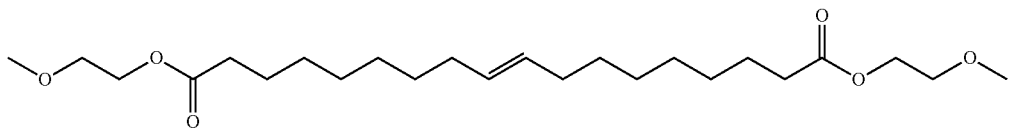
MIX-18: C18 eFAME (80:20 Trans-/Cis-)
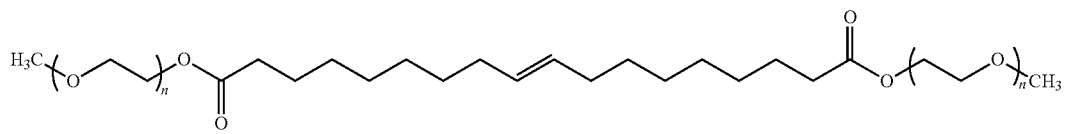
MIX-20: C18 eFAME (80:20 Trans-/Cis-)
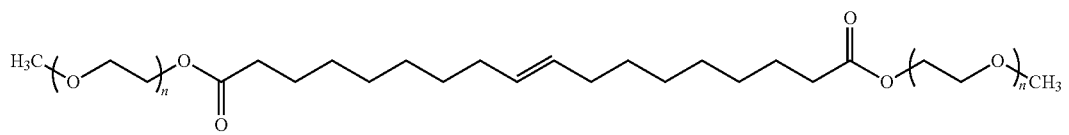
n = 24
MIX-23: C18 diDETA diQuat Sulfonate
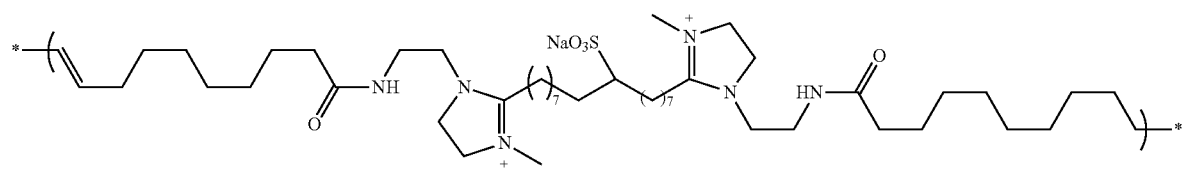
C18-28: C18 DiDMAPA diQuat Sulfonate
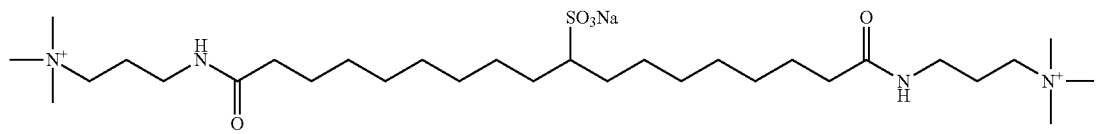
C18-29: C18 DiDMAPA DiAO (100% Trans-)
MIX-29: C18 DiDMAPA DiAO (80:20 Trans-/Cis-)
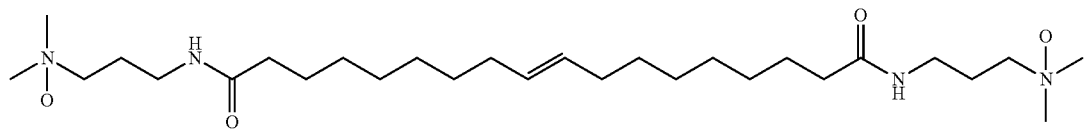

C18-30: C18 DiDMAPA DiAO Sulfonate
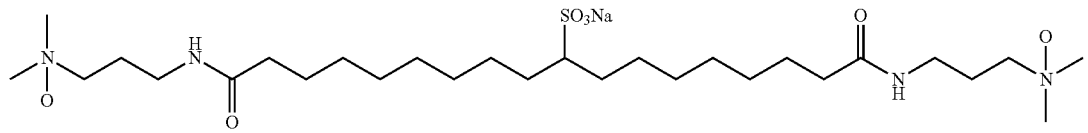
C18-31: C18 DiDMAPA DiSulfobetaine (100% Trans-)
MIX-31: C18 DiDMAPA DiSulfobetaine (80:20 Trans-/Cis-)
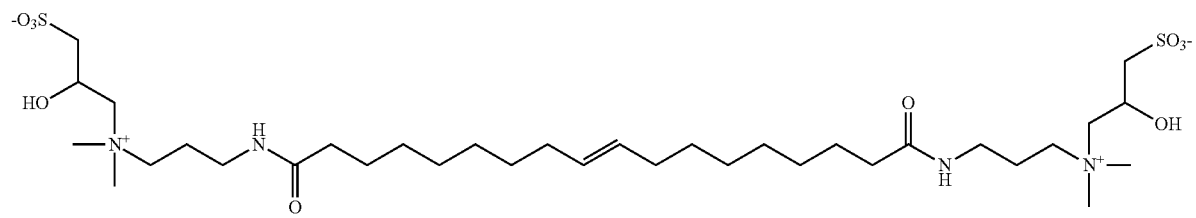
C18-32: C18 DiDMAPA DiBetaine (100% Trans-)
MIX-32: C18 DiDMAPA DiBetaine (80:20 Trans-/Cis-)
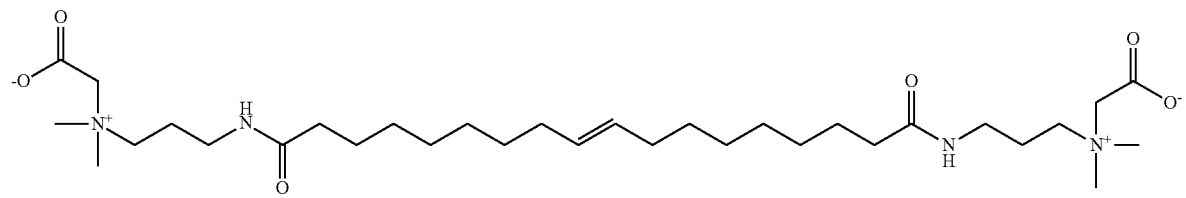
C18-33: C18 DiDMAPA DiBetaine Sulfonate
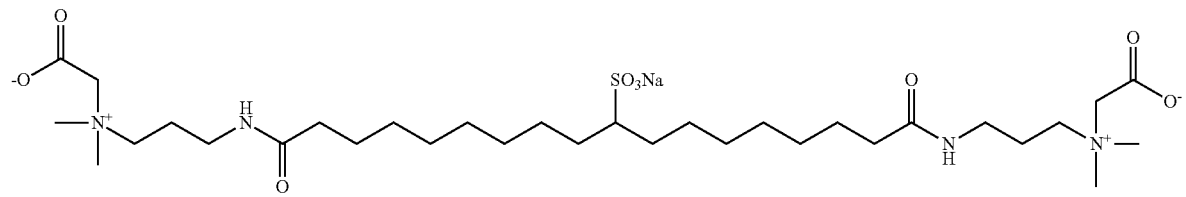
C18-35: C18 DiDMAPA Quat AO (100% Trans-)
MIX-35: C18 DiDMAPA Quat AO (80:20 Trans-/Cis-)
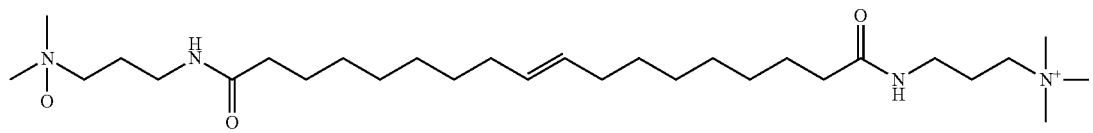

C18-36: C18 DiDMAPA Monobetaine (100% Trans-)
MIX-36: C18 DiDMAPA Monobetaine (80:20 Trans-/Cis-)
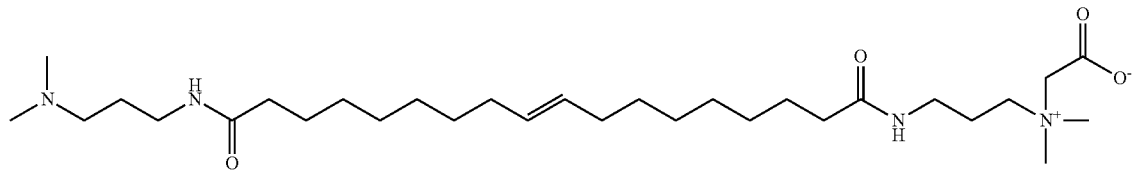 [SMILES: CN(C)CCCNC(=O)CCCCCCC/C=C/CCCCCCCC(=O)NCCC[N+](C)(C)CC(=O)[O-]]
C18-37: C18 DiDMAPA Betaine AO (100% Trans-)
MIX-37: C18 DiDMAPA Betaine AO (80:20 Trans-/Cis-)
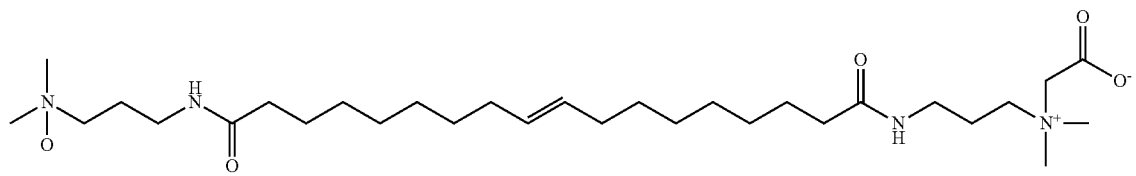
C18-38: C18 DiDMAPA Betaine Quat (100% Trans-)
MIX-38: C18 DiDMAPA Betaine Quat (80:20 Trans-/Cis-)
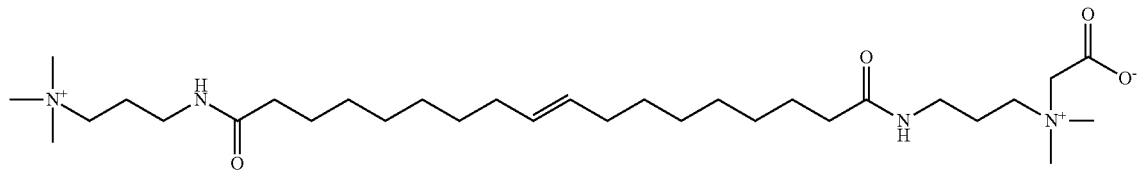 [SMILES: C[N+](C)(C)CCCNC(=O)CCCCCCC/C=C/CCCCCCCC(=O)NCCC[N+](C)(C)CC(=O)[O-]]
MIX-42: C18 DiDEA Amide (80:20 Trans-/Cis-)
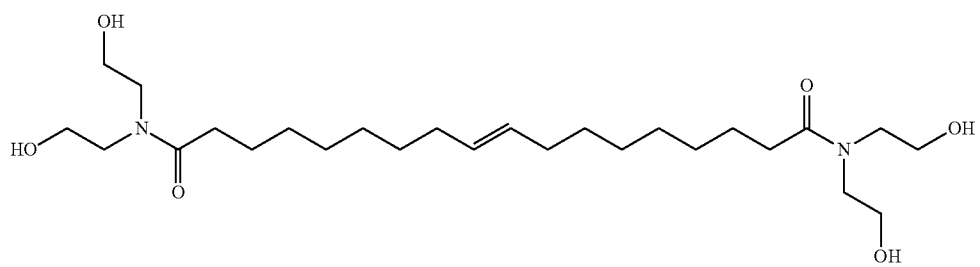 [SMILES: O=C(CCCCCCC/C=C/CCCCCCCC(=O)N(CCO)CCO)N(CCO)CCO]
MIX-46: C18 Ester DMAPA AO (80:20 Trans-/Cis-)
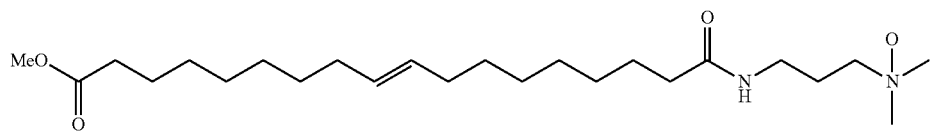

MIX-48: C18 Ester DMAPA Betaine (80:20 Trans-/Cis-)
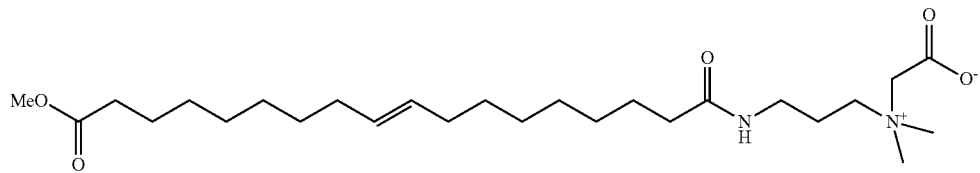 [SMILES: COC(=O)CCCCCCC/C=C/CCCCCCCC(=O)NCCC[N+](C)(C)CC(=O)[O-]]
MIX-59: C18 Ester DMA (80:20 Trans-/Cis-)
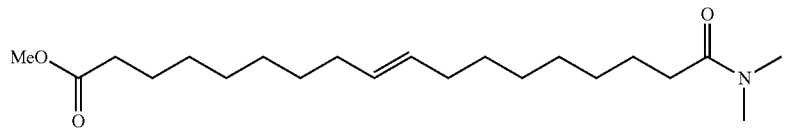 [SMILES: COC(=O)CCCCCCC/C=C/CCCCCCCC(=O)N(C)C]
MIX-61: C18 eFAME Sulfonate
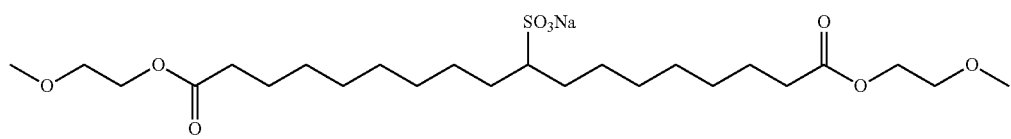
C18-63: DBE C10 FA (60:40) SLA
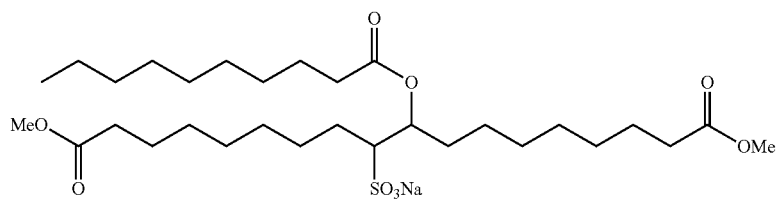
C18-64: DBE C10 FA (75:25) SLA
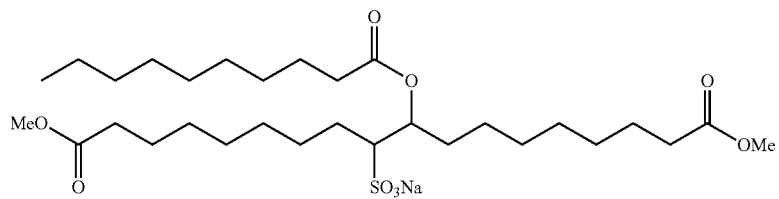
C18-68: C18 DiDMAPA Amide Sulfonate
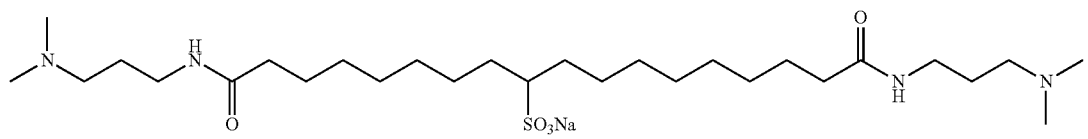

MIX-70: C18 DMAPA Carboxylate (80:20 Trans-/Cis-)

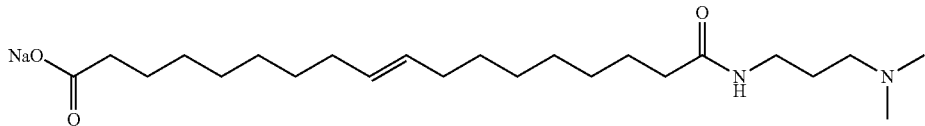

MIX-73: C18 Carboxylate DMAPA AO (80:20 Trans-/Cis-)

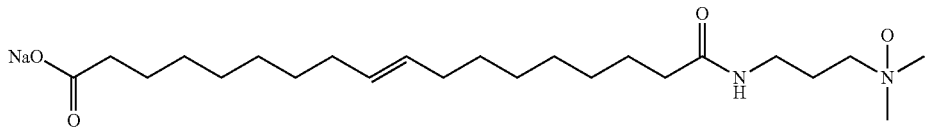

MIX-78: C18 Carboxylate DMA Amide (80:20 Trans-/Cis-)

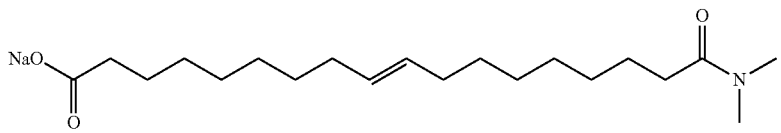

Modified Triglyceride Based on Soybean Oil ("MTG-0")

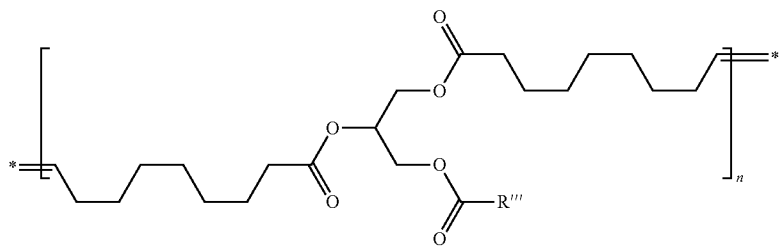

The procedures of Examples 1A and 1E are generally followed except that 1-butene is omitted.

Mod. Triglyceride from Cross-Metathesis of Soybean Oil and 1-Butene ("UTG-0")

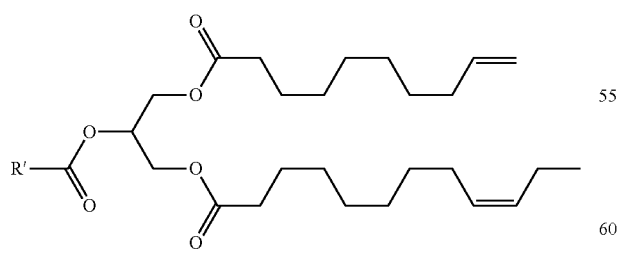

Unsaturated Triglycerides
(C10 and C12 enriched, also containing
C16 and C18 Saturates)

The procedures of Examples 1A and 1E are generally followed to produce UTG-0 from soybean oil and 1-butene.

Modified Triglyceride Based on Palm Oil ("PMTG-0")

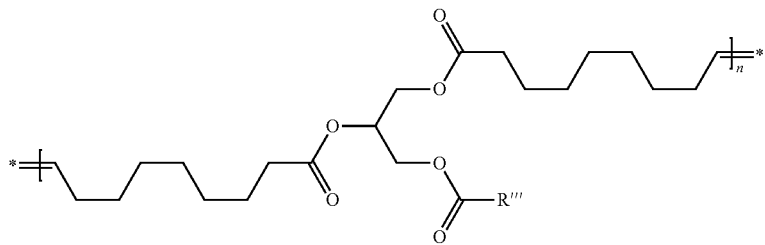

The procedure used to make MTG-0 is followed, except that palm oil is used instead of soybean oil.

Mod. Triglyceride from Cross-Metathesis of Palm Oil and 1-Butene ("PUTG-0")

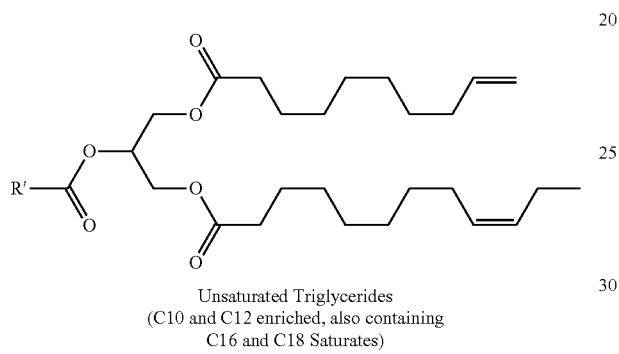

Unsaturated Triglycerides
(C10 and C12 enriched, also containing
C16 and C18 Saturates)

The procedure used to make UTG-0 is followed, except that palm oil is used instead of soybean oil.

MTG-0 Feedstock Derivatives

MTG-6: MTG DMAPA Betaine Mix

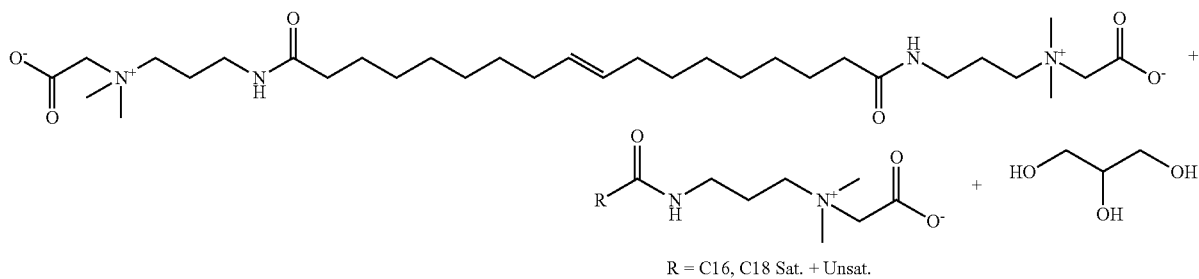

R = C16, C18 Sat. + Unsat.

MTG-11: MTG DMAPA Sulfobetaine

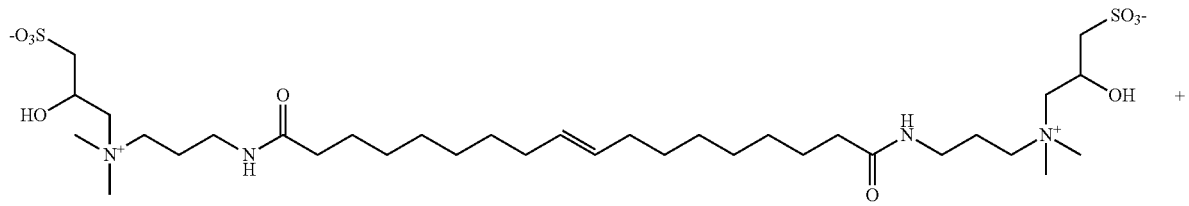

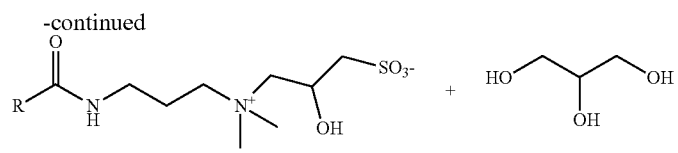

R = C16, C18 Sat. + Unsat.

MTG-12: MTG DMAPA AO

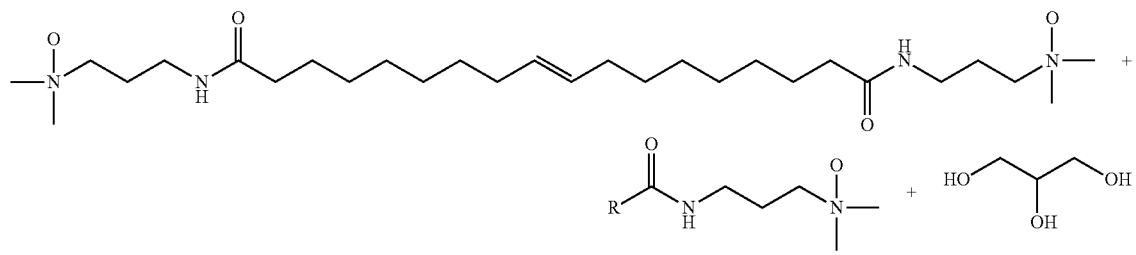

R = C16, C18 Sat. + Unsat.

Analogous procedures are used to make the corresponding products starting from PMTG-0, UTG-0, and PUTG-0. The products from modified triglycerides are summarized below in Table 4.

The PMTG products have analogous structures to the MTG products. The PUTG products have structures as shown below, with the UTG products having structures analogous to the PUTG products.

PUTG-6: PUTG DMAPA Betaine Mix

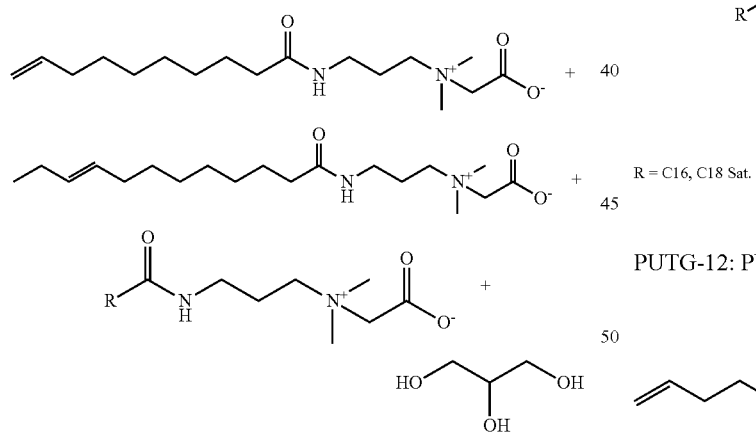

R = C16, C18 Sat.

PUTG-11: PUTG DMAPA Sulfobetaine

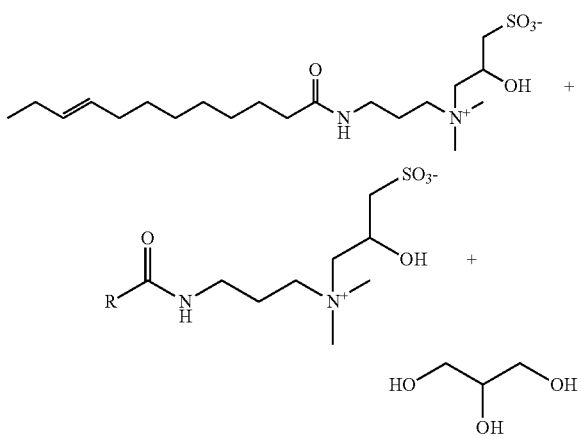

R = C16, C18 Sat.

PUTG-12: PUTG DMAPA AO

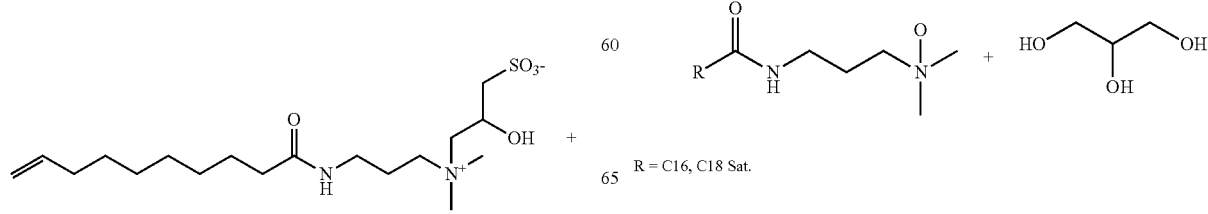

R = C16, C18 Sat.

UTG-7: UTG TEA Ester (1:1) Quat

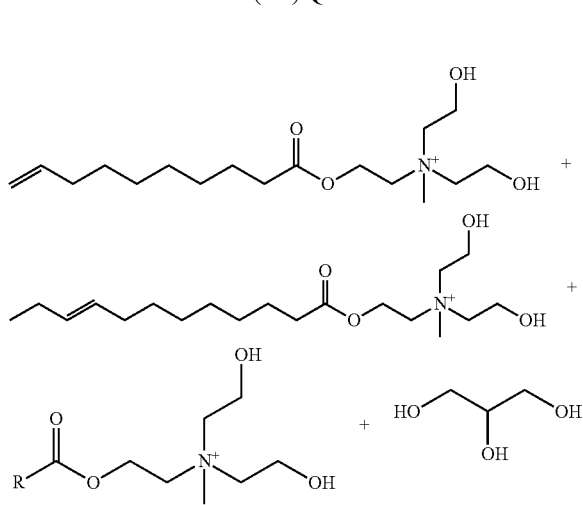

R = C16, C18 Sat. + Unsat.

UTG-9: UTG MDEA Ester (2:1)

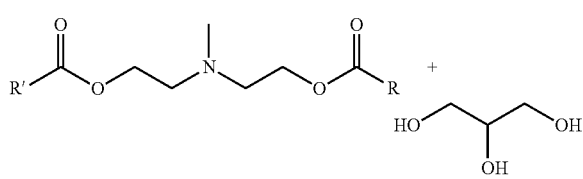

R = C10, C12-C18 Sat. and Unsat.
R' = C10, C12-C18 Sat. and Unsat.

UTG-15: UTG DMA Amide

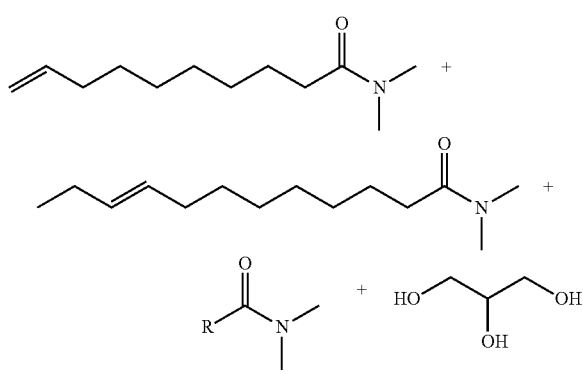

R = C16, C18 Sat.

UTG-16: UTG DEA Amide

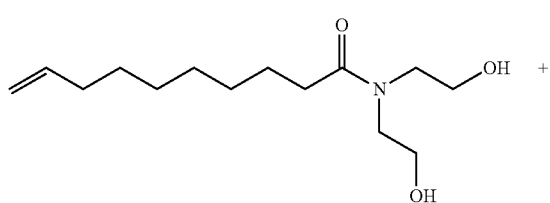

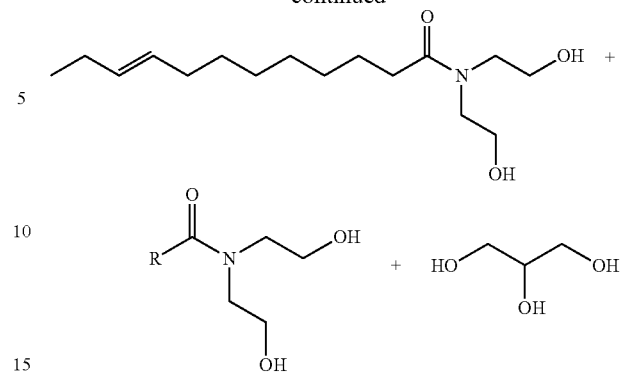

R = C16, C18 Sat.

The procedure used to make UTG-15 is generally followed except that diethanolamine is used instead of dimethylamine.

TABLE 4

Summary of Modified Triglyceride Products

|  | Soybean Oil | | Palm Oil | |
| --- | --- | --- | --- | --- |
|  | Self-met. MTG-0 | X-met. UTG-0 | Self-met. PMTG-0 | X-met. PUTG-0 |
| DMAPA Betaine Mix | MTG-6 | UTG-6 | PMTG-6 | PUTG-6 |
| DMAPA Sulfobetaine | MTG-11 | UTG-11 | PMTG-11 | PUTG-11 |
| DMAPA AO | MTG-12 | UTG-12 | PMTG-12 | PUTG-12 |
| UTG MDEA ester (2:1) |  | UTG-9 |  |  |
| UTG DMA amide |  | UTG-15 |  |  |
| UTG DEA amide |  | UTG-16 |  |  |
| UTG TEA ester quat |  | UTG-7 |  |  |

Hard-Surface Cleaners: Aqueous Degreasers

This test measures the ability of a cleaning product to remove a greasy dirt soil from a white vinyl tile. The test is automated and uses an industry standard Gardner Straight Line Washability Apparatus. A camera and controlled lighting are used to take a live video of the cleaning process. The machine uses a sponge wetted with a known amount of test product. As the machine wipes the sponge across the soiled tile, the video records the result, from which a cleaning percentage can be determined. A total of 10 strokes are made using test formulation diluted 1:32 with water, and cleaning is calculated for each of strokes 1-10 to provide a profile of the cleaning efficiency of the product. The test sample is used as a component of different control formulations depending on whether it anionic, amphoteric, or nonionic.

Anionic Test Samples:

A neutral, dilutable all-purpose cleaner is prepared from propylene glycol n-propyl ether (4.0 g), butyl carbitol (4.0 g), sodium citrate (4.0 g), Bio-Soft® EC-690 ethoxylated alcohol (1.0 g, product of Stepan), test sample (0.29 g if 100% active material), and deionized water (to 100.0 g solution). The control sample for anionic testing replaces the test sample with Stepanol® WA-Extra PCK (sodium lauryl sulfate, Stepan, 1.0 g, nominally 30% active).

Nonionic and Amphoteric Test Samples:

A neutral, dilutable all-purpose cleaner is prepared from propylene glycol n-propyl ether (4.0 g), butyl carbitol (4.0 g), sodium citrate (4.0 g), Stepanol WA-Extra PCK (sodium lauryl sulfate, 1.0 g), test sample (0.90 g if 100% active material), and deionized water (to 100.0 g solution). The control sample for nonionic/amphoteric testing replaces the test sample with Bio-Soft EC690 (ethoxylated alcohol, 1.0 g, nominally 90% active material).

Soil Composition (from Gardner ASTM D4488-95 Method):

Tiles are soiled with a particulate medium (50 mg) and an oil medium (5 drops). The particulate medium is composed of (in parts by weight) hyperhumus (39), paraffin oil (1), used motor oil (1.5), Portland cement (17.7), silica 1 (8), molacca black (1.5), iron oxide (0.3), bandy black clay (18), stearic acid (2), and oleic acid (2). The oil medium is composed of kerosene (12), Stoddard solvent (12), paraffin oil (1), SAE-10 motor oil (1), Crisco® shortening, product of J.M. Smucker Co. (1), olive oil (3), linoleic acid (3), and squalene (3).

TABLE 5

Control Runs for Gardner Straight Line Washability Test

Ave. % clean after 2, 4, 6, 8, or 10 swipes

|  | 2 | 4 | 6 | 8 | 10 |
|---|---|---|---|---|---|
| Control 1 | 52.4 | 59.0 | 62.5 | 62.8 | 63.9 |
| Control 2 | 47.0 | 57.3 | 61.0 | 63.7 | 65.2 |
| Control 3 | 54.6 | 61.4 | 64.3 | 68.4 | 72.2 |
| Control 4 | 52.5 | 58.2 | 59.5 | 60.9 | 63.3 |
| Control 5 | 50.8 | 59.2 | 63.9 | 65.3 | 67.1 |

TABLE 5-continued

Control Runs for Gardner Straight Line Washability Test

Ave. % clean after 2, 4, 6, 8, or 10 swipes

|  | 2 | 4 | 6 | 8 | 10 |
|---|---|---|---|---|---|
| Control 6 | 51.2 | 57.6 | 62.7 | 62.6 | 66.0 |
| Control 7 | 52.3 | 56.0 | 61.5 | 64.3 | 65.0 |
| Control 8 | 49.6 | 55.9 | 56.8 | 62.8 | 64.1 |
| Control 9 | 55.5 | 61.5 | 66.0 | 65.9 | 68.4 |
| Control 10 | 60.3 | 63.5 | 66.2 | 65.8 | 68.7 |
| Control 11 | 53.0 | 61.0 | 63.6 | 64.6 | 66.2 |
| Control 12 | 65.6 | 71.4 | 75.0 | 75.3 | 72.6 |
| Control 13 | 67.6 | 72.6 | 76.0 | 76.3 | 76.5 |
| Control 14 | 61.2 | 65.5 | 67.7 | 69.1 | 69.7 |
| Control 15 | 59.7 | 63.6 | 64.5 | 69.5 | 69.5 |
| Control 16 | 50.9 | 61.5 | 63.1 | 64.0 | 67.7 |
| Control 17 | 54.7 | 63.7 | 64.6 | 66.1 | 69.6 |
| Control 18 | 62.2 | 67.6 | 70.4 | 71.7 | 71.7 |
| Control 19 | 60.8 | 68.0 | 70.6 | 71.4 | 71.5 |
| Control 20 | 65.0 | 70.7 | 72.2 | 73.7 | 74.0 |
| Control 21 | 64.6 | 68.8 | 70.5 | 71.2 | 72.0 |
| Control 22 | 51.3 | 57.7 | 61.5 | 64.1 | 68.0 |
| Control 23 | 60.2 | 64.7 | 66.7 | 68.3 | 68.7 |
| Control 24 | 52.8 | 61.6 | 63.3 | 64.9 | 65.7 |

TABLE 6

Nonionic/Amphoteric Test Samples: Inventive Examples

| Sample | Con. # | Compound class | Ave. % clean 2 | 4 | 6 | 8 | 10 | Rating |
|---|---|---|---|---|---|---|---|---|
| C10-11 | 1 | high-EO ethoxylate | 57.7 | 64.8 | 70.2 | 70.5 | 71.9 | superior |
| C10-19 | 2 | DMAPA quat sulfonate | 55.2 | 62.0 | 65.5 | 66.9 | 67.8 | superior |
| C12-14 | 1 | DETA quat sulfonate | 58.0 | 65.7 | 68.5 | 69.0 | 69.4 | superior |
| C12-24 | 3 | DMAPA sulfobetaine | 64.2 | 70.6 | 72.3 | 76.6 | 80.2 | superior |
| UTG-11 | 4 | DMAPA sulfobetaine | 63.3 | 65.3 | 69.1 | 69.9 | 70.5 | superior |
| C10-9 | 5 | mid-EO ethoxylate | 52.2 | 55.1 | 60.9 | 64.7 | 64.3 | equal |
| C10-14 | 6 | DETA quat sulfonate | 59.0 | 65.2 | 65.6 | 67.7 | 67.4 | equal |
| C10-27 | 7 | DEA amide | 53.9 | 56.0 | 58.4 | 62.0 | 65.2 | equal |
| C10-39 | 6 | amine oxide | 47.4 | 56.8 | 60.4 | 59.8 | 61.9 | equal |
| C10-41 | 6 | betaine | 56.2 | 63.0 | 63.1 | 63.7 | 64.2 | equal |
| C10-43 | 23 | sulfobetaine | 55.5 | 63.2 | 66.0 | 66.5 | 67.2 | equal |
| C12-9 | 8 | mid-EO ethoxylate | 48.8 | 54.8 | 59.4 | 59.8 | 61.4 | equal |
| C12-11 | 9 | high-EO ethoxylate | 62.5 | 67.2 | 70.7 | 70.1 | 69.6 | equal |
| C12-19 | 9 | DMAPA quat sulfonate | 55.5 | 61.7 | 64.5 | 66.1 | 66.6 | equal |
| C12-31 | 5 | DEA amide | 57.3 | 64.2 | 67.1 | 69.0 | 69.6 | equal |
| C12-46 | 23 | sulfobetaine | 56.6 | 61.2 | 63.5 | 64.6 | 65.3 | equal |
| C12-49 | 4 | mid-EO ethoxylate | 53.1 | 57.3 | 59.3 | 59.4 | 61.2 | equal |
| C16-9 | 11 | DMAPA amide | 48.0 | 53.9 | 60.1 | 62.2 | 64.7 | equal |
| C16-13 | 19 | DMAPA betaine | 50.7 | 62.5 | 63.4 | 65.3 | 66.2 | equal |
| Mix-3 | 19 | TEA ester | 55.0 | 61.6 | 63.3 | 65.6 | 66.7 | equal |
| Mix-5 | 4 | TEA ester | 60.1 | 62.0 | 64.7 | 66.3 | 67.1 | equal |
| Mix-15 | 18 | DMEA ester | 47.0 | 60.9 | 62.8 | 64.3 | 65.5 | equal |
| Mix-18 | 18 | mid-EO ethoxylate | 57.8 | 61.8 | 62.3 | 63.4 | 66.2 | equal |
| Mix-20 | 18 | high-EOB ethoxylate | 59.4 | 63.2 | 67.3 | 67.4 | 69.2 | equal |
| Mix-23 | 20 | diDETA diquat sulfonate | 58.9 | 68.2 | 69.0 | 71.0 | 71.2 | equal |
| Mix-32 | 11 | diDMAPA dibetaine | 49.6 | 58.1 | 59.4 | 62.1 | 65.5 | equal |
| C18-36 | 8 | diDMAPA monobetaine | 50.2 | 57.3 | 59.9 | 65.5 | 67.8 | equal |
| Mix-36 | 11 | diDMAPA monobetaine | 40.1 | 53.7 | 58.4 | 60.4 | 63.6 | equal |
| C18-37 | 8 | diDMAPA betaine/AO | 54.2 | 60.1 | 62.4 | 63.9 | 66.6 | equal |
| Mix-37 | 4 | diDMAPA betaine/AO | 57.4 | 61.6 | 62.9 | 64.6 | 65.5 | equal |
| Mix-38 | 18 | diDMAPA betaine quat | 44.5 | 57.1 | 62.4 | 66.0 | 67.8 | equal |
| Mix-42 | 18 | diDEA amide | 65.6 | 66.6 | 70.8 | 71.5 | 73.3 | equal |
| Mix-48 | 21 | DMAPA betaine ester | 55.3 | 62.6 | 63.9 | 65.7 | 65.9 | equal |
| Mix-73 | 21 | DMAPA AO carboxylate | 55.6 | 60.6 | 61.8 | 62.9 | 64.2 | equal |
| PUTG-11 | 7 | DMAPA sulfobetaine | 53.9 | 60.5 | 62.2 | 66.4 | 67.1 | equal |
| MTG-6 | 10 | DMAPA betaine | 62.8 | 66.7 | 68.7 | 70.2 | 72.7 | equal |
| MTG-11 | 7 | DMAPA sulfobetaine | 49.9 | 54.5 | 54.7 | 58.8 | 61.2 | equal |
| UTG-6 | 11 | DMAPA betaine | 51.9 | 60.1 | 61.9 | 62.8 | 63.3 | equal |
| UTG-7 | 4 | TEA ester quat | 59.5 | 62.7 | 63.7 | 66.0 | 66.4 | equal |
| UTG-12 | 4 | DMAPA amine oxide | 43.3 | 51.2 | 54.3 | 55.0 | 57.4 | equal |

TABLE 7

Nonionic/Amphoteric Test Samples: Comparative Examples

| Sample | Con. # | Compound class | Ave. % clean 2 | 4 | 6 | 8 | 10 | Rating |
|---|---|---|---|---|---|---|---|---|
| C10-20 | 10 | DMAPA amine oxide | 59.0 | 61.7 | 62.2 | 61.8 | 63.9 | inferior |
| C10-22 | 12 | DMAPA betaine | 57.3 | 63.9 | 66.6 | 68.8 | 72.2 | inferior |
| C10-24 | 13 | DMAPA sulfobetaine | 53.7 | 56.0 | 63.2 | 65.3 | 64.4 | inferior |
| C12-20 | 3 | DMAPA amine oxide | 30.2 | 35.9 | 39.1 | 42.7 | 46.1 | inferior |
| C12-22 | 13 | DMAPA betaine | 47.5 | 55.2 | 58.1 | 61.6 | 66.4 | inferior |
| C12-28 | 14 | amine oxide | 27.7 | 38.6 | 42.7 | 46.7 | 47.9 | inferior |
| C12-40 | 14 | betaine | 36.9 | 43.8 | 49.9 | 50.6 | 52.9 | inferior |
| C12-47 | 4 | mid-EO ethoxylate | 40.5 | 44.7 | 45.2 | 46.0 | 46.2 | inferior |
| C12-48 | 4 | mid-EO ethoxylate | 38.7 | 47.0 | 48.1 | 48.1 | 48.3 | inferior |
| C16-8 | 11 | mid-EO ethoxylate | 34.9 | 40.3 | 42.0 | 42.8 | 43.3 | inferior |
| C16-16 | 20 | betaine | 58.1 | 60.4 | 62.2 | 62.9 | 63.4 | inferior |
| C18-29 | 15 | diDMAPA amine oxide | 38.5 | 42.8 | 49.9 | 51.0 | 51.4 | inferior |
| Mix-29 | 22 | diDMAPA amine oxide | 41.6 | 49.7 | 51.6 | 53.5 | 56.6 | inferior |
| C18-31 | 15 | diDMAPA disulfobetaine | 45.2 | 50.1 | 52.3 | 53.3 | 53.3 | inferior |
| Mix-31 | 22 | diDMAPA disulfobetaine | 45.6 | 53.8 | 57.5 | 59.2 | 59.6 | inferior |
| C18-32 | 15 | diDMAPA dibetaine | 48.9 | 56.9 | 58.9 | 60.3 | 61.9 | inferior |
| C18-35 | 15 | diDMAPA quat AO | 39.0 | 48.4 | 52.4 | 55.2 | 57.4 | inferior |
| Mix-35 | 11 | diDMAPA quat AO | 36.0 | 43.0 | 49.2 | 52.0 | 56.2 | inferior |
| C18-38 | 17 | diDMAPA quat betaine | 34.4 | 46.4 | 52.5 | 57.7 | 59.4 | inferior |
| Mix-46 | 21 | ester DMAPA AO | 38.0 | 49.9 | 53.0 | 54.2 | 57.0 | inferior |
| Mix-70 | 21 | DMAPA carboxylate | 42.2 | 53.4 | 55.8 | 56.2 | 57.6 | inferior |
| Mix-78 | 20 | DMA amide carboxylate | 58.4 | 60.4 | 60.7 | 62.0 | 61.6 | inferior |
| PMTG-6 | 3 | DMAPA betaine | 51.7 | 55.8 | 56.6 | 57.6 | 60.0 | inferior |
| PMTG-11 | 3 | DMAPA sulfobetaine | 49.0 | 52.1 | 55.4 | 61.7 | 62.1 | inferior |
| PMTG-12 | 3 | DMAPA amine oxide | 34.8 | 40.3 | 44.4 | 48.0 | 49.8 | inferior |
| PUTG-6 | 3 | DMAPA betaine | 44.4 | 50.5 | 52.9 | 55.9 | 57.0 | inferior |
| PUTG-12 | 7 | DMAPA amine oxide | 42.7 | 46.4 | 48.0 | 53.0 | 56.0 | inferior |
| MTG-12 | 7 | DMAPA amine oxide | 42.7 | 47.6 | 51.9 | 54.5 | 56.1 | inferior |

As the results in Tables 6 and 7 demonstrate, it is not easy to predict which classes of compounds will provide at least good performance when tested as nonionic or amphoteric solvents in the Gardner straight line washability test. For instance, C12-24, a DMAPA sulfobetaine earns a superior rating, but other DMAPA sulfobetaines (C10-24 and PMTG-11) perform poorly in the test. C10-22, although reaching a level of cleaning equal to control by the last stroke, is inferior through the first 6 strokes, so is rated as inferior.

TABLE 8

Anionic Test Samples: Inventive Examples

| Sample | Con. # | Compound class | Ave. % clean 2 | 4 | 6 | 8 | 10 | Rating |
|---|---|---|---|---|---|---|---|---|
| C10-33 | 1 | sulfo-estolide | 52.6 | 58.8 | 67.6 | 69.2 | 69.9 | superior |
| C12-23 | 2 | DMAPA betaine sulfonate | 55.7 | 61.5 | 64.8 | 67.4 | 70.1 | superior |
| C10-1 | 10 | sulfonate | 61.8 | 65.6 | 68.0 | 68.7 | 70.5 | equal |
| C10-10 | 16 | mid-EO ethox sulfonate | 49.9 | 57.5 | 59.7 | 61.0 | 62.6 | equal |
| C10-21 | 3 | DMAPA AO sulfonate | 51.1 | 56.4 | 57.4 | 63.3 | 65.9 | equal |
| C10-26 | 3 | DMA amide sulfonate | 53.2 | 57.0 | 61.7 | 65.4 | 66.9 | equal |
| C10-29 | 16 | low-EO ethox sulfonate | 54.4 | 61.6 | 63.1 | 65.6 | 67.9 | equal |
| C10-30 | 6 | high-EO ethox sulfonate | 58.8 | 63.6 | 68.3 | 68.8 | 70.6 | equal |
| C10-34 | 3 | sulfo-estolide | 50.9 | 54.0 | 58.5 | 60.5 | 64.6 | equal |
| C10-35 | 5 | sulfo-estolide | 56.0 | 63.1 | 66.5 | 68.0 | 71.0 | equal |
| C10-37 | 16 | DMA amide sulfonate | 56.1 | 59.6 | 66.0 | 67.9 | 69.1 | equal |
| C12-1 | 16 | sulfonate | 52.6 | 60.9 | 62.6 | 65.5 | 68.0 | equal |
| C12-10 | 6 | mid-EO ethox sulfonate | 57.1 | 61.2 | 66.6 | 66.0 | 66.8 | equal |
| C12-21 | 11 | DMAPA AO sulfonate | 58.2 | 63.9 | 63.7 | 64.2 | 65.3 | equal |
| C12-34 | 8 | sulfo-estolide | 52.2 | 59.4 | 61.3 | 63.8 | 65.3 | equal |
| C12-35 | 9 | sulfo-estolide | 57.1 | 64.8 | 68.2 | 70.5 | 72.5 | equal |
| C12-36 | 9 | sulfo-estolide | 58.2 | 62.0 | 68.0 | 70.9 | 72.2 | equal |
| C12-37 | 9 | sulfo-estolide | 56.3 | 65.8 | 68.3 | 71.1 | 72.3 | equal |
| C12-42 | 11 | DMAPA sulfonate | 54.5 | 60.2 | 61.5 | 63.5 | 65.3 | equal |
| C12-43 | 24 | sulfo-estolide | 57.8 | 62.6 | 64.3 | 64.9 | 66.2 | equal |
| C12-44 | 24 | sulfo-estolide | 58.6 | 62.9 | 64.4 | 65.6 | 67.0 | equal |
| C16-1 | 20 | sulfonate | 62.7 | 69.2 | 69.4 | 70.2 | 70.2 | equal |
| C16-12 | 20 | DMAPA AO sulfonate | 65.7 | 69.7 | 70.3 | 71.0 | 71.0 | equal |
| C18-1 | 15 | sulfonate | 52.7 | 59.2 | 59.6 | 62.1 | 64.0 | equal |
| C18-28 | 17 | DMAPA diquat sulfonate | 52.2 | 61.1 | 64.3 | 67.6 | 69.2 | equal |
| C18-30 | 17 | diDMAPA AO sulfonate | 55.3 | 59.2 | 64.1 | 65.9 | 66.2 | equal |
| C18-33 | 17 | DMAPA dibetaine sulfonate | 58.7 | 63.3 | 66.2 | 67.6 | 68.1 | equal |
| Mix-61 | 21 | low-EO ethox sulfonate | 58.8 | 62.5 | 64.8 | 65.0 | 65.5 | equal |
| C18-63 | 17 | sulfo-estolide | 52.4 | 55.3 | 64.2 | 66.0 | 66.9 | equal |

TABLE 8-continued

| | | Anionic Test Samples: Inventive Examples | | | | | |
|---|---|---|---|---|---|---|---|
| | | | Con. Ave. % clean | | | | |
| Sample | # | Compound class | 2 | 4 | 6 | 8 | 10 | Rating |
| C18-64 | 17 | sulfo-estolide | 52.2 | 62.0 | 64.6 | 65.6 | 67.0 | equal |
| C18-68 | 17 | diDMAPA sulfonate | 53.9 | 63.3 | 66.8 | 67.6 | 70.0 | equal |

TABLE 9

| | | Anionic Test Samples: Comparative Examples | | | | | |
|---|---|---|---|---|---|---|---|
| | | | Con. Ave. % clean | | | | |
| Sample | # | Compound class | 2 | 4 | 6 | 8 | 10 | Rating |
| C10-23 | 13 | DMAPA betaine sulfonate | 56.1 | 59.7 | 61.3 | 64.8 | 68.0 | inferior |
| C10-32 | 13 | sulfo-estolide | 54.2 | 60.4 | 63.5 | 67.0 | 67.2 | inferior |
| C12-29 | 14 | DMA amide sulfonate | 50.0 | 53.4 | 56.2 | 58.5 | 59.4 | inferior |
| C12-32 | 14 | high-EO ethox sulfonate | 42.3 | 49.9 | 51.5 | 53.2 | 53.5 | inferior |
| C12-33 | 14 | low-EO ethox sulfonate | 46.9 | 55.3 | 57.1 | 58.4 | 59.5 | inferior |
| C16-11 | 11 | DMAPA sulfonate | 28.8 | 32.7 | 34.9 | 37.1 | 37.2 | inferior |

As the results in Tables 8 and 9 demonstrate, it is not easy to predict which classes of compounds will provide at least good performance when tested as anionic solvents in the Gardner straight line washability test. For instance, C10-30, a high-EO ethoxylate sulfonate earns a good rating, but C12-32, another high-EO ethoxylate sulfonate performs poorly in the test. Similarly, DMA amide sulfonate C10-37 achieves a good rating, but DMA amide sulfonate C12-29 proves inferior.

Industrial Degreaser Formulations

This test measures the ability of a solvent to clean a greasy dirt soil from a white vinyl tile. The soil is the same as used in the Gardner ASTM D4488-95 A5 method, only applied to the tile with a brush. The test consists of placing a drop of the test solvent onto the soiled tile, waiting 10 seconds (neat samples), or 30 seconds (diluted), then adding a second drop adjacent to the first, waiting the prescribed time, adding a third drop, etc. After a few minutes the dropping is stopped and the tile rinsed, photographed, and judged for cleaning versus control neat, and in formulation diluted.

Neat samples are tested versus Steposol® M8-10, a mixture of N,N-dimethylcapramide and N,N-dimethylcaprylamide, product of Stepan.

Diluted samples are made from test actives (5.0 g), Ammonyx® LMDO (lauramidopropylamine oxide, product of Stepan, 10.0 g), and deionized water (q.s. to 100 g). The control for the diluted samples replaces the test actives with Steposol M8-10 (5.0 g).

Results appear in Table 10. The $C_{10}$-$C_{12}$ amides derived from metathesis of soybean oil outperformed all of the other tested materials as degreaser solvents.

As the results in Table 10 demonstrate, it is not easy to predict which classes of compounds will provide even good performance when tested as solvent-based degreasers. For instance, C10-25, a DMA amide earns a superior rating, but DMAPA amides C10-17 and C12-17 and other DEA or DMA-based amides, including UTG-15 and UTG-16, perform poorly in the test.

TABLE 10

| Performance as a Solvent in Industrial Degreasers | | | |
|---|---|---|---|
| Sample | Composition class | Neat | Diluted |
| Inventive Examples | | | |
| C10-25 | DMA amide | superior | superior |
| C12-25 | DMA amide | equal | superior |
| Comparative Examples | | | |
| C10-0 | unsaturated methyl ester | inferior | inferior |
| C10-6 | DMEA ester | inferior | inferior |
| C10-8 | low-EO ethoxylate | inferior | inferior |
| C10-17 | DMAPA amide | inferior | inferior |
| C10-38 | amine | inferior | inferior |
| C12-0 | unsaturated methyl ester | inferior | inferior |
| C12-4 | MDEA ester | inferior | inferior |
| C12-6 | DMEA ester | inferior | inferior |
| C12-8 | low-EO ethoxylate | inferior | inferior |
| C12-17 | DMAPA amide | inferior | inferior |
| C12-26 | amine | inferior | inferior |
| C12-39 | fatty acid | inferior | inferior |
| C16-0 | unsaturated methyl ester | inferior | inferior |
| C16-4 | TEA ester | inferior | inferior |
| C16-6 | MDEA ester | inferior | inferior |
| C16-14 | DMA amide | inferior | inferior |
| C16-15 | amine | inferior | inferior |
| Mix-2 | IPA ester | inferior | inferior |
| C18-9 | MDEA ester | inferior | inferior |
| Mix-9 | MDEA ester | inferior | inferior |
| Mix-11 | MDEA ester | inferior | inferior |
| Mix-13 | MDEA ester | inferior | inferior |
| Mix-17 | low-EO ethoxylate | inferior | inferior |
| Mix-59 | DMA ester | inferior | inferior |
| UTG-9 | MDEA ester | inferior | inferior |
| UTG-15 | DMA amide | inferior | inferior |
| UTG-16 | DEA amide | inferior | inferior |

The preceding examples are meant only as illustrations. The following claims define the invention.

We claim:

1. A hard surface cleaner comprising 0.1 to 10 wt. % of at least one metathesis-based anionic surfactant selected from the group consisting of:

(a) $C_{10}$, $C_{12}$, $C_{16}$, or $C_{18}$ sulfonates having the structure:

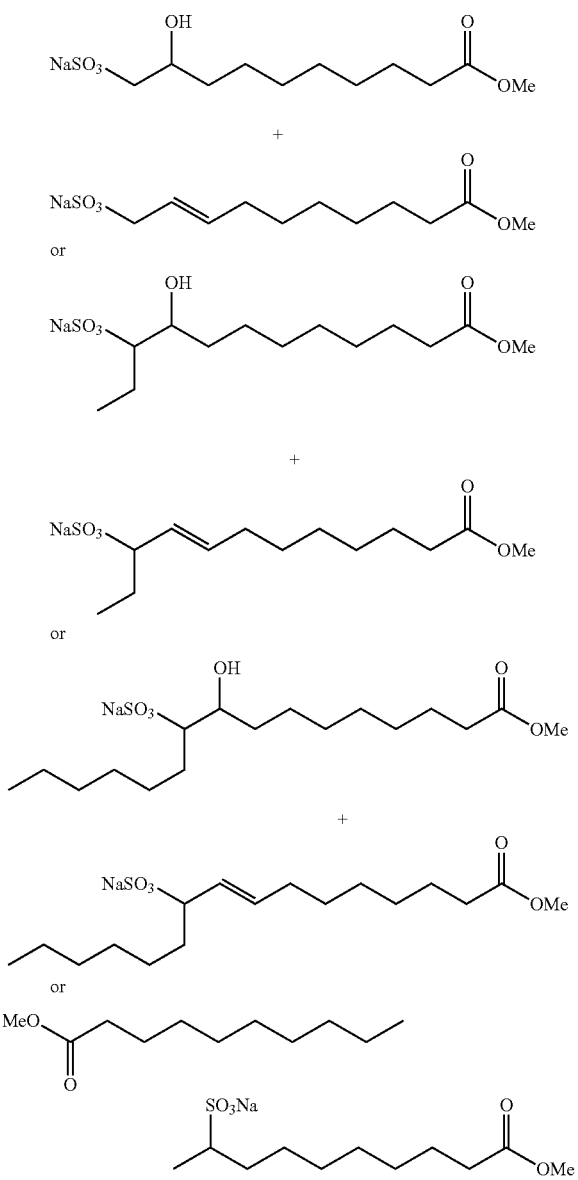

(b) $C_{10}$ amide sulfonates having the structure:

(c) sulfonated $C_{10}$ fatty ester alkoxylates having the structure:

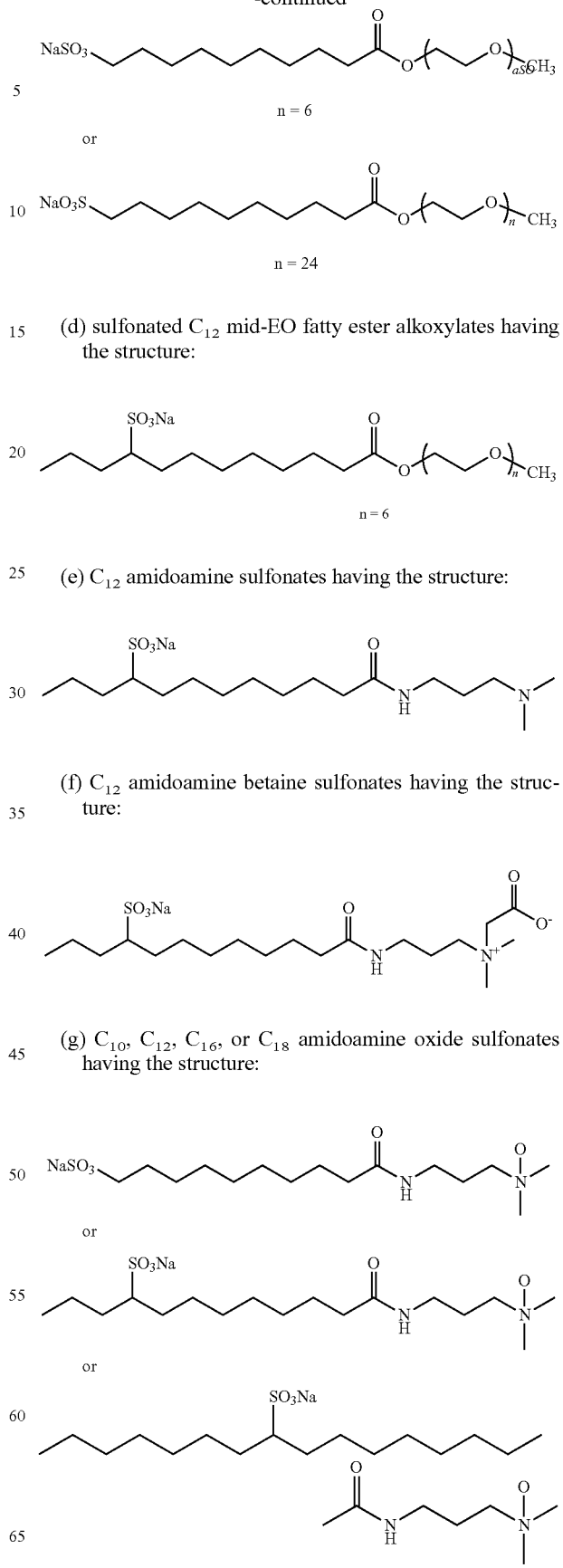

n = 6 or n = 24

(d) sulfonated $C_{12}$ mid-EO fatty ester alkoxylates having the structure:

n = 6

(e) $C_{12}$ amidoamine sulfonates having the structure:

(f) $C_{12}$ amidoamine betaine sulfonates having the structure:

(g) $C_{10}$, $C_{12}$, $C_{16}$, or $C_{18}$ amidoamine oxide sulfonates having the structure:

or

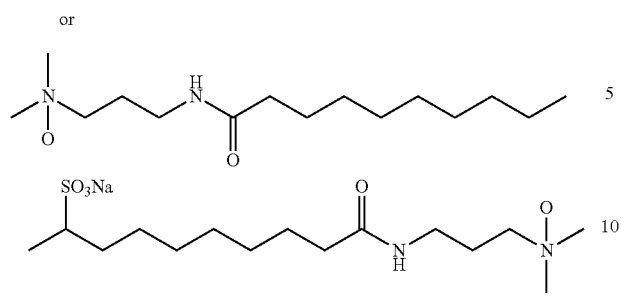

(h) sulfonated $C_{18}$ low-EO fatty ester alkoxylates having the structure:

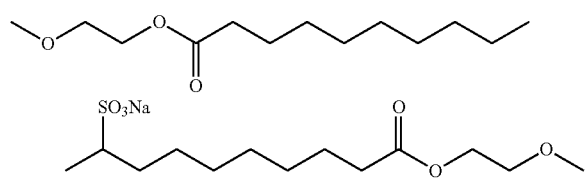

(i) $C_{18}$ diamidoamine sulfonates having the structure:

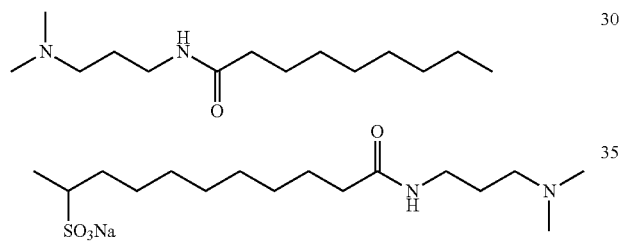

(j) $C_{18}$ amidoamine dibetaine sulfonates having the structure:

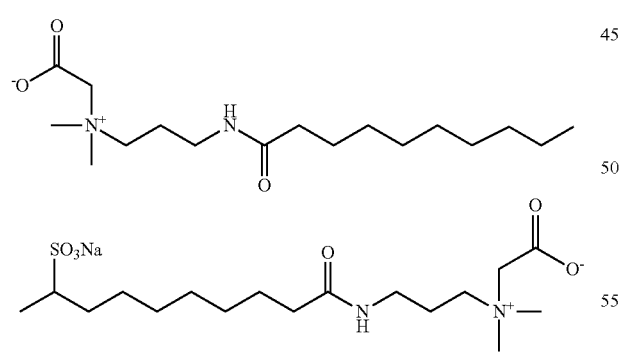

(k) $C_{18}$ amidoamine diquat sulfonates having the structure:

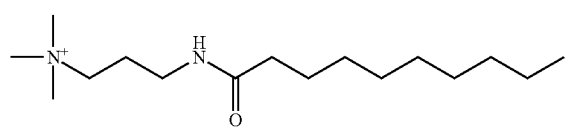

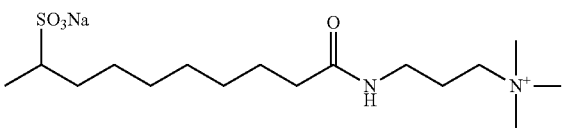

(l) sulfo-estolides of $C_{10}$ unsaturated fatty acids and $C_{10}$ or $C_{18}$ saturated fatty acids having the structure:

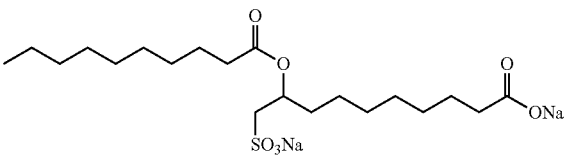

or

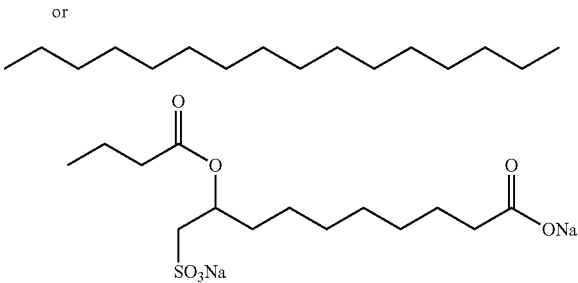

(m) sulfo-estolides of $C_{10}$ or $C_{12}$ unsaturated fatty esters and $C_{10}$ or $C_{12}$ saturated fatty acids having the structure:

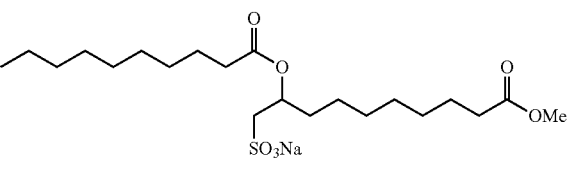

or

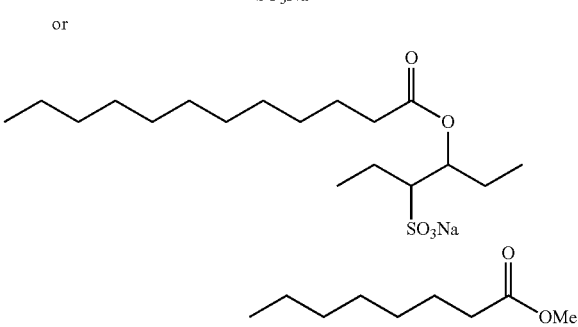

(n) sulfo-estolides of $C_{12}$ unsaturated fatty acids having the structure:

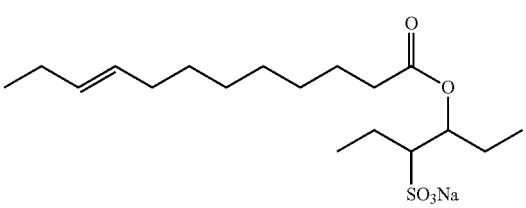

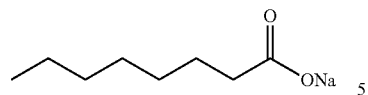

(o) sulfo-estolides of $C_{12}$ unsaturated fatty acids and $C_{12}$ or $C_{18}$ saturated fatty acids having the structure:

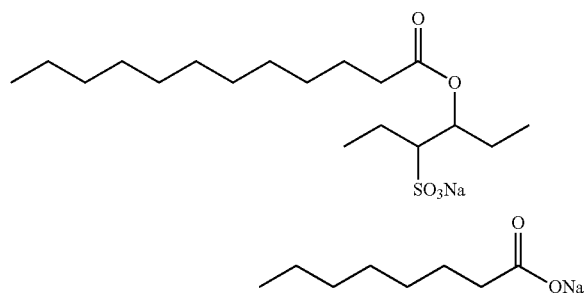

or

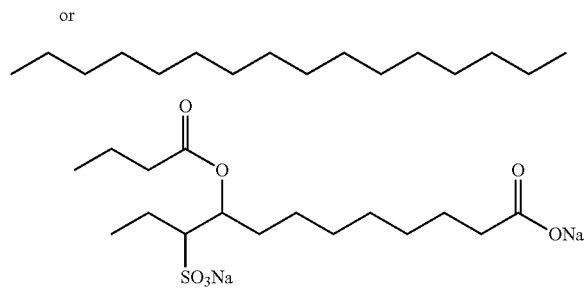

or

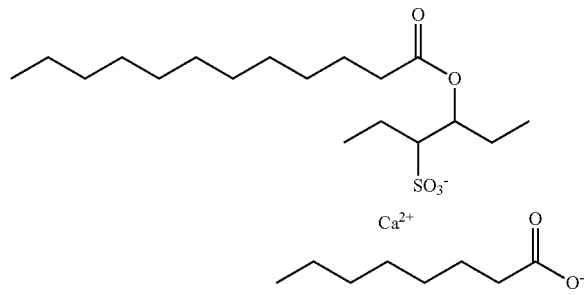

or

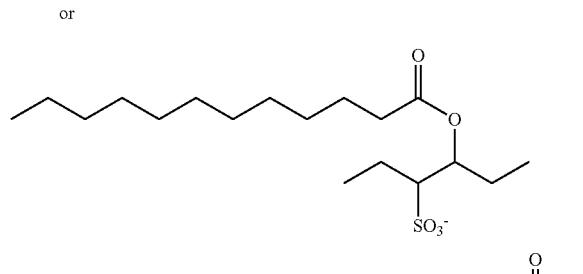

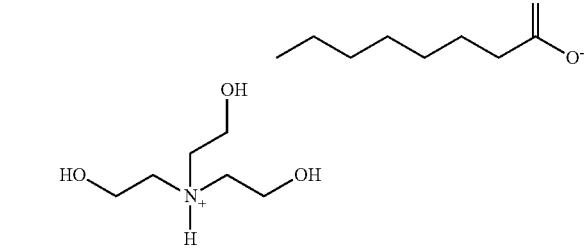

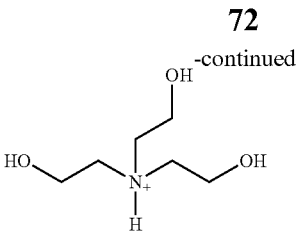

and (p) sulfo-estolides of $C_{18}$ dibasic esters and $C_{10}$ fatty acids having the structure:

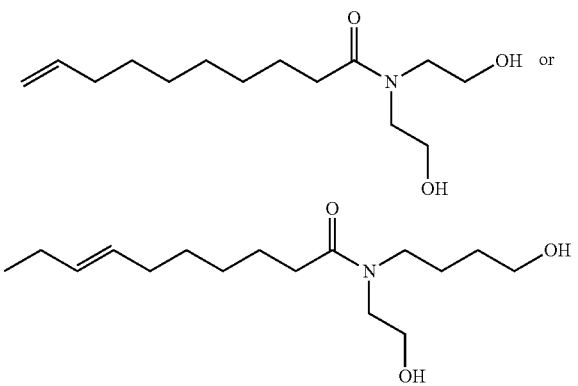

2. The cleaner of claim 1 further comprising 0.1 to 10 wt. % of a nonionic or amphoteric surfactant.

3. The cleaner of claim 1 wherein the anionic surfactant is produced from an ester or acid reactant having at least 1 mole % of trans-$\Delta^9$ unsaturation.

4. The cleaner of claim 1 further comprising 50 to 99 wt. % of water.

5. The cleaner of claim 1 further comprising 0.5 to 20 wt. % of an organic solvent.

6. The cleaner of claim 1 further comprising one or more additives selected from the group consisting of builders, buffers, abrasives, electrolytes, bleaching agents, fragrances, dyes, foaming control agents, antimicrobial agents, thickeners, pigments, gloss enhancers, enzymes, detergents, surfactants, cosolvents, dispersants, polymers, silicones, and hydrotropes.

7. A hard surface cleaner comprising 0.1 to 10 wt. % of at least one metathesis-based nonionic or amphoteric surfactant selected from the group consisting of:

(a) $C_{10}$ or $C_{12}$ amides having the structure:

(b) $C_{10}$, $C_{12}$, or $C_{18}$ imidazoline quat sulfonates having the structure:
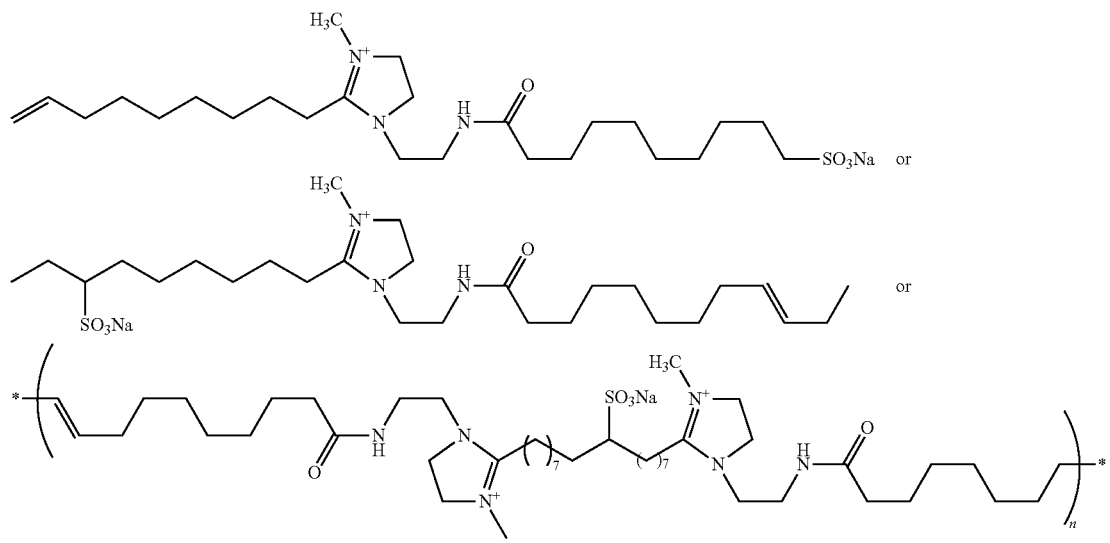
(c) $C_{10}$ or $C_{12}$ mid- or high-EO fatty ester alkoxylates having the structure:
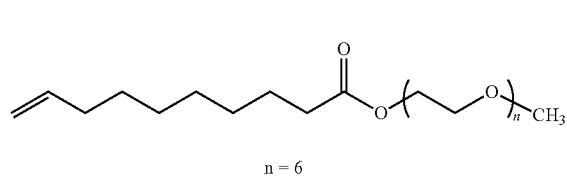
n = 6
or
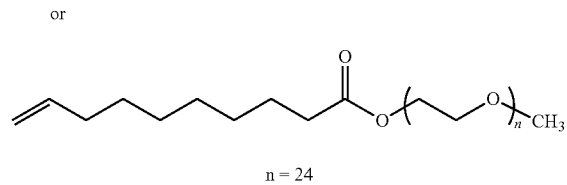
n = 24
or
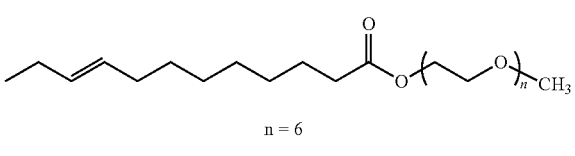
n = 6
or
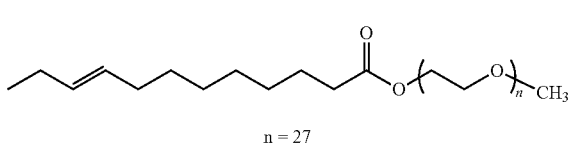
n = 27
or
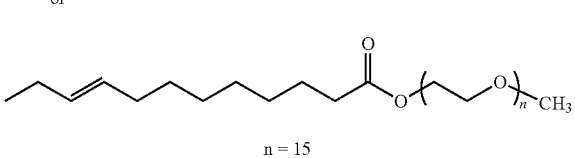
n = 15
(d) $C_{10}$ amine oxides having the structure:
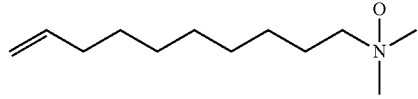
(e) $C_{10}$ betaines having the structure:
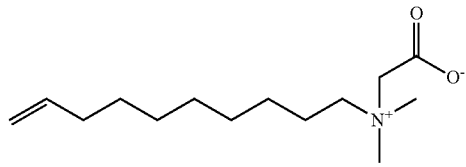 [SMILES: C=CCCCCCCCC[N+](C)(C)CC(=O)[O-]]
(f) $C_{10}$ and $C_{12}$ sulfobetaines having the structure:
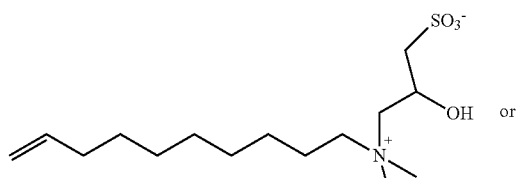
or
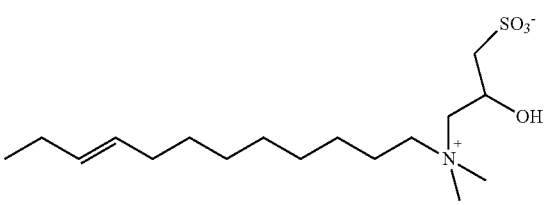

(g) $C_{12}$ amidoamine sulfobetaines having the structure:
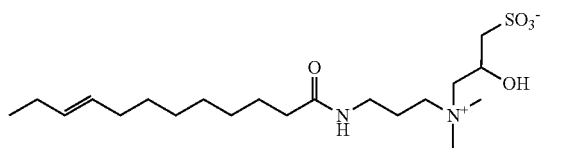
(h) $C_{10}$ or $C_{12}$ amidoamine quat sulfonates having the structure:
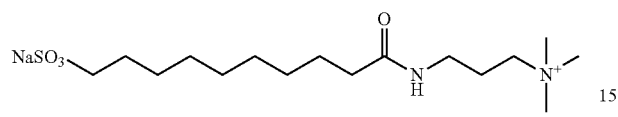
-continued
or
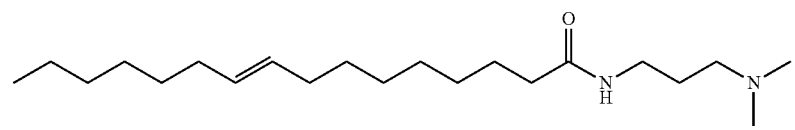 [SMILES: CCCCCC/C=C/CCCCCCCC(=O)NCCCN(C)C]
(i) $C_{16}$ amidoamines having the structure:
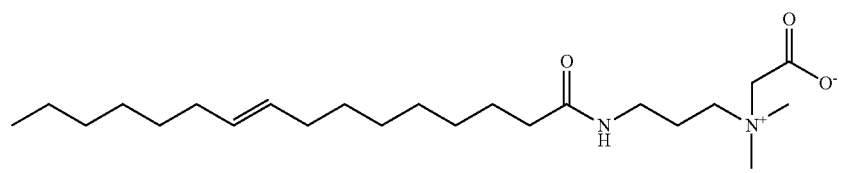 [SMILES: CCCCCC/C=C/CCCCCCCC(=O)NCCC[N+](C)(C)CC(=O)[O-]]
(j) $C_{16}$ amidoamine betaines having the structure:
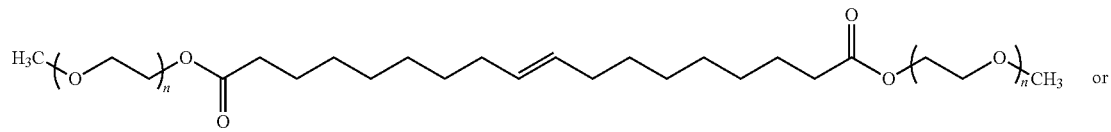
(k) $C_{18}$ mid- or high-EO ethoxylates having the structure:
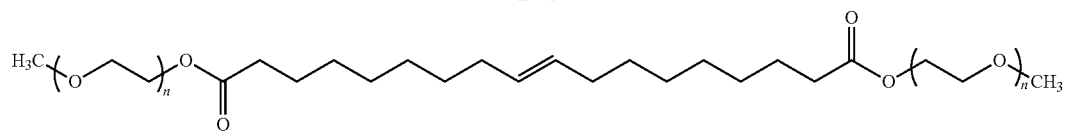
n = 6
n = 24
(l) $C_{18}$ amidoamine monobetaines having the structure:
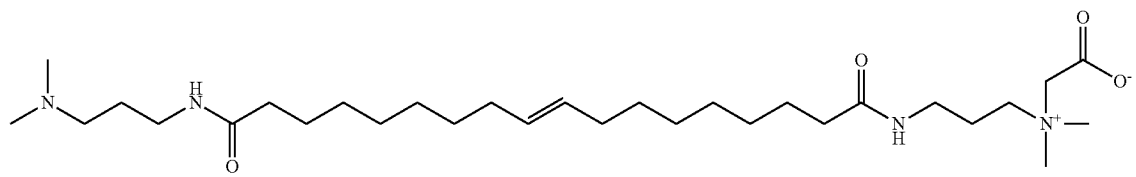 [SMILES: CN(C)CCCNC(=O)CCCCCCC/C=C/CCCCCCCC(=O)NCCC[N+](C)(C)CC(=O)[O-]]

(m) C$_{18}$ amidoamine dibetaines having the structure:
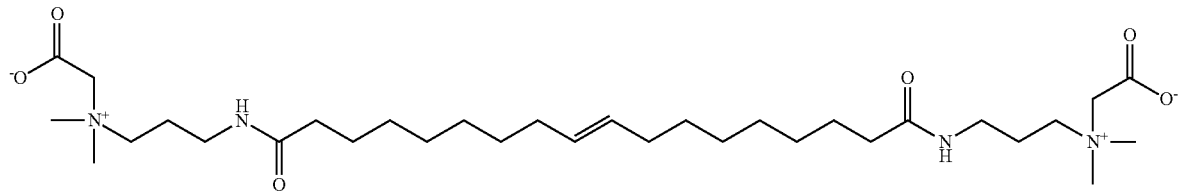
(n) C$_{18}$ amidoamine monobetaine oxides having the structure:
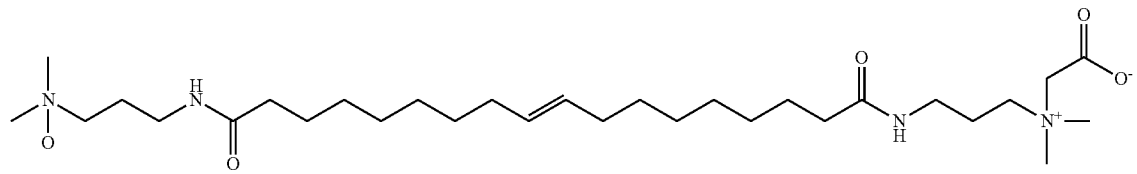
(o) C$_{18}$ amidoamine monobetaine quats having the structure:
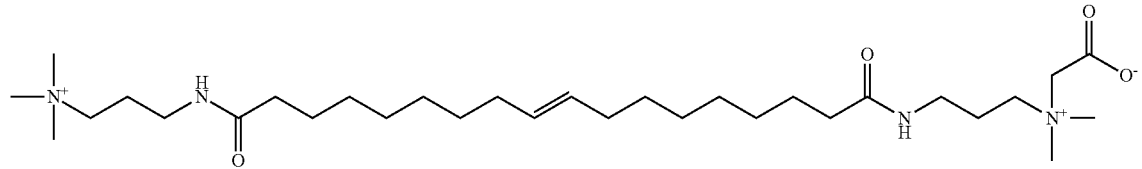 [SMILES: C[N+](C)(C)CCCNC(=O)CCCCCCC/C=C/CCCCCCCC(=O)NCCC[N+](C)(C)CC(=O)[O-]]
(p) C$_{18}$ amidoamine monobetaine esters having the structure:
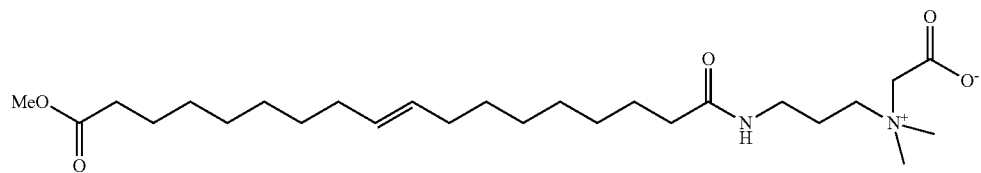 [SMILES: COC(=O)CCCCCCC/C=C/CCCCCCCC(=O)NCCC[N+](C)(C)CC(=O)[O-]]
(q) C$_{18}$ amidoamine oxide carboxylates having the structure:
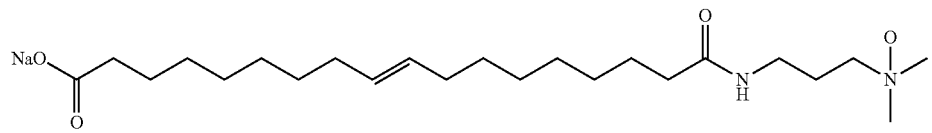

(r) C<sub>18</sub> esteramines having the structure:
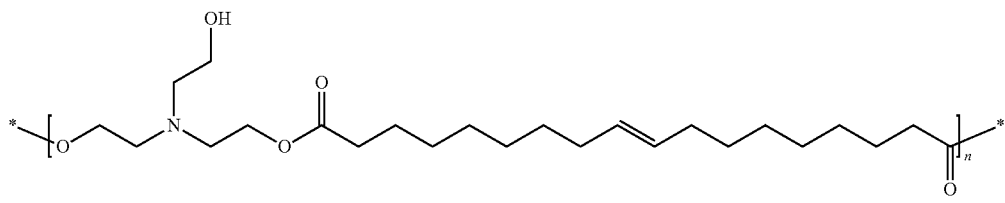
or
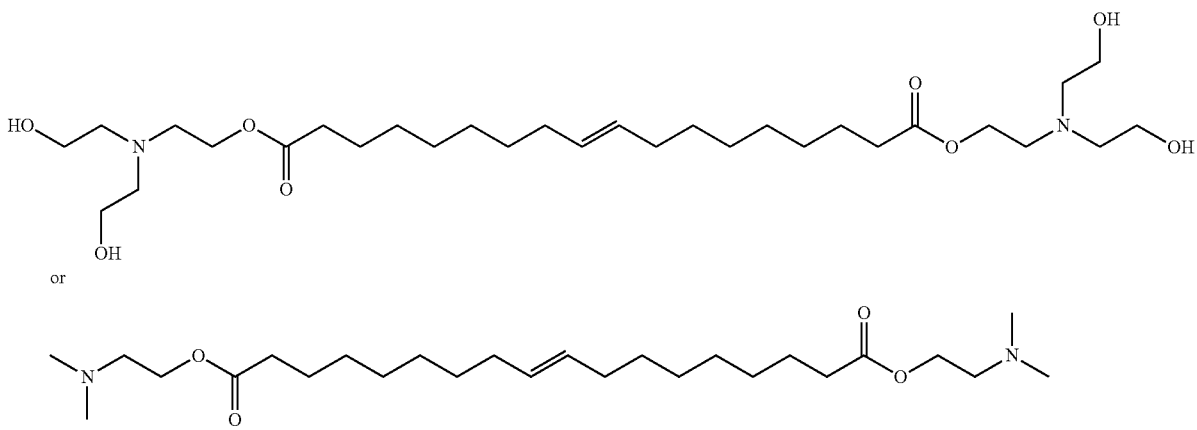
(s) C<sub>18</sub> diamides having the structure:
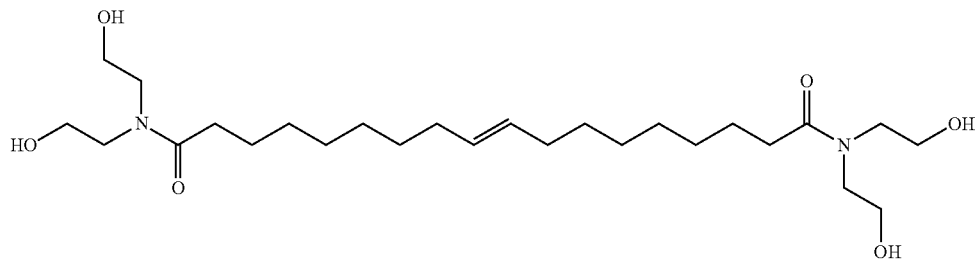 [SMILES: O=C(CCCCCCC/C=C/CCCCCCCC(=O)N(CCO)CCO)N(CCO)CCO]
(t) amidoamine sulfobetaines made from cross-metathesized palm or soybean oil or from self-metathesized soybean oil having the structure:
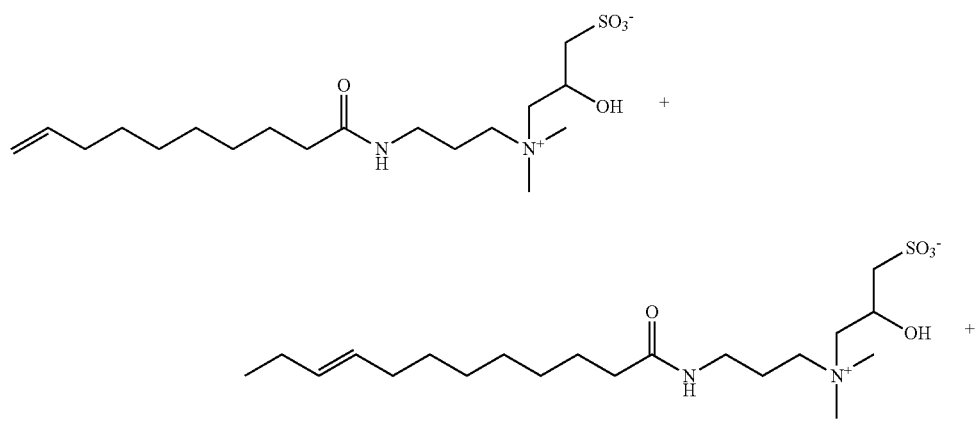

-continued
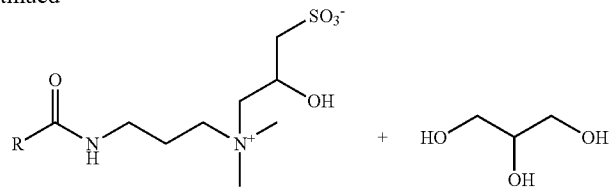
R = C16, C18 Sat.
or
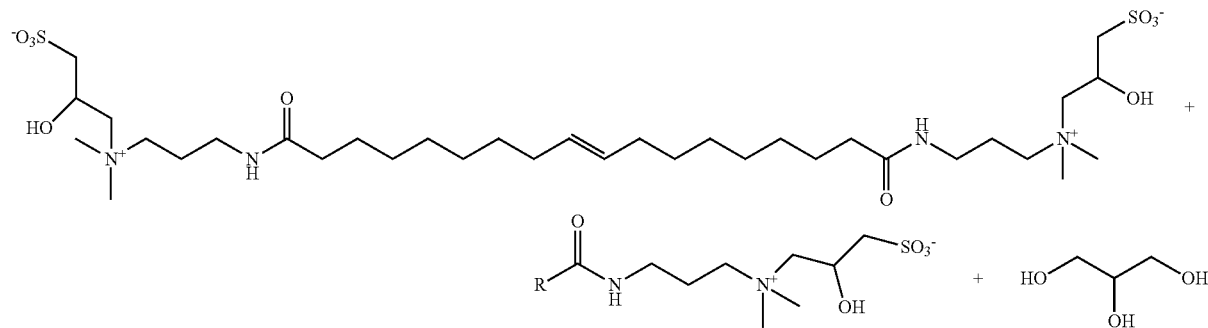
R = C16, C18 Sat. + Unsat.
(u) amidoamine betaines made from cross-metathesized or self-metathesized soybean oil having the structure:
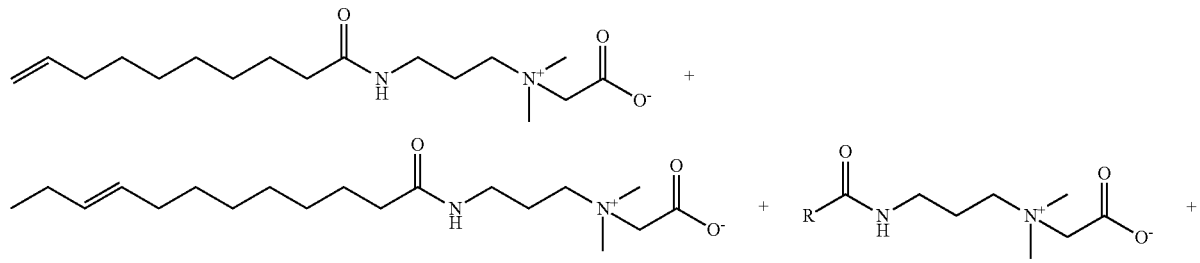
R = C16, C18 Sat.
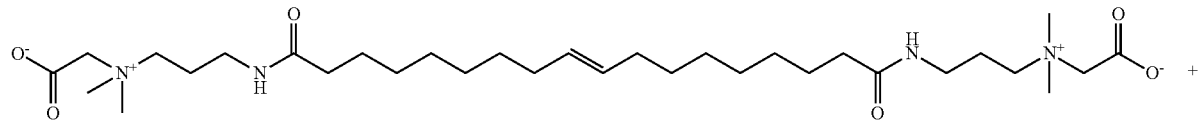
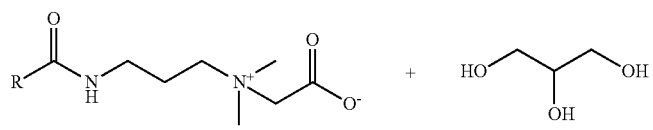
R = C16, C18 Sat. + Unsat.

and (v) amidoamine oxides made from cross-metathesized soybean oil having the structure:

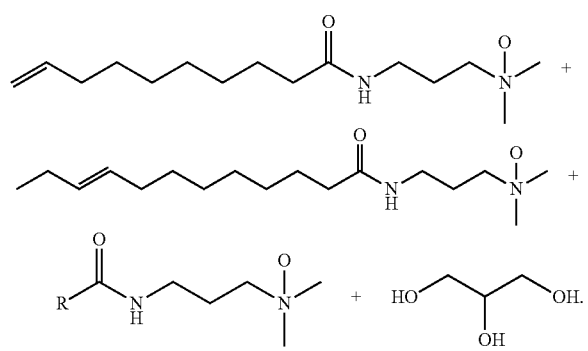

R = C16, C18 Sat.

8. The cleaner of claim 7 further comprising 0.1 to 10 wt. % of an anionic surfactant.

9. The cleaner of claim 7 further comprising 50 to 99 wt. % of water.

10. The cleaner of claim 7 further comprising 0.5 to 20 wt. % of an organic solvent.

11. An industrial degreaser comprising at least one metathesis-based solvent selected from the group consisting of $C_{10}$ or $C_{12}$ amides having the structure:

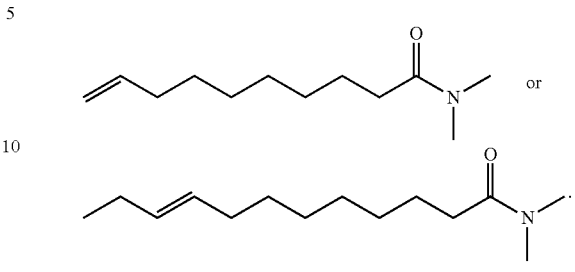

12. The degreaser of claim 11 comprising 2 to 20 wt. % of the $C_{10}$ or $C_{12}$ amide, 3 to 25 wt. % of a fatty amine oxide, and 55 to 95 wt. % of water.

13. The cleaner of claim 11 or the degreaser of claim 11 further comprising one or more additives selected from the group consisting of builders, buffers, abrasives, electrolytes, bleaching agents, fragrances, dyes, foaming control agents, antimicrobial agents, thickeners, pigments, gloss enhancers, enzymes, detergents, surfactants, cosolvents, dispersants, polymers, silicones, and hydrotropes.

* * * * *

UNITED STATES PATENT AND TRADEMARK OFFICE
CERTIFICATE OF CORRECTION

| | | |
|---|---|---|
| PATENT NO. | : 9,303,234 B2 | Page 1 of 1 |
| APPLICATION NO. | : 13/879792 | |
| DATED | : April 5, 2016 | |
| INVENTOR(S) | : Dave R. Allen et al. | |

It is certified that error appears in the above-identified patent and that said Letters Patent is hereby corrected as shown below:

Claims

In claim 7, column 72, lines 60-65, the formula should appear as follows:

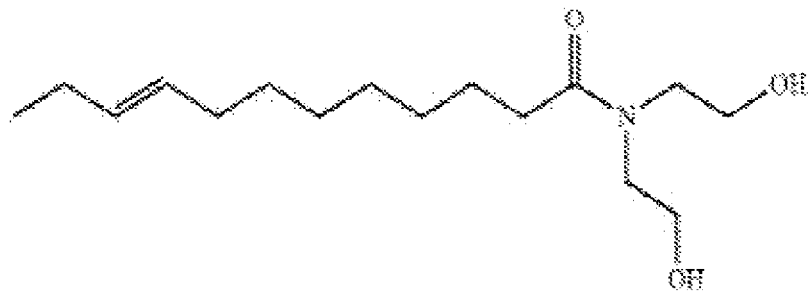

Signed and Sealed this
Nineteenth Day of July, 2016

Michelle K. Lee
*Director of the United States Patent and Trademark Office*